(12) United States Patent
Choi et al.

(10) Patent No.: US 8,394,846 B2
(45) Date of Patent: Mar. 12, 2013

(54) DUAL-ACTING ANTIHYPERTENSIVE AGENTS

(75) Inventors: Seok-Ki Choi, Ann Arbor, MI (US); Paul R. Fatheree, San Francisco, CA (US); Ryan Hudson, San Jose, CA (US); Keith Jendza, Boston, MA (US); Robert Murray McKinnell, Millbrae, CA (US); Vivek Sasikumar, Morrisville, NC (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 13/361,099

(22) Filed: Jan. 30, 2012

(65) Prior Publication Data

US 2012/0129900 A1 May 24, 2012

Related U.S. Application Data

(62) Division of application No. 12/826,976, filed on Jun. 30, 2010, now Pat. No. 8,143,298, which is a division of application No. 12/012,161, filed on Jan. 31, 2008, now Pat. No. 7,777,077.

(60) Provisional application No. 60/899,264, filed on Feb. 2, 2007, provisional application No. 60/901,531, filed on Feb. 15, 2007.

(51) Int. Cl.
    A01N 43/64      (2006.01)
    A01N 37/12      (2006.01)
    A01N 41/06      (2006.01)

(52) U.S. Cl. ............... 514/381; 514/603; 514/562

(58) Field of Classification Search .......... 514/381, 514/603, 562
See application file for complete search history.

(56) References Cited

U.S. PATENT DOCUMENTS

| | | | |
|---|---|---|---|
| 4,513,009 A | 4/1985 | Roques et al. | |
| 4,610,816 A | 9/1986 | Berger | |
| 4,722,810 A | 2/1988 | Delaney et al. | |
| 4,929,641 A | 5/1990 | Haslanger et al. | |
| 5,030,654 A | 7/1991 | Barnish et al. | |
| 5,138,069 A | 8/1992 | Carini et al. | |
| 5,155,100 A | 10/1992 | Erion et al. | |
| 5,217,996 A | 6/1993 | Ksander | |
| 5,270,317 A | 12/1993 | Bernhart et al. | |
| 5,294,632 A | 3/1994 | Erion et al. | |
| 5,399,578 A | 3/1995 | Buhlmayer et al. | |
| 5,508,272 A | 4/1996 | Robl | |
| 5,587,375 A | 12/1996 | Robl | |
| 5,591,762 A | 1/1997 | Hauel et al. | |
| 5,616,599 A | 4/1997 | Yanagisawa et al. | |
| 5,705,517 A | 1/1998 | Naka et al. | |
| 5,864,043 A | 1/1999 | Narr et al. | |
| 5,965,592 A | 10/1999 | Buhlmayer et al. | |
| 6,602,866 B2 | 8/2003 | Flynn et al. | |
| 6,777,443 B2 | 8/2004 | Fink | |
| 6,852,745 B2 | 2/2005 | Murugesan et al. | |
| 7,060,721 B1 | 6/2006 | Oku et al. | |
| 7,834,041 B2 | 11/2010 | Choi et al. | |
| 7,863,309 B2 | 1/2011 | Choi et al. | |
| 7,879,896 B2 | 2/2011 | Allegretti et al. | |
| 7,989,484 B2 | 8/2011 | Allegretti et al. | |
| 8,013,005 B2 | 9/2011 | Allegretti et al. | |
| 2002/0143024 A1 | 10/2002 | Murugesan et al. | |
| 2003/0144215 A1 | 7/2003 | Ksander et al. | |
| 2006/0046978 A1 | 3/2006 | Pierau et al. | |
| 2008/0318951 A1 | 12/2008 | Allegretti et al. | |
| 2009/0149521 A1 | 6/2009 | Choi et al. | |

FOREIGN PATENT DOCUMENTS

| | | |
|---|---|---|
| EP | 0 361 365 A1 | 4/1990 |
| EP | 0 437 103 A2 | 7/1991 |
| EP | 0 498 361 A2 | 2/1992 |
| EP | 0 505 954 A1 | 9/1992 |
| EP | 0 726 072 A2 | 8/1996 |
| JP | 06 184086 | 7/1994 |
| JP | 07 048360 | 2/1995 |
| JP | 2003 048874 | 2/2003 |
| WO | WO 92/13564 | 8/1992 |
| WO | WO 00/01389 A2 | 1/2000 |
| WO | WO 2006/027680 A1 | 3/2006 |
| WO | WO 2006/086456 A2 | 8/2006 |
| WO | WO 2007/045663 A2 | 4/2007 |
| WO | WO 2007/056546 A1 | 5/2007 |
| WO | WO 2007/106708 A2 | 9/2007 |
| WO | WO 2007/109456 A2 | 9/2007 |
| WO | WO 2008/142576 A2 | 11/2008 |

OTHER PUBLICATIONS

Jandeleit-Dahm, Journal of Human Hypertension (2006) 20, 478-481.*
Gu et al. J Clin Pharmacol, 2010, 50, 401-414.*
Chrysant, Steven G.Drugs of the Future (2011), 36(3), 183-190.*
Hegde et al. Cardioascular Pharmacology, 2011, 57(4), 495-504.*
Fournie-Zaluski et al., "Design of Orally Active Dual Inhibitors of Neutral Endopeptidase and Angiotensin-Converting Enzyme with long Duration of Action" *Journal of Medicinal Chemistry* 39:2594-2608 (1996).

(Continued)

*Primary Examiner* — Nizal Chandrakumar
(74) *Attorney, Agent, or Firm* — Jeffrey A. Hagenah; Shelley Eberle

(57) ABSTRACT

The invention is directed to compounds of formula I:

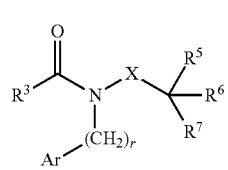

(I)

wherein Ar, r, $R^3$, X, and $R^{5-7}$ are as defined in the specification, and pharmaceutically acceptable salts thereof. The compounds of formula I have $AT_1$ receptor antagonist activity and neprilysin inhibition activity. The invention is also directed to pharmaceutical compositions comprising such compounds; methods of using such compounds; and a process and intermediates for preparing such compounds.

1 Claim, No Drawings

OTHER PUBLICATIONS

Gardiner et al., "Regional hemodynamic effects of neutral endopeptidase inhibition and angiotensin (AT1) receptor antagonism alone or in combination in conscious spontaneously hypertensive rats", The Journal of Pharmacology and Experimental Therapeutics, vol. 319 No. 1, pp. 340-348 (2006).

Middlemiss et al., "Benzofuran based angiotensin II antagonists related to GR117289: Part II; amino acid amides", Bioorganic & Medicinal Chemistry Letters, vol. 3, No. 10, pp. 2043-2046 (1993).

Pu et al., "The effect of combined AT1 receptor antagonist and neutral endopeptidase (NEP) inhibitor compared to the dual angiotensin converting enzyme inhibitor/NEP on endothelial function and vascular remodeling of SHRSP", Abstract presented at the Canadian Cardiovascular Congress (Oct. 2004).

Robl et al., "Recent advances in the design and development of vasopeptidase inhibitors", Expert Opinion on Therapeutic Patents, 9(12), pp. 1665-1677 (1999).

Shah et al., "Angiotensin II—$AT_1$ Receptor Antagonist: design, synthesis and evaluation of substituted carboxamido benzoimidazole derivatives", *European Journal of Medicinal Chemistry*, 43(9), pp. 1808-1812 (2008).

* cited by examiner

DUAL-ACTING ANTIHYPERTENSIVE AGENTS

CROSS-REFERENCE TO RELATED APPLICATIONS

This application is a divisional of U.S. Ser. No. 12/826,976, filed on Jun. 30, 2010, now allowed, which is a divisional of U.S. Ser. No. 12/012,161, filed on Jan. 31, 2008, now issued as U.S. Pat. No. 7,777,077, which claims the benefit of U.S. Provisional Application No. 60/899,264, filed on Feb. 2, 2007 and No. 60/901,531, filed on Feb. 15, 2007; the entire disclosures of which are incorporated herein by reference in their entirety.

BACKGROUND OF THE INVENTION

1. Field of the Invention

The present invention relates to novel compounds having angiotensin II type 1 ($AT_1$) receptor antagonist activity and neprilysin-inhibition activity. The invention also relates to pharmaceutical compositions comprising such compounds, processes and intermediates for preparing such compounds and methods of using such compounds to treat diseases such as hypertension.

2. State of the Art

The aim of antihypertensive therapy is to lower blood pressure and prevent hypertension-related complications such as myocardial infarction, stroke, and renal disease. For patients with uncomplicated hypertension (for example, no risk factors, target organ damage, or cardiovascular disease), it is hoped that reducing blood pressure will prevent development of cardiovascular and renal comorbidities, conditions that exist at the same time as the primary condition in the same patient. For those patients with existing risk factors or comorbidities, the therapeutic target is the slowing of comorbid disease progression and reduced mortality.

Physicians generally prescribe pharmacological therapies for patients whose blood pressure cannot be adequately controlled by dietary and/or lifestyle modifications. Commonly used therapeutic classes act to promote diuresis, adrenergic inhibition, or vasodilation. A combination of drugs is often prescribed, depending upon what comorbidities are present.

There are five common drug classes used to treat hypertension: diuretics, which include thiazide and thiazide-like diuretics such as hydrochlorothiazide, loop diuretics such as furosemide, and potassium-sparing diuretics such as triamterene; $\beta_1$ adrenergic receptor blockers such as metoprolol succinate and carvedilol; calcium channel blockers such as amlodipine; angiotensin-converting enzyme (ACE) inhibitors such as captopril, benazepril, enalapril, enalaprilat, lisinopril, quinapril, and ramipril; and $AT_1$ receptor antagonists, also known as angiotensin II type 1 receptor blockers (ARBs), such as candesartan cilexetil, eprosartan, irbesartan, losartan, olmesartan medoxomil, telmisartan, and valsartan. Combinations of these drugs are also administered, for example, a calcium channel blocker (amlodipine) and an ACE inhibitor (benazepril), or a diuretic (hydrochlorothiazide) and an ACE inhibitor (enalapril). All of these drugs, when used appropriately, are effective in the treatment of hypertension. However, patient compliance remains an issue and physicians often prescribe agents on the basis of a benign side-effect profile, at the expense of agents with similar or marginally improved efficacy. As a result, it is believed that only 50% of treated hypertensive patients achieve satisfactory blood pressure control.

In addition, each of the major classes of antihypertensive agents have some drawbacks. Diuretics can adversely affect lipid and glucose metabolism, and are associated with other side effects, including orthostatic hypotension, hypokalemia, and hyperuricemia. Beta blockers can cause fatigue, insomnia, and impotence; and some beta blockers can also cause reduced cardiac output and bradycardia, which may be undesirable in some patient groups. Calcium channel blockers are widely used but it is debatable as to how effectively these drugs reduce fatal and nonfatal cardiac events relative to other drug classes. ACE inhibitors can cause coughing, and rarer side effects include rash, angioedema, hyperkalemia, and functional renal failure. $AT_1$ receptor antagonists are equally effective as ACE inhibitors but without the high prevalence of cough.

Neprilysin (neutral endopeptidase, EC 3.4.24.11) (NEP), is an endothelial membrane bound $Zn^{2+}$ metallopeptidase found in many tissues, including the brain, kidney, lungs, gastrointestinal tract, heart, and peripheral vasculature. NEP is responsible for the degradation and inactivation of a number of vasoactive peptides, such as circulating bradykinin and angiotensin peptides, as well as the natriuretic peptides, the latter of which have several effects including vasodilation and diuresis. Thus, NEP plays an important role in blood pressure homeostasis. NEP inhibitors have been studied as potential therapeutics, and include thiorphan, candoxatril, and candoxatrilat. In addition, compounds have also been designed that inhibit both NEP and ACE, and include omapatrilat, gempatrilat, and sampatrilat. Referred to as vasopeptidase inhibitors, this class of compounds are described in Robl et al. (1999) *Exp. Opin. Ther. Patents* 9(12): 1665-1677.

There may be an opportunity to increase anti-hypertensive efficacy when combining $AT_1$ receptor antagonism and NEP inhibition, as evidenced by $AT_1$ receptor antagonist/NEP inhibitor combinations described in WO 9213564 to Darrow et al (Schering Corporation); US20030144215 to Ksander et al.; Pu et al., Abstract presented at the Canadian Cardiovascular Congress (October 2004); Gardiner et al. (2006) JPET 319:340-348; and WO 2007/045663 (Novartis AG).

Recently, WO 2007/056546 (Novartis AG) has described complexes of an $AT_1$ receptor antagonist and a NEP inhibitor, where an $AT_1$ receptor antagonist compound is non-covalently bound to a NEP inhibitor compound, or where the antagonist compound is linked to the inhibitor compound by a cation.

In spite of the advances in the art, there remains a need for a highly efficacious monotherapy with multiple mechanisms of action leading to levels of blood pressure control that can currently only be achieved with combination therapy. Compounds having either $AT_1$ receptor antagonist or NEP inhibitory activity are known, but no single compound having both $AT_1$ receptor antagonist and NEP inhibitory activity has been reported. Thus, although various hypertensive agents are known, and administered in various combinations, it would be highly desirable to provide single compounds having both $AT_1$ receptor antagonist activity and NEP inhibition activity in the same molecule. Compounds possessing both of these activities are expected to be particularly useful as therapeutic agents since they would exhibit antihypertensive activity through two independent modes of action while having single molecule pharmacokinetics.

In addition, such dual-acting compounds are also expected to have utility to treat a variety of other diseases that can be treated by antagonizing the $AT_1$ receptor and/or inhibiting the NEP enzyme.

SUMMARY OF THE INVENTION

The present invention provides novel compounds that have been found to possess $AT_1$ receptor antagonist activity and neprilysin (NEP) enzyme inhibition activity. Accordingly, compounds of the invention are expected to be useful and advantageous as therapeutic agents for treating conditions such as hypertension and heart failure.

One aspect of the invention is directed to a compound of formula I:

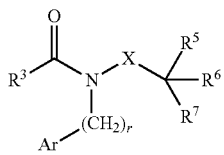

wherein:

r is 0, 1 or 2;

Ar is an aryl group selected from:

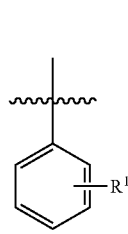 , 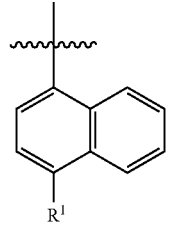 , 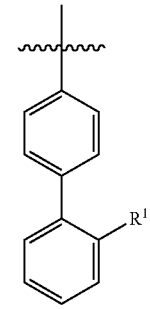 ,

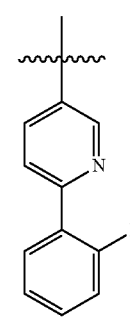 , 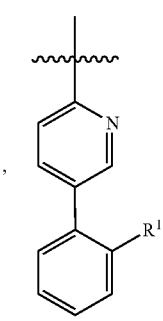 , 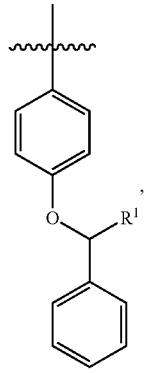 ,

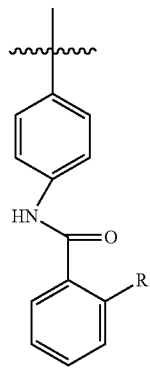 , 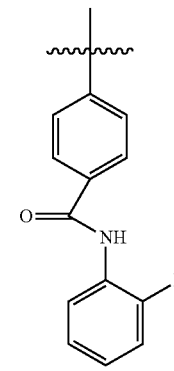 , 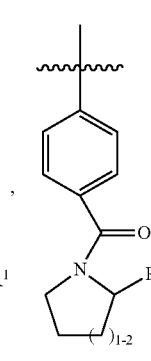 ,

-continued

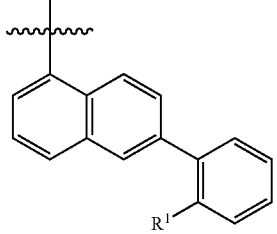 , 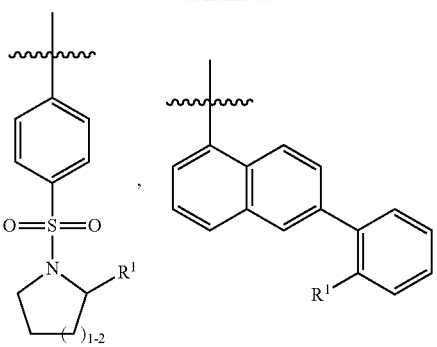 ,

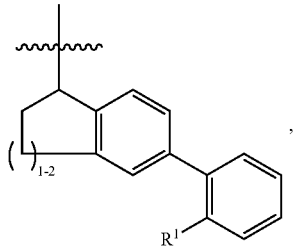 , 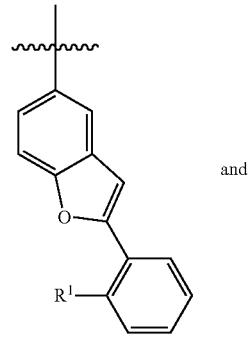 and

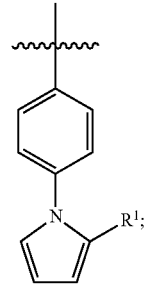 ;

$R^1$ is selected from —COOR$^{1a}$, —NHSO$_2$R$^{1b}$, —SO$_2$NHR$^{1d}$, —SO$_2$OH, —C(O)NH—SO$_2$R$^{1c}$, —P(O)(OH)$_2$, —CN, —O—CH(R$^{1e}$)—COOH, tetrazol-5-yl,

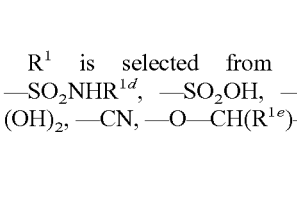 and ;

$R^{1a}$ is H, —C$_{1-6}$alkyl, —C$_{1-3}$alkylenearyl, —C$_{1-3}$alkyleneheteroaryl, —C$_{3-7}$cycloalkyl, —CH(C$_{1-4}$alkyl)OC(O)R$^{1aa}$, —C$_{0-6}$alkylenemorpholine,

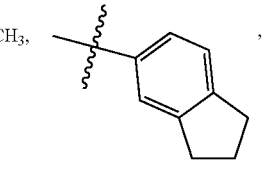 , or

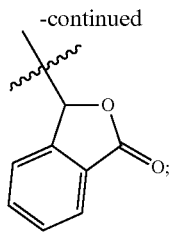

$R^{1aa}$ is —O—$C_{1-6}$alkyl, —O—$C_{3-7}$cycloalkyl, —NR$^{1ab}$R$^{1ac}$, or —CH(NH$_2$)CH$_2$COOCH$_3$; R$^{1ab}$ and R$^{1ac}$ are independently selected from H, —$C_{1-6}$alkyl, and benzyl, or are taken together as —(CH$_2$)$_{3-6}$—; R$^{1b}$ is R$^{1c}$ or —NHC(O)R$^{1c}$; R$^{1c}$ is —$C_{1-6}$alkyl, —$C_{0-6}$alkylene-O—R$^{1ca}$, —$C_{1-5}$alkylene-NR$^{1cb}$R$^{1cc}$, or —$C_{0-4}$alkylenearyl; R$^{1ca}$ is H, —$C_{1-6}$alkyl, or —$C_{1-6}$alkylene-O—$C_{1-6}$alkyl; R$^{1cb}$ and R$^{1cc}$ are independently selected from H and —$C_{1-6}$alkyl, or are taken together as —(CH$_2$)$_2$—O—(CH$_2$)$_2$— or —(CH$_2$)$_2$—N[C(O)CH$_3$]—(CH$_2$)$_2$—; R$^{1d}$ is H, R$^{1c}$, —C(O)R$^{1c}$, or —C(O)NHR$^{1c}$; R$^{1e}$ is —$C_{1-4}$alkyl or aryl;

R$^3$ is selected from —$C_{1-10}$alkyl, —$C_{2-10}$alkenyl, —$C_{3-10}$alkynyl, —$C_{0-3}$alkylene-$C_{3-7}$cycloalkyl, —$C_{2-3}$alkenylene-$C_{3-7}$cycloalkyl, —$C_{2-3}$alkynylene-$C_{3-7}$cycloalkyl, —$C_{0-5}$alkylene-NR$^{3a}$—$C_{0-5}$alkylene-R$^{3b}$, —$C_{0-5}$alkylene-O—$C_{0-5}$alkylene-R$^{3b}$, —$C_{1-5}$alkylene-S—$C_{1-5}$alkylene-R$^{3b}$, and —$C_{0-3}$alkylenearyl; R$^{1a}$ is H, —$C_{1-6}$alkyl, —$C_{3-7}$ cycloalkyl, or —$C_{0-3}$alkylenearyl; and R$^{3b}$ is H, —$C_{1-6}$alkyl, —$C_{3-7}$cycloalkyl, —$C_{2-4}$alkenyl, —$C_{2-4}$alkynyl, or aryl;

X is —$C_{1-12}$alkylene-, where at least one —CH$_2$— moiety in the alkylene is replaced with a —NR$^{4a}$—C(O)— or —C(O)—NR$^{4a}$— moiety, where R$^{4a}$ is selected from H, —OH, and —$C_{1-4}$alkyl;

R$^5$ is selected from —CO$_{0-3}$ alkylene-SR$^{5a}$, —$C_{0-3}$alkylene-C(O)NR$^{5b}$R$^{5c}$, —$C_{0-3}$alkylene-NR$^{5b}$—C(O)R$^{5d}$, —NH—$C_{0-1}$alkylene-P(O)(OR$^{5e}$)$_2$, —$C_{0-3}$alkylene-P(O)OR$^{5e}$R$^{5f}$, —$C_{0-2}$alkylene-CHR$^{5g}$—COOH and —$C_{0-3}$alkylene-C(O)NR$^{5b}$—CHR$^{5i}$—COOH; R$^{5a}$ is H or —C(O)—R$^{5aa}$; R$^{5aa}$ is —$C_{1-6}$alkyl, —$C_{0-6}$alkylene-$C_{3-7}$cycloalkyl, —$C_{0-6}$alkylenearyl, —$C_{0-6}$alkyleneheteroaryl, —$C_{0-6}$alkylenemorpholine, —$C_{0-6}$alkylenepiperazine-CH$_3$, —CH(NH$_2$)-aa where aa is an amino acid side chain, -2-pyrrolidine, —$C_{0-6}$alkylene-OR$^{5ab}$, —O—$C_{0-6}$alkylenearyl, —$C_{1-2}$alkylene-OC(O)—$C_{1-6}$alkyl, —$C_{1-2}$alkylene-OC(O)—$C_{0-6}$alkylenearyl, or —O—$C_{1-2}$alkylene-OC(O)O—$C_{1-6}$alkyl; R$^{5ab}$ is H or —$C_{1-6}$alkyl; R$^{5b}$ is H, —OH, —OC(O)R$^{5ba}$, —CH$_2$COOH, —O-benzyl, -pyridyl, or —OC(S)NR$^{5bb}$R$^{5bc}$; R$^{5ba}$ is —$C_{1-6}$alkyl, —OCH$_2$-aryl, —CH$_2$O-aryl, or —NR$^{5bb}$R$^{bc}$; R$^{5bb}$ and R$^{5bc}$ are independently selected from H and —$C_{1-4}$alkyl; R$^{5c}$ is H, —$C_{1-6}$alkyl, or —C(O)—R$^{5ca}$; R$^{5ca}$ is —$C_{1-6}$alkyl, —$C_{3-7}$cycloalkyl, aryl, or heteroaryl; R$^{5d}$ is H, —$C_{1-4}$alkyl, —$C_{0-3}$alkylenearyl, —NR$^{5da}$R$^{5db}$, —CH$_2$SH, or —O—$C_{1-6}$alkyl; R$^{5da}$ and R$^{5db}$ are independently selected from H and —$C_{1-4}$alkyl; R$^{5e}$ is H, —$C_{1-6}$alkyl, —$C_{1-3}$alkylenearyl, —$C_{1-3}$alkyleneheteroaryl, —$C_{3-7}$cycloalkyl, —CH(CH$_3$)—O—C(O)R$^{5ea}$,

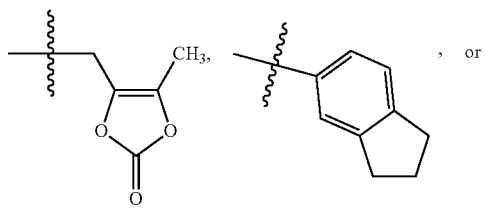

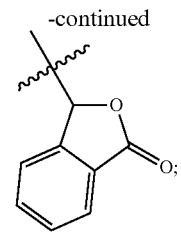

R$^{5ea}$ is —O—$C_{3-7}$cycloalkyl, —NR$^{5eb}$R$^{5ec}$, or —CH(NH$_2$)CH$_2$COOCH$_3$; R$^{5eb}$ and R$^{5ec}$ are independently selected from H, —$C_{1-4}$alkyl, and —$C_{1-3}$alkylenearyl, or are taken together as —(CH$_2$)$_{3-6}$—; R$^{5f}$ is H, —$C_{1-4}$alkyl, —$C_{0-3}$alkylenearyl, —$C_{1-3}$alkylene-NR$^{5fa}$R$^{5fb}$, or —$C_{1-3}$alkylene(aryl)-$C_{0-3}$alkylene-NR$^{5fa}$R$^{5fb}$; R$^{5fa}$ and R$^{5fb}$ are independently selected from H and —$C_{1-4}$alkyl; R$^{5g}$ is H, —$C_{1-6}$alkyl, —$C_{1-3}$ alkylenearyl, or —CH$_2$—O—(CH$_2$)$_2$—O—CH$_3$; R$^{5h}$ is H or —$C_{1-4}$alkyl; and R$^{5i}$ is H, —$C_{1-4}$alkyl, or —$C_{0-3}$alkylenearyl;

R$^6$ is selected from —$C_{1-6}$alkyl, —CH$_2$O(CH$_2$)$_2$—O—CH$_3$, —$C_{1-6}$alkylene-O—$C_{1-6}$alkyl, —$C_{0-3}$alkylenearyl, —$C_{0-3}$alkyleneheteroaryl, and —$C_{0-3}$alkylene-$C_{3-7}$cycloalkyl; and R$^7$ is H or is taken together with R$^6$ to form —$C_{3-8}$cycloalkyl;

wherein: each —CH$_2$— group in —(CH$_2$)$_r$— is optionally substituted with 1 or 2 substituents independently selected from —$C_{1-4}$alkyl and fluoro;

each carbon atom in X is optionally substituted with one or more R$^{4b}$ groups and one —CH$_2$— moiety in X may be replaced with a group selected from —$C_{4-8}$cycloalkylene-, —CR$^{4d}$═CH—, and —CH═CR$^{4d}$—; wherein R$^{4b}$ is selected from —$C_{0-5}$alkylene-COOR$^{4c}$, —$C_{1-6}$ alkyl, —$C_{0-1}$alkylene-CONH$_2$, —$C_{1-2}$alkylene-OH, —$C_{0-3}$alkylene-$C_{3-7}$cycloalkyl, 1H-indol-3-yl, benzyl, and hydroxybenzyl, where R$^{4c}$ is H or —$C_{1-4}$alkyl; and R$^{4d}$ is selected from —CH$_2$-thiophene and phenyl;

each alkyl and each aryl in R$^1$, R$^3$, R$^{4a-4d}$, and R$^{5-6}$ is optionally substituted with 1 to 7 fluoro atoms;

each ring in Ar and each aryl in R$^1$, R$^3$, and R$^{5-6}$ is optionally substituted with 1 to 3 substituents independently selected from —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —S(O)$_2$—$C_{1-4}$alkyl, -phenyl, —NO$_2$, —NH$_2$, —NH—$C_{1-6}$alkyl and —N($C_{1-6}$alkyl)$_2$, wherein each alkyl, alkenyl and alkynyl is optionally substituted with 1 to 5 fluoro atoms;

and pharmaceutically acceptable salts thereof.

Another aspect of the invention relates to pharmaceutical compositions comprising a pharmaceutically acceptable carrier and a compound of the invention. Such compositions may optionally contain other therapeutic active agents such as diuretics, β$_1$ adrenergic receptor blockers, calcium channel blockers, angiotensin-converting enzyme inhibitors, AT$_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, vasopressin receptor antagonists, and combinations thereof. Accordingly, in yet another aspect of the invention, a pharmaceutical composition comprises a compound of the invention, a second therapeutic agent, and a pharmaceutically acceptable carrier. Another aspect of the invention pertains to a combination of active agents, comprising a compound of the invention and a second therapeutic agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of the invention and a first pharmaceutically acceptable carrier; and a second pharmaceutical composition comprising a second therapeutic agent and a second pharmaceutically acceptable carrier. The invention also relates to a kit containing such pharmaceutical compositions, for example where the first and second pharmaceutical compositions are separate pharmaceutical compositions.

Compounds of the invention possess both $AT_1$ receptor antagonist activity and NEP enzyme inhibition activity, and are therefore expected to be useful as therapeutic agents for treating patients suffering from a disease or disorder that is treated by antagonizing the $AT_1$ receptor and/or inhibiting the NEP enzyme. Thus, one aspect of the invention is directed to a method of treating patients suffering from a disease or disorder that is treated by antagonizing the $AT_1$ receptor and/or inhibiting the NEP enzyme, comprising administering to a patient a therapeutically effective amount of a compound having both $AT_1$ receptor-antagonizing activity and NEP enzyme-inhibiting activity. Another aspect of the invention is directed to a method of treating hypertension or heart failure, comprising administering to a patient a therapeutically effective amount of a compound having both $AT_1$ receptor-antagonizing activity and NEP enzyme-inhibiting activity. In one aspect of these methods, the compound is a compound of formula I or a pharmaceutically acceptable salt thereof. Still another aspect of the invention pertains to a method for antagonizing an $AT_1$ receptor in a mammal comprising administering to the mammal, an $AT_1$ receptor-antagonizing amount of a compound of the invention. Yet another aspect of the invention pertains to a method for inhibiting a NEP enzyme in a mammal comprising administering to the mammal, a NEP enzyme-inhibiting amount of a compound of the invention.

Compounds having both $AT_1$ receptor-antagonizing activity and NEP enzyme-inhibiting activity, as well as the compounds of formula I and pharmaceutically acceptable salts thereof, that are of particular interest include those that exhibit an inhibitory constant ($pK_i$) for binding to an $AT_1$ receptor greater than or equal to about 5.0; in particular those having a $pK_i$ greater than or equal to about 6.0; in one embodiment those having a $pK_i$ greater than or equal to about 7.0; more particularly those having a $pK_i$ greater than or equal to about 8.0; and in yet another embodiment, those having a $pK_i$ within the range of about 8.0-10.0. Compounds of particular interest also include those having a NEP enzyme inhibitory concentration ($pIC_{50}$) greater than or equal to about 5.0; in one embodiment those having a $pIC_{50}$ greater than or equal to about 6.0; in particular those having a $pIC_{50}$ greater than or equal to about 7.0; and most particularly those having a $pIC_{50}$ within the range of about 7.0-10.0. Compounds of further interest include those having a $pK_i$ for binding to an $AT_1$ receptor greater than or equal to about 7.5 and having a NEP enzyme $pIC_{50}$ greater than or equal to about 7.0.

Since compounds of the invention possess $AT_1$ receptor antagonist activity and NEP inhibition activity, such compounds are also useful as research tools. Accordingly, one aspect of the invention pertains to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include an $AT_1$ receptor binding assay and a NEP enzyme inhibition assay. Still another aspect of the invention is directed to a method of studying a biological system or sample comprising an $AT_1$ receptor, a NEP enzyme, or both, the method comprising: (a) contacting the biological system or sample with a compound of the invention; and (b) determining the effects caused by the compound on the biological system or sample.

The invention is also directed to processes and intermediates useful for preparing compounds of the invention. Accordingly, another aspect of the invention relates to a process of preparing compounds of the invention. Another aspect of the invention relates to a process of preparing a pharmaceutically acceptable salt of a compound of formula I, comprising contacting a compound of formula I in free acid or base form with a pharmaceutically acceptable base or acid. In other aspects, the invention is directed to products prepared by any of the processes described herein, as well as novel intermediates used in such process. In one aspect of the invention, these novel intermediates have formula II, III or IV.

Yet another aspect of the invention is directed to the use of a compound having both $AT_1$ receptor-antagonizing activity and NEP enzyme-inhibiting activity for the manufacture of a medicament, especially for the manufacture of a medicament useful for treating hypertension or acute decompensated heart failure. In one aspect of these uses, the compound is a compound of formula I or a pharmaceutically acceptable salt thereof. Another aspect of the invention is directed to use of a compound of the invention for antagonizing an $AT_1$ receptor or for inhibiting a NEP enzyme in a mammal. Still another aspect of the invention pertains to the use of a compound of the invention as a research tool. Other aspects and embodiments of the invention are disclosed herein.

DETAILED DESCRIPTION OF THE INVENTION

The invention is directed to compounds of formula I:

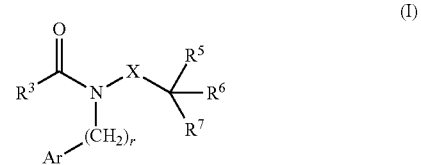

and pharmaceutically acceptable salts thereof.

As used herein, the term "compound of the invention" is intended to include compounds of formula I as well as the species embodied in formulas Ia, Ib, Ic, Id, and Ie. In addition, the compounds of the invention may also contain several basic or acidic groups (for example, amino or carboxyl groups) and therefore, such compounds can exist as a free base, free acid, or in various salt forms. All such salt forms are included within the scope of the invention. Furthermore, solvates of compounds of formula I or salts thereof are included within the scope of the invention. Finally, the compounds of the invention may also exist as prodrugs. Accordingly, those skilled in the art will recognize that reference to a compound herein, for example, reference to a "compound of the invention" includes reference to a compound of formula I as well as to pharmaceutically acceptable salts, solvates and prodrugs of that compound unless otherwise indicated. Further, the term "or a pharmaceutically acceptable salt, solvate and/or prodrug thereof" is intended to include all permutations of salts and solvates, such as a solvate of a pharmaceutically acceptable salt.

The compounds of formula I may contain one or more chiral centers and so may exist in a number of stereoisomeric forms. When such chiral centers are present, the invention is directed to racemic mixtures, pure stereoisomers (enantiomers or diastereomers), stereoisomer-enriched mixtures, and the like unless otherwise indicated. When a chemical structure is depicted without any stereochemistry, it is understood that all possible stereoisomers are encompassed by such structure. Thus, for example, the term "compound of formula I" is intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual enantiomers may be obtained by numerous methods that are well known in the art, including chiral chromatography using a suitable chiral stationary phase or support, or by chemically converting them into diastereomers, separating the diastereomers by conventional means such as chromatography or recrystallization, then regenerating the original enantiomers. Additionally, where applicable, all cis-trans or E/Z isomers (geometric isomers), tautomeric forms and topoisomeric forms of the compounds of the invention are included within the scope of the invention unless otherwise specified.

Compounds of formula I may contain one or more chiral centers. One possible chiral center could be present in the X portion of the compound. For example, a chiral center exists at a carbon atom in the alkylene moiety in X that is substituted with an $R^{4b}$ group such as —$C_{1-6}$alkyl, for example —$CH_3$. This chiral center is present at the carbon atom indicated by the symbol * in the following partial formula:

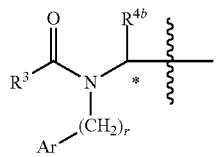

Another possible chiral center could be present in the —$CR^5R^6R^7$ portion of the compound, when $R^6$ is a group such as —$C_{1-6}$alkyl, for example —$CH_2CH(CH_3)_2$, and $R^7$ is H. This chiral center is present at the carbon atom indicated by the symbol ** in the following

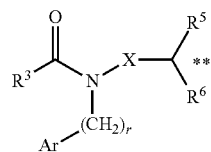

In one embodiment of the invention, the carbon atom identified by the symbol * and/or ** has the (R) configuration. In this embodiment, compounds of formula I have the (R) configuration at the carbon atom identified by the symbol * and/or ** or are enriched in a stereoisomeric form having the (R) configuration at this carbon atom (or atoms). In another embodiment, the carbon atom identified by the symbol * and/or ** has the (S) configuration. In this embodiment, compounds of formula I have the (S) configuration at the carbon atom identified by the symbol * and/or ** or are enriched in a stereoisomeric form having the (S) configuration at this carbon atom. It is understood that a compound may have a chiral center at both the * and the ** carbon atoms. In such cases, four possible diastereomers can exist. In some cases, in order to optimize the therapeutic activity of the compounds of the invention, for example, as hypertensive agents, it may be desirable that the carbon atom identified by the symbol * and/or ** have a particular (R) or (S) configuration.

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2H$, $^3H$, $^{13}C$, $^{14}C$, $^{15}N$, $^{18}O$, $^{17}O$, $^{35}S$, $^{36}Cl$, and $^{18}F$.

The compounds of formula I have been found to possess $AT_1$ receptor antagonizing activity and NEP enzyme inhibition activity. Among other properties, such compounds are expected to be useful as therapeutic agents for treating diseases such as hypertension. By combining dual activity into a single compound, double therapy can be achieved; both $AT_1$ receptor antagonist activity and NEP enzyme inhibition activity can be obtained using a single active component. Since pharmaceutical compositions containing one active component are typically easier to formulate than compositions containing two active components, such single-component compositions provide a significant advantage over compositions containing two active components. In addition, certain compounds of the invention have also been found to be selective for inhibition of the $AT_1$ receptor over the angiotensin II type 2 ($AT_2$) receptor, a property that may have therapeutic advantages.

The nomenclature used herein to name the compounds of the invention is illustrated in the Examples herein. This nomenclature has been derived using the commercially-available AutoNom software (MDL, San Leandro, Calif.).

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

The values for r are 0, 1 or 2. In one embodiment, r is 1. Each —$CH_2$— group in the —$(CH_2)_r$— group may be substituted with 1 or 2 substituents independently selected from —$C_{1-4}$alkyl (for example, —$CH_3$), and fluoro. In one particular embodiment, the —$(CH_2)_r$— group is unsubstituted; in another embodiment, one or two —$CH_2$— groups in —$(CH_2)_r$— are substituted with a —$C_{1-4}$alkyl group.

Ar represents an aryl group selected from:

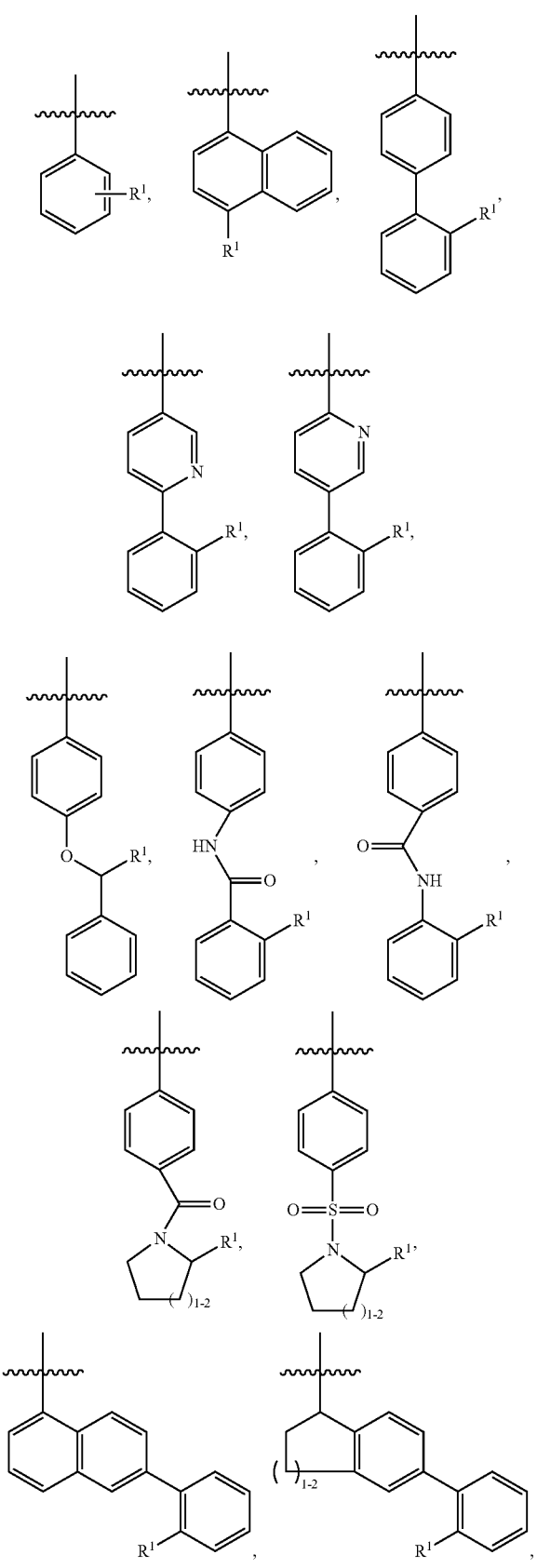

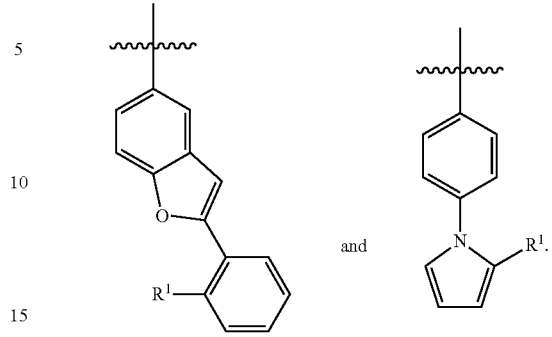

Each ring in the Ar moiety may be substituted with 1 to 3 substituents independently selected from —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —S(O)$_2$—$C_{1-4}$alkyl, -phenyl, —NO$_2$, —NH$_2$, —NH—$C_{1-6}$alkyl and —N($C_{1-6}$alkyl)$_2$. Furthermore, each of the aforementioned alkyl, alkenyl and alkynyl groups are optionally substituted with 1 to 5 fluoro atoms.

In one particular embodiment, each ring in the Ar moiety may be substituted with 1 to 2 substituents independently selected from —OH, —$C_{1-4}$alkyl (for example, —CH$_3$), halo (for example bromo, fluoro, chloro, and di-fluoro), —O—$C_{1-4}$ alkyl (for example, —OCH$_3$), and -phenyl. Exemplary substituted Ar moieties include:

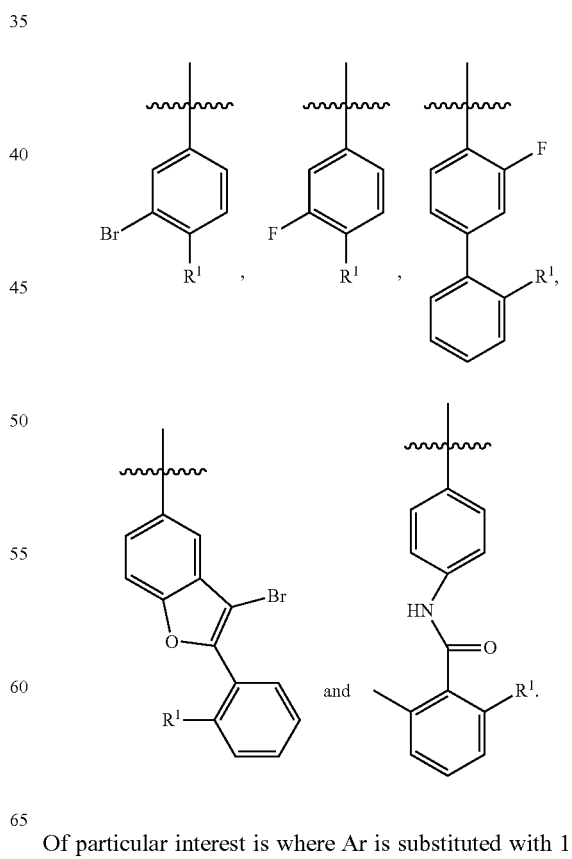

Of particular interest is where Ar is substituted with 1 or 2 halo atoms.

It is understood that:

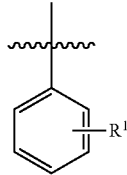

represents:

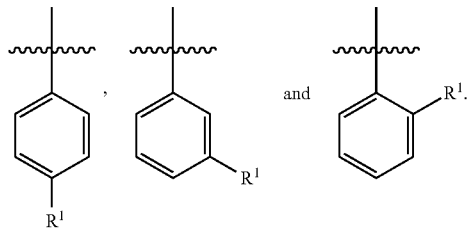

In one particular embodiment, Ar is an aryl group selected from:

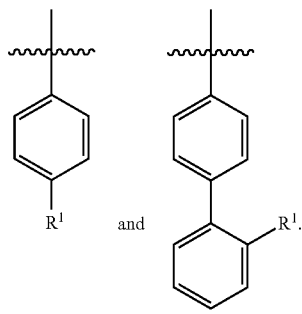

R¹ is selected from —COOR$^{1a}$, —NHSO$_2$R$^{1b}$, —SO$_2$NHR$^{1d}$, —SO$_2$OH, —C(O)NH—SO$_2$R$^{1c}$, —P(O)(OH)$_2$, —CN, —O—CH(R$^{1e}$)—COOH, tetrazol-5-yl,

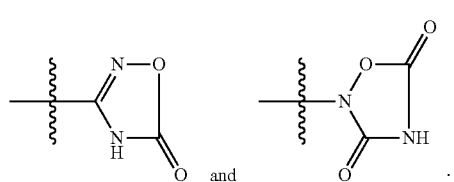

The R$^{1a}$ moiety is H, —C$_{1-6}$alkyl, —C$_{1-3}$alkylenearyl, —C$_{1-3}$alkyleneheteroaryl, —C$_{3-7}$cycloalkyl, —CH(C$_{1-4}$alkyl)OC(O)R$^{1aa}$, —C$_{0-6}$alkylenemorpholine,

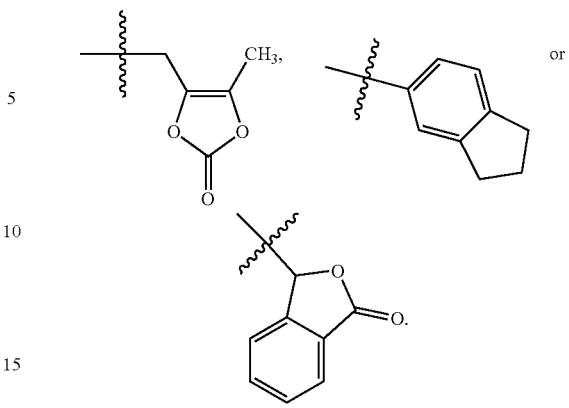

R$^{1aa}$ is —O—C$_{1-6}$alkyl, —O—C$_{3-7}$cycloalkyl, —NR$^{1ab}$R$^{1ac}$, or —CH(NH$_2$)CH$_2$COOCH$_3$. R$^{1ab}$ and R$^{1ac}$ are independently selected from H, —C$_{1-6}$alkyl, and benzyl, or are taken together as —(CH$_2$)$_{3-6}$—.

The R$^{1b}$ moiety is R$^{1c}$ or —NHC(O)R$^{1c}$. The R$^{1c}$ group is —C$_{1-6}$alkyl, —C$_{0-6}$alkylene-O—R$^{1ca}$, —C$_{1-5}$alkylene-NR$^{1cb}$R$^{1cc}$, or —C$_{0-4}$alkylenearyl. The R$^{1ca}$ moiety is H, —C$_{1-6}$alkyl, or —C$_{1-6}$alkylene-O—C$_{1-6}$alkyl. The R$^{1cb}$ and R$^{1cc}$ groups are independently selected from H and —C$_{1-6}$alkyl, or are taken together as —(CH$_2$)$_2$—O—(CH$_2$)$_2$— or —(CH$_2$)$_2$—N[C(O)CH$_3$]-(CH$_2$)$_2$—. The R$^{1d}$ moiety is H, R$^{1c}$, —C(O)R$^{1c}$, or —C(O)NHR$^{1c}$. The R$^{1e}$ group is C$_{1-4}$alkyl or aryl.

Each alkyl and each aryl in R$^1$ is optionally substituted with 1 to 7 fluoro atoms. In addition, the term "alkyl" is intended to include divalent alkylene groups such as those present in —C$_{1-3}$alkylenearyl and —C$_{1-3}$alkyleneheteroaryl, for example. Further, each aryl group that might be present in R$^1$, may be substituted with 1 to 3 —OH, —C$_{1-6}$alkyl, —C$_{2-4}$alkenyl, —C$_{2-4}$alkynyl, —CN, halo, —O—C$_{1-6}$alkyl, —S—C$_{1-6}$alkyl, —S(O)—C$_{1-6}$alkyl, —S(O)$_2$—C$_{1-4}$alkyl, -phenyl, —NO$_2$, —NH$_2$, —NH—C$_{1-6}$alkyl, or —N(C$_{1-6}$alkyl)$_2$ groups. Further, each of the aforementioned alkyl, alkenyl and alkynyl groups may be substituted with 1 to 5 fluoro atoms. It is understood that when referring to "each alkyl" and "each aryl" group in R$^1$, the terms also include any alkyl and aryl groups that might be present in the R$^{1a}$ through R$^{1e}$ moieties.

In one embodiment, R$^1$ is —COOR$^{1a}$ and R$^{1a}$ is H. In another embodiment, R$^1$ is —COOR$^{1a}$ and R$^{1a}$ is —C$_{1-6}$alkyl, examples of which include —CH$_3$, —CH$_2$CH$_3$, —(CH$_2$)$_2$CH$_3$, —(CH$_2$)$_2$—CF$_3$, —CH$_2$CH(CH$_3$)$_2$, —CH(CH$_3$)$_2$, —CH(CH$_3$)—CF$_3$, —CH(CH$_2$F)$_2$, —C(CH$_3$)$_3$, —(CH$_2$)$_3$CH$_3$, and —(CH$_2$)$_2$—CF$_2$CF$_3$. Thus, examples of R$^1$ include —C(O)OCH$_3$, —COOCH$_2$CH$_3$, and so forth.

In one embodiment, R$^1$ is —COOR$^{1a}$ and R$^{1a}$ is —C$_{1-3}$alkylenearyl, for example, a benzyl group, which may be substituted such as chlorobenzyl, fluorobenzyl, difluorobenzyl, -benzyl-CH$_3$, -benzyl-CF$_3$, and -benzyl-O—CF$_3$. Thus, examples of R$^1$ include: —C(O)OCH$_2$-benzyl,

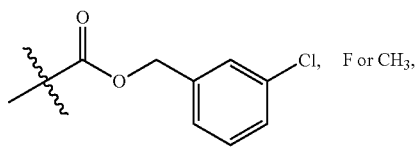

Cl, F or CH$_3$,

-continued

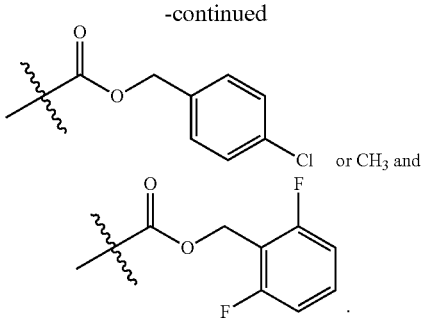

or CH₃ and

In one embodiment, R¹ is —COOR$^{1a}$ and R$^{1a}$ is —C$_{1-3}$alkyleneheteroaryl, examples of which include —CH$_2$-pyridinyl. In one embodiment, R¹ is —COOR$^{1a}$ and R$^{1a}$ is —C$_{3-7}$cycloalkyl, examples of which include cyclopentyl.

In yet another embodiment R¹ is —COOR$^{1a}$ and R$^{1a}$ is —CH(C$_{1-4}$alkyl)OC(O)R$^{1aa}$, where R$^{1aa}$ is —O—C$_{1-6}$alkyl, —O—C$_{3-7}$cycloalkyl, —NR$^{1ab}$R$^{1ac}$, or —CH(NH$_2$)CH$_2$COOCH$_3$. R$^{1ab}$ and R$^{1ac}$ are independently selected from H, —C$_{1-6}$alkyl, and benzyl, or are taken together as —(CH$_2$)$_{3-6}$—. Examples of —O—C$_{1-6}$alkyl groups include —O—CH$_2$CH$_3$ and —O—CH(CH$_3$)$_2$. Exemplary —O—C$_{3-7}$ cycloalkyl groups include —O-cyclohexyl. Thus, examples of R¹ include —C(O)OCH(CH$_3$)OC(O)—O—CH$_2$CH$_3$, —C(O)OCH(CH$_3$)OC(O)—O—CH(CH$_3$)$_2$, and —C(O)OCH(CH$_3$)OC(O)—O-cyclohexyl.

In one embodiment, R¹ is —COOR$^{1a}$ and R$^{1a}$ is —C$_{0-6}$alkylenemorpholine, examples of which include —(CH$_2$)$_2$-morpholine and —(CH$_2$)$_3$-morpholine. In another embodiment, R$^{1a}$ is

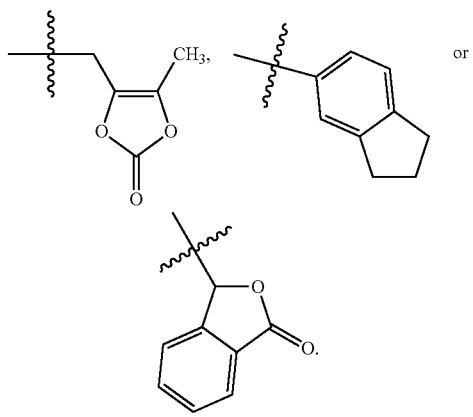

In one embodiment, R¹ is —NHSO$_2$R$^{1b}$ and R$^{1b}$ is R$^{1c}$. The R$^{1c}$ group is —C$_{1-6}$alkyl, —C$_{0-6}$alkylene-O—R$^{1ca}$, —C$_{1-5}$alkylene-NR$^{1cb}$R$^{1cc}$, or —C$_{0-4}$alkylenearyl. The R$^{1ca}$ moiety is H, —C$_{1-6}$alkyl, or —C$_{1-6}$alkylene-O—C$_{1-6}$alkyl. The R$^{1cb}$ and R$^{1cc}$ groups are independently selected from H and —C$_{1-6}$ alkyl, or are taken together as —(CH$_2$)$_2$—O—(CH$_2$)$_2$— or —(CH$_2$)$_2$—N[C(O)CH$_3$]-(CH$_2$)$_2$—. In one embodiment, R$^{1c}$ is —C$_{1-6}$alkyl, such that exemplary R¹ groups include —NHSO$_2$—CH$_3$ and the fluoro-substituted group, —NHSO$_2$—CF$_3$. In another embodiment, R$^{1c}$ is –C$_{0-4}$alkylenearyl, such that exemplary R¹ groups include —NHSO$_2$-phenyl.

In another embodiment, R¹ is —NHSO$_2$R$^{1b}$ and R$^{1b}$ is —NHC(O)R$^{1c}$, where R$^{1c}$ is defined above. In a particular embodiment, R¹ is —NHSO$_2$R$^{1b}$, R$^{1b}$ is —NHC(O)R$^{1c}$, and R$^{1c}$ is —C$_{1-6}$alkyl or —C$_{0-4}$alkylenearyl.

In one embodiment, R¹ is —SO$_2$NHR$^{1d}$ and R$^{1d}$ is H. In another embodiment, R¹ is —SO$_2$NHR$^{1d}$ and R$^{1d}$ is R$^{1c}$, where R$^{1c}$ is defined above. In a particular embodiment, R$^{1c}$ is —C$_{1-6}$alkyl or —C$_{0-4}$alkylenearyl. When R$^{1c}$ is —C$_{1-6}$alkyl, exemplary R¹ groups include the fluoro-substituted groups —SO$_2$NH—CF$_3$, —SO$_2$NH—CHF$_2$, —SO$_2$NH—CF$_2$CH$_2$F and —SO$_2$NH—CF$_2$CF$_2$CF$_3$.

In another embodiment, R¹ is —SO$_2$NHR$^{1d}$ and R$^{1d}$ is —C(O)R$^{1c}$, where R$^{1c}$ is defined above. In one embodiment of particular interest, R$^{1c}$ is —C$_{1-6}$alkyl or —C$_{0-4}$alkylenearyl. When R$^{1c}$ is —C$_{1-6}$alkyl, exemplary R¹ groups include —SO$_2$NHC(O)CH$_3$ and —SO$_2$NHC(O)(CH$_2$)$_2$CH$_3$. When R$^{1c}$ is —C$_{0-6}$alkylene-O—R$^{1ca}$ and R$^{1ca}$ is H, exemplary R¹ groups include —SO$_2$NHC(O)CH$_2$OH, —SO$_2$NHC(O)CH(CH$_3$)OH, and —SO$_2$NHC(O)C(CH$_3$)$_2$OH. When R$^{1c}$ is —C$_{0-6}$alkylene-O—R$^{1ca}$ and R$^{1ca}$ is —C$_{1-6}$alkyl, exemplary R¹ groups include —SO$_2$NHC(O)CH$_2$—O—CH$_3$ and —SO$_2$NHC(O)—O—CH$_2$CH$_3$. When R$^{1c}$ is —C$_{0-6}$alkylene-O—R$^{1ca}$ and R$^{1ca}$ is —C$_{1-6}$alkylene-O—C$_{1-6}$alkyl, exemplary R¹ groups include —SO$_2$NHC(O)CH$_2$—O—(CH$_2$)$_2$—O—CH$_3$. When R$^{1c}$ is —C$_{1-5}$alkylene-NR$^{1cb}$R$^{1cc}$ is exemplary R¹ groups include —SO$_2$NHC(O)CH$_2$N(CH$_3$)$_2$, —SO$_2$NHC(O)—CH$_2$—NH$_2$, and —SO$_2$NHC(O)—CH(CH$_3$)—NH$_2$. Another example when R$^{1c}$ is —C$_{1-5}$alkylene-NR$^{1cb}$R$^{1cc}$ is where the R$^{1cb}$ and R$^{1cc}$ are taken together as —(CH$_2$)$_2$—O—(CH$_2$)$_2$— or —(CH$_2$)$_2$—N[C(O)CH$_3$]—(CH$_2$)$_2$—. Such exemplary R¹ groups include:

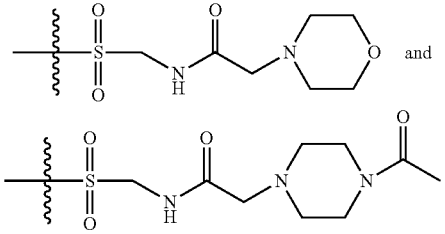

In another embodiment, R¹ is —SO$_2$NHR$^{1d}$ and R$^{1d}$ is —C(O)NHR$^{1c}$, where R$^{1c}$ is defined above. In a particular embodiment, R$^{1c}$ is —C$_{1-6}$alkyl or —C$_{0-4}$alkylenearyl. When R$^{1c}$ is —C$_{1-6}$alkyl, exemplary R¹ groups include —SO$_2$NHC(O)NH—CH$_2$CH$_3$ and —SO$_2$NHC(O)NH—(CH$_2$)$_2$CH$_3$. When R$^{1c}$ is —C$_{0-4}$alkylenearyl, exemplary R¹ groups include —SO$_2$NHC(O)NH-phenyl.

In another embodiment, R¹ is —SO$_2$OH, and in still another embodiment, R¹ is —P(O)(OH)$_2$. In yet another embodiment, R¹ is —CN.

In another embodiment, R¹ is —C(O)NH—SO$_2$R$^{1c}$, where R$^{1c}$ is defined above. In a particular embodiment, R$^{1c}$ is —C$_{1-6}$ alkyl or —C$_{0-4}$alkylenearyl. When R$^{1c}$ is —C$_{1-6}$alkyl, exemplary R¹ groups include —C(O)—NH—SO$_2$—CH$_3$, —C(O)—NH—SO$_2$—CH$_2$CH$_3$ and the fluoro-substituted —C(O)—NH—SO$_2$—CF$_3$ group.

In another embodiment, R¹ is —O—CH(R$^{1e}$)—COOH, where R$^{1e}$ is —C$_{1-4}$alkyl or aryl. Examples of such R¹ groups include, —O—CH(CH$_3$)—COOH and —O—CH(phenyl)-COOH.

In an embodiment of particular interest, R¹ is tetrazol-5-yl. In another embodiment, R¹ is:

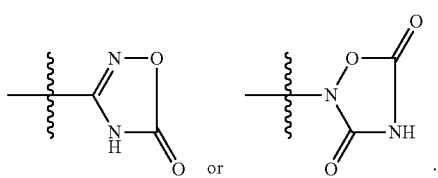 [SMILES: *c1noc(=O)[nH]1 ; "or" ; *n1oc(=O)[nH]c1=O ; "."]

In one particular embodiment, $R^1$ is —COOR$^{1a}$, where $R^{1a}$ is —C$_{1-6}$alkyl, —C$_{1-3}$alkylenearyl, —C$_{1-3}$alkyleneheteroaryl, —C$_{3-7}$cycloalkyl, —CH(C$_{1-4}$alkyl)OC(O)R$^{1aa}$, —C$_{0-6}$alkylenemorpholine,

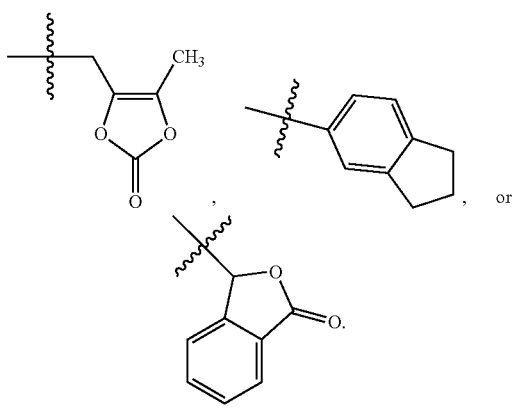

In one aspect of the invention, these compounds may find particular utility as prodrugs or as intermediates in the synthetic procedures described herein. In one particular embodiment, $R^1$ is —COOR$^{1a}$ and $R^{1a}$ is —C$_{1-6}$alkyl.

In another particular embodiment, $R^1$ is selected from —COOR$^{1a}$ where $R^{1a}$ is H, —NHSO$_2$R$^{1b}$, —SO$_2$NHR$^{1d}$, —SO$_2$OH, —C(O)NH—SO$_2$R$^{1c}$, —P(O)(OH)$_2$, —CN, —O—CH(R$^{1c}$)—COOH, tetrazol-5-yl,

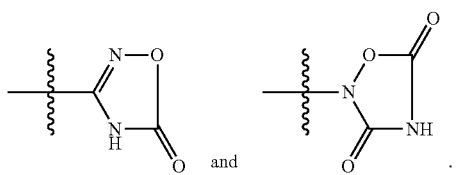 [SMILES: *c1noc(=O)[nH]1 ; *n1oc(=O)[nH]c1=O]

In one particular embodiment, $R^1$ is selected from —COOR$^{1a}$, —SO$_2$NHR$^{1d}$, and tetrazol-5-yl. In another embodiment, $R^1$ is selected from —COOH, —SO$_2$NHC(O)—C$_{1-6}$alkyl, and tetrazol-5-yl.

$R^3$ is selected from —C$_{1-10}$alkyl, —C$_{2-10}$alkenyl, —C$_{3-10}$ alkynyl, —C$_{0-3}$alkylene-C$_{3-7}$cycloalkyl, —C$_{2-3}$alkenylene-C$_{3-7}$cycloalkyl, —C$_{2-3}$alkynylene-C$_{3-7}$cycloalkyl, —C$_{0-5}$alkylene-NR$^{3a}$—C$_{0-5}$alkylene-R$^{3b}$, —C$_{0-5}$alkylene-O—C$_{0-5}$alkylene-R$^{3b}$, —C$_{1-5}$alkylene-S—C$_{1-5}$alkylene-R$^{3b}$, and —C$_{0-3}$alkylenearyl. The $R^{3a}$ moiety is H, —C$_{1-6}$ alkyl, —C$_{3-7}$ cycloalkyl, or —C$_{0-3}$alkylenearyl (for example, —C$_{0-1}$ alkylenearyl such as phenyl and benzyl). $R^{3b}$ is selected from H, —C$_{1-6}$alkyl, —C$_{3-7}$cycloalkyl, —C$_{2-4}$alkenyl, —C$_{2-4}$ alkynyl, and aryl (such as phenyl).

In addition, each alkyl and each aryl in $R^3$ is optionally substituted with 1 to 7 fluoro atoms, where the term "alkyl" is intended to include divalent alkylene groups such as those present in —C$_{0-3}$alkylene-C$_{3-7}$cycloalkyl and —C$_{0-3}$alkylenearyl, for example. Each aryl in $R^3$, for example in —C$_{0-3}$alkylenearyl or aryl, may be substituted with 1 to 3 —OH, —C$_{1-6}$alkyl, —C$_{2-4}$alkenyl, —C$_{2-4}$alkynyl, —CN, halo, —O—C$_{1-6}$alkyl, —S—C$_{1-6}$alkyl, —S(O)—C$_{1-6}$alkyl, —S(O)$_2$—C$_{1-4}$alkyl, -phenyl, —NO$_2$, —NH$_2$, —NH—C$_{1-6}$ alkyl, or —N(C$_{1-6}$alkyl)$_2$ groups. Further, each of the aforementioned alkyl, alkenyl and alkynyl groups may be substituted with 1 to 5 fluoro atoms. It is understood that when referring to "each alkyl" and "each aryl" group in $R^3$, the terms also include any alkyl and aryl groups that might be present in the $R^{3a}$ and $R^{3b}$ moieties.

In one embodiment, $R^3$ is —C$_{1-10}$alkyl such as —CH$_3$ or optionally substituted with 1 to 7 fluoro atoms such as —CF$_3$. In another embodiment, $R^3$ is —C$_{2-7}$alkyl such as —CH$_2$CH$_3$; and in yet another embodiment, $R^3$ is —C$_{2-5}$ alkyl, for example, —(CH$_2$)$_2$CH$_3$, —(CH$_2$)$_3$CH$_3$, —CH$_2$—CH(CH$_3$)$_2$, —CH$_2$—CH(CH$_3$)CH$_2$CH$_3$, —(CH$_2$)$_2$—CH(CH$_3$)$_2$, —CH(CH$_2$CH$_3$)$_2$, or —(CH$_2$)$_4$CH$_3$.

In another embodiment, $R^3$ is —C$_{2-10}$alkenyl such as —CH$_2$CH═CHCH$_3$. In yet another embodiment, $R^3$ is —C$_{3-10}$ alkynyl such as —CH$_2$C≡CCH$_3$.

In another embodiment, $R^3$ is —C$_{0-3}$alkylene-C$_{3-7}$cycloalkyl such as -cyclopropyl, —CH$_2$-cyclopropyl, cyclopentyl, —CH$_2$-cyclopentyl, —(CH$_2$)$_2$-cyclopentyl, and —CH$_2$-cyclohexyl. In a particular embodiment, $R^3$ is —C$_{0-1}$ alkylene-C$_{3-5}$cycloalkyl. In one embodiment, $R^3$ is —C$_{2-3}$ alkenylene-C$_{3-7}$cycloalkyl such as —CH$_2$CH═CH-cyclopentyl; and in another embodiment, $R^3$ is —C$_{2-3}$alkynylene-C$_{3-7}$cycloalkyl such as —CH$_2$C≡C-cyclopentyl.

In yet another embodiment, $R^3$ is —C$_{0-5}$alkylene-NR$^{3a}$—C$_{0-5}$alkylene-R$^{3b}$. In one particular embodiment, $R^{1a}$ is H and $R^{3b}$ is —C$_{1-6}$alkyl. Examples of such $R^3$ groups include —NHCH$_2$CH$_3$, —NHCH(CH$_3$)$_2$, —NH(CH$_2$)$_2$CH$_3$, —NH(CH$_2$)$_3$CH$_3$, —NHCH(CH$_3$)CH$_2$CH$_3$, —NH(CH$_2$)$_4$CH$_3$, and —NH(CH$_2$)$_5$CH$_3$.

In one embodiment, $R^3$ is —C$_{0-5}$alkylene-O—C$_{0-5}$alkylene-R$^{3b}$. In one particular embodiment, $R^{3b}$ is selected from H, —C$_{1-6}$alkyl and aryl. Examples of such $R^3$ groups include —OCH$_3$, —OCH$_2$CH$_3$, —OCH(CH$_3$)$_2$, —O(CH$_2$)$_2$CH$_3$, —O(CH$_2$)$_3$CH$_3$, —OCH$_2$CH(CH$_3$)$_2$, —O-phenyl, and —O-benzyl.

In another embodiment, $R^3$ is —C$_{1-5}$alkylene-S—C$_{1-5}$ alkylene-R$^{3b}$, and in one particular embodiment $R^{3b}$ is H, such as when $R^3$ is —CH$_2$—S—CH$_2$CH$_3$. In another embodiment, $R^3$ is —C$_{0-3}$alkylenearyl, such as phenyl, benzyl, and —(CH$_2$)$_2$-phenyl.

X is —C$_{1-12}$alkylene-, where at least one —CH$_2$— moiety in the alkylene is replaced with a —NR$^{4a}$—C(O)— or —C(O)—NR$^{4a}$— moiety. Thus X can be —C$_1$alkylene-, —C$_1$alkylene-, —C$_2$alkylene-, —C$_3$alkylene-, —C$_4$alkylene-, —C$_5$alkylene-, —C$_6$alkylene-, —C$_7$alkylene-, —C$_8$alkylene, —C$_9$alkylene-, —C$_{10}$alkylene-, —C$_{11}$alkylene-, and —C$_{12}$alkylene-, with at least one —CH$_2$— moiety being replaced. $R^{4a}$ is selected from H, —OH, and —C$_{1-4}$alkyl. In one embodiment, $R^{4a}$ is H.

Each carbon atom in the —C$_{1-12}$alkylene- group may be substituted with one or more R$^{4b}$ groups. R$^{4b}$ is selected from —C$_{0-5}$alkylene-COOR$^{4c}$, —C$_{1-6}$alkyl, —C$_{0-1}$alkylene-CONH$_2$, —C$_{1-2}$alkylene-OH, —C$_{0-3}$alkylene-C$_{3-7}$cycloalkyl, 1H-indol-3-yl, benzyl, and hydroxybenzyl, where $R^{4c}$ is H or —C$_{1-4}$alkyl. In one embodiment, the carbon atoms in —C$_{1-12}$alkylene- are unsubstituted with R$^{ab}$ groups. In another embodiment, 1 or 2 carbon atoms are substituted with one or two R$^{ab}$ groups. In another embodiment, one carbon atom is substituted with one R$^{4b}$ group. In one particular embodiment, $R^{4b}$ is —COOH, benzyl, or —$C_{1-6}$alkyl, including —$C_{1-3}$alkyl groups such as —$CH_3$ and —$CH(CH_3)_2$.

In addition, one —$CH_2$— moiety in X may be replaced with a group selected from —$C_{4-8}$cycloalkylene-, —$CR^{4d}$=CH—, and —CH=$CR^{4d}$—. $R^{4d}$ is selected from —$CH_2$-thiophene and phenyl. In one embodiment, none of the —$CH_2$— moieties are so replaced. In another embodiment, one —$CH_2$— moiety is replaced with —$C_{4-8}$cycloalkylene-, for example, cyclohexylene. In another embodiment, one —$CH_2$— moiety is replaced with —CH=$CR^{4d}$—, where $R^{4d}$ is —$CH_2$-thiophene such as —$CH_2$-thiophen-2-yl.

Each alkyl and each aryl in $R^{4a}$, $R^{4b}$, $R^{4c}$, and $R^{4d}$, may be substituted with 1 to 7 fluoro atoms, and the term "alkyl" is intended to include divalent alkylene groups such as that present in —$C_{0-5}$alkylene-$COOR^{4c}$, for example. It is noted that the $R^{4b}$ group, —$C_{0-3}$alkylene-$C_{3-7}$cycloalkyl, is intended to include a $C_{3-7}$cycloalkyl linked to the X —$C_{1-12}$alkylene- chain by a bond as well as a $C_{3-7}$cycloalkyl that is directly attached to the

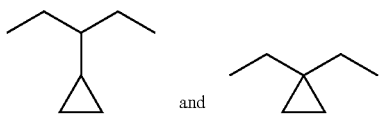

and

In one embodiment, one to four —$CH_2$— moieties are replaced with —$NR^{4a}$—C(O)— or —C(O)—$NR^{4a}$— moieties, in another embodiment one —$CH_2$— moiety is replaced, one example of which includes —$(CH_2)_2$—NHC(O)—. In one embodiment, X is —$C_{2-11}$alkylene- and 1, 2, or 3-$CH_2$— moieties are replaced with a —$NR^{4a}$—C(O)— or —C(O)—$NR^{4a}$— moiety. In another embodiment, X is —$C_{2-5}$alkylene-, where 1 or 2 —$CH_2$— moieties are replaced. When more than one —$CH_2$— moiety in —$C_{1-12}$alkylene- is replaced with a —$NR^{4a}$—C(O)— or —C(O)—$NR^{4a}$— moiety, the replaced moieties may be contiguous or non-contiguous. In one particular embodiment, the replaced moieties are contiguous. Exemplary X groups include the following, which depict: examples where one or more —$CH_2$— moieties are replaced with —$NR^{4a}$—C(O)— or —C(O)—$NR^{4a}$— moieties; examples where —$CH_2$— moieties are replaced with a group selected from —$C_{4-8}$cycloalkylene-, —$CR^{4d}$=CH—, and —CH=$CR^{4d}$—; and examples where carbon atoms in the —$C_{1-12}$alkylene- group are substituted with one or more $R^{4b}$ groups:

—$C_1$alkylene- with one —$CH_2$— moiety replaced:
—C(O)NH—
—NHC(O)—
—$C_2$alkylene- with one —$CH_2$— moiety replaced:
—$CH_2$—NHC(O)—
—C(O)NH—$CH_2$—
—$CH_2$—C(O)NH—
—CH[CH(CH$_3$)$_2$]—C(O)NH—
—CH(COOH)—NHC(O)—
—$C_2$alkylene- with two —$CH_2$— moieties replaced:
—C(O)NH—NHC(O)—
—CH=C(—$CH_2$-thiopheny-2-yl)-C(O)NH—
—$C_3$alkylene- with one —$CH_2$— moiety replaced:
—$(CH_2)_2$—NHC(O)—
—$(CH_2)_2$—C(O)NH—
—CH(CH$_3$)—$CH_2$—NHC(O)—
—CH[CH(CH$_3$)$_2$]—$CH_2$—NHC(O)—
—CH(COOH)—$CH_2$—NHC(O)—
—$CH_2$—CH(COOH)—NHC(O)—
—$CH_2$—C(CH$_3$)$_2$—NHC(O)—
—$C_3$alkylene- with two —$CH_2$— moieties replaced:
—NHC(O)—$CH_2$—NHC(O)—
—$C_4$alkylene- with one —$CH_2$— moiety replaced:
—$(CH_2)_3$—NHC(O)—
—C(O)NH—$CH_2$—CH(COOH)—$CH_2$
—$C_4$alkylene- with two —$CH_2$— moieties replaced:
—C(O)NH—CH(benzyl)-$CH_2$—NHC(O)—
—C(O)NH—CH(benzyl)-$CH_2$—C(O)NH—
—$CH_2$—NHC(O)—$CH_2$—NHC(O)—
—$C_4$alkylene- with three —$CH_2$— moieties replaced:
—$CH_2$—NHC(O)-cyclohexylene-NHC(O)—
—$CH_2$—N(OH)C(O)-cyclohexylene-NHC(O)—
—$C_5$alkylene- with two —$CH_2$— moieties replaced:
—$CH_2$—NHC(O)—$CH_2$—CH(COOH)—NHC(O)—
—$CH_2$—NHC(O)—$(CH_2)_2$—NHC(O)—
—C(O)NH—$(CH_2)_2$—C(O)N(OH)—$CH_2$
—C(O)NH—$(CH_2)_2$—CH(COOH)—NHC(O)—
—CH(COOH)—$CH_2$—NHC(O)—$CH_2$—NHC(O)—
—$(CH_2)_2$—NHC(O)-cyclohexylene-NHC(O)—
—$CH_2$—CH(COOH)—NHC(O)—$CH_2$—NHC(O)—
—$C_6$alkylene- with two —$CH_2$— moieties replaced:
—C(O)NH—$(CH_2)_4$—NHC(O)—
—$CH_2$—NHC(O)—$(CH_2)_2$—CH(COOH)—NHC(O)—
—C(O)NH—$(CH_2)_3$—CH(COOH)—NHC(O)—
—$C_6$alkylene- with three —$CH_2$— moieties replaced:
—C(O)NH—$(CH_2)_2$—NHC(O)—$CH_2$—NHC(O)—
—$C_6$alkylene- with four —$CH_2$— moieties replaced:
—C(O)NH—$(CH_2)_2$—NHC(O)-cyclohexylene-NHC(O)—
—$C_7$alkylene- with two —$CH_2$— moieties replaced:
—$CH_2$—NHC(O)—$(CH_2)_4$—NHC(O)—
—C(O)NH—$(CH_2)_4$—CH(COOH)—NHC(O)—
—$C_7$alkylene- with three —$CH_2$— moieties replaced:
—CH[CH(CH$_3$)$_2$]—C(O)NH—$(CH_2)_2$—NHC(O)—$CH_2$—NHC(O)—
—$C_7$alkylene- with four —$CH_2$— moieties replaced:
—$CH_2$—NHC(O)—$(CH_2)_2$—NHC(O)-cyclohexylene-NHC(O)—
—$CH_2$—C(O)NH—$(CH_2)_2$—NHC(O)-cyclohexylene-NHC(O)—
—$C_8$alkylene- with three —$CH_2$— moieties replaced:
—C(O)NH—$(CH_2)_4$—NHC(O)—$CH_2$—NHC(O)—
$C_9$alkylene- with four —$CH_2$— moieties replaced:
—C(O)NH—$(CH_2)_4$—NHC(O)-cyclohexylene-NHC(O)—
—$C_9$alkylene- with two —$CH_2$— moieties replaced:
—$CH_2$—NHC(O)—$(CH_2)_6$—NHC(O)—
—$C_9$alkylene- with four —$CH_2$— moieties replaced:
—$CH_2$—NHC(O)—$(CH_2)_4$—NHC(O)-cyclohexylene-NHC(O)—
—$C_{10}$alkylene- with four —$CH_2$— moieties replaced:
—C(O)NH—$(CH_2)_6$—NHC(O)-cyclohexylene-NHC(O)—
—$C_{11}$alkylene- with three —$CH_2$— moieties replaced:
—CH[CH(CH$_3$)$_2$]—C(O)NH—$(CH_2)_6$—NHC(O)—$CH_2$—NHC(O)—
—$C_{11}$alkylene- with four —$CH_2$— moieties replaced:
—$CH_2$—NHC(O)—$(CH_2)_6$—NHC(O)-cyclohexylene-NHC(O)—

In one particular embodiment, X is —$(CH_2)_2$—NHC(O)— or —$(CH_2)_2$—C(O)NH—.

$R^5$ is selected from —$C_{0-3}$alkylene-$SR^{5a}$, —$C_{0-3}$alkylene-C(O)$NR^{5b}R^{5c}$, —$C_{0-3}$alkylene-$NR^{5b}$—C(O)$R^{5d}$, —NH—$C_{0-1}$alkylene-P(O)(O$R^{5e}$)$_2$, —$C_{0-3}$alkylene-P(O)O$R^{5e}R^{5f}$, —$C_{0-2}$alkylene-CHR$^{5g}$—COOH and —$C_{0-3}$alkylene-C(O)$NR^{5b}$—CHR$^{5i}$—COOH. Each alkyl and each aryl in $R^5$ is optionally substituted with 1 to 7 fluoro atoms, where the term "alkyl" is intended to include divalent alkylene groups such as those present in —C$_{0-3}$alkylene-SR$^{5a}$ and —C$_{0-3}$alkylene-P(O)OR$^{5e}$R$^{5f}$, for example. Each aryl in R$^5$ may be substituted with 1 to 3 —OH, —C$_{1-6}$alkyl, —C$_{2-4}$alkenyl, —C$_{2-4}$alkynyl, —CN, halo, —O—C$_{1-6}$alkyl, —S—C$_{1-6}$alkyl, —S(O)—C$_{1-6}$alkyl, —S(O)$_2$—C$_{1-4}$alkyl, -phenyl, —NO$_2$, —NH$_2$, —NH—C$_{1-6}$alkyl, or —N(C$_{1-6}$alkyl)$_2$ groups. Further, each of the aforementioned alkyl, alkenyl and alkynyl groups may be substituted with 1 to 5 fluoro atoms. It is understood that when referring to "each alkyl" and "each aryl" group in R$^5$, the terms also include any alkyl and aryl groups that might be present in the R$^{5a-5i}$, R$^{5aa}$, R$^{5ab}$, R$^{5ba}$, R$^{5bb}$, R$^{5bc}$, R$^{5ca}$, R$^{5da}$, R$^{5db}$, R$^{5ea}$, R$^{5eb}$, R$^{5ec}$, R$^{5fa}$ and R$^{5fb}$ moieties.

In one embodiment, R$^5$ is —C$_{0-3}$alkylene-SR$^{5a}$. R$^{5a}$ is H or —C(O)—R$^{5aa}$. The R$^{5aa}$ group is —C$_{1-6}$alkyl, —C$_{0-6}$alkylene-C$_{3-7}$cycloalkyl, —C$_{0-6}$alkylenearyl, —C$_{0-6}$alkyleneheteroaryl, —CO$_{0-6}$alkylenemorpholine, —C$_{0-6}$alkylenepiperazine-CH$_3$, —CH(NH$_2$)-aa where aa is an amino acid side chain, -2-pyrrolidine, —C$_{0-6}$alkylene-OR$^{5ab}$, —O—C$_{0-6}$alkylenearyl, —C$_{1-2}$alkylene-OC(O)—C$_{1-6}$alkyl, —C$_{1-2}$alkylene-OC(O)—C$_{0-6}$alkylenearyl, or —O—C$_{1-2}$alkylene-OC(O)O—C$_{1-6}$alkyl. The R$^{5ab}$ group is H or —C$_{1-6}$alkyl. In one specific embodiment, R$^{5a}$ is H, for example, R$^5$ may be —SH or —CH$_2$SH. In another embodiment, R$^{5a}$ is —C(O)—R$^{5aa}$, where R$^{5aa}$ is —C$_{1-6}$alkyl. Exemplary —C$_{1-6}$alkyl groups include —CH$_3$, —CH$_2$CH$_3$, —CH(CH$_3$)$_2$, —C(CH$_3$)$_3$, and —CH$_2$CH(CH$_3$)$_2$. Thus, examples of R$^5$ include —SC(O)CH$_3$, —CH$_2$SC(O)CH$_3$, —CH$_2$SC(O)CH$_2$CH$_3$, —CH$_2$SC(O)CH(CH$_3$)$_2$ and —CH$_2$SC(O)C(CH$_3$)$_3$, and —CH$_2$SC(O)CH$_2$CH(CH$_3$)$_2$. In one embodiment, R$^{1a}$ is selected from H and —C(O)—C$_{1-6}$alkyl.

In one embodiment, R$^{5a}$ is —C(O)—R$^{5aa}$, where R$^{5aa}$ is —C$_{0-6}$alkylene —C$_{3-7}$cycloalkyl. Exemplary C$_{3-7}$cycloalkyl groups include cyclopentyl and cyclohexyl. Thus, examples of R$^5$ include —CH$_2$SC(O)-cyclopentyl, —CH$_2$SC(O)-cyclohexyl, and —CH$_2$SC(O)—CH$_2$-cyclopentyl. In another embodiment, R$^{5a}$ is —C(O)—R$^{5aa}$, where R$^{5aa}$ is —C$_{0-6}$alkylenearyl. In one specific embodiment, the aryl is optionally substituted with 1 to 3 substituents such as —O—C$_{1-6}$alkyl. Exemplary aryl groups include phenyl and -phenyl-OCH$_3$. Thus, examples of R$^5$ include —CH$_2$SC(O)-phenyl and —CH$_2$SC(O)-phenyl-OCH$_3$. In yet another embodiment, R$^{5a}$ is —C(O)—R$^{5aa}$, where R$^{5aa}$ is —C$_{0-6}$alkyleneheteroaryl. Exemplary heteroaryl groups include furanyl, thienyl and pyridinyl. Thus, examples of R$^5$ include: —CH$_2$SC(O)-2-pyridine, —CH$_2$SC(O)-3-pyridine, and —CH$_2$SC(O)-4-pyridine. In another embodiment, R$^{5a}$ is —C(O)—R$^{5aa}$, where R$^{5aa}$ is —C$_{0-6}$alkylenemorpholine:

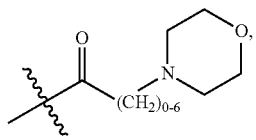 [SMILES: *C(=O)CN1CCOCC1]

more particularly, —C$_{1-3}$ alkylenemorpholine. Thus, examples of R$^5$ include —CH$_2$S—C(O)CH$_2$-morpholine and —CH$_2$S—C(O)(CH$_2$)$_2$-morpholine. In another embodiment, R$^{5a}$ is —C(O)—R$^{5aa}$, where R$^{5aa}$ is —C$_{0-6}$alkylenepiperazine-CH$_3$. Thus, examples of R$^5$ include —CH$_2$S—C(O)(CH$_2$)$_2$-piperazine-CH$_3$. In one embodiment, R$^{5a}$ is —C(O)—R$^{5aa}$, where R$^{5aa}$ is —CH(NH$_2$)-aa where aa is an amino acid side chain. For example, the amino acid side chain could be —CH(CH$_3$)$_2$, the valine side chain. Thus, one example of R$^5$ is —CH$_2$S—C(O)CH(NH$_2$)—CH(CH$_3$)$_2$. In yet another embodiment, R$^{5a}$ is —C(O)—R$^{5''}$, where R$^{5aa}$ is –2-pyrrolidine:

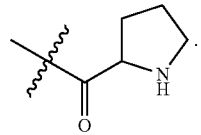 [SMILES: *C(=O)C1CCCN1]

Thus, an example of R$^5$ is —CH$_2$S—C(O)-2-pyrrolidine.

In another embodiment, R$^{5a}$ is —C(O)—R$^{5aa}$, where R$^{5aa}$ is —C$_{0-6}$alkylene-OR$^{5ab}$. In one embodiment, R$^{5ab}$ is H, such that R$^{5a}$ is —C(O)—C$_{0-6}$alkylene-OH. In another embodiment, R$^{5ab}$ is —C$_{1-6}$alkyl, such that R$^{5a}$ is —C(O)—C$_{0-6}$alkylene-O—C$_{1-6}$alkyl, for example, R$^5$ may be —CH$_2$SC(O)—O—CH$_2$CH$_3$.

In another embodiment, R$^{5a}$ is —C(O)—R$^{5aa}$, where R$^{5aa}$ is —O—C$_{0-6}$alkylenearyl. In yet another embodiment, R$^{5a}$ is —C(O)—R$^{5''}$, where R$^{5aa}$ is —C$_{1-2}$alkylene-OC(O)—C$_{1-6}$alkyl and in another embodiment, R$^{5a}$ is —C(O)—R$^{5aa}$, where R$^{5''}$ is —C$_{1-2}$alkylene-OC(O)—C$_{0-6}$alkylenearyl. In yet another embodiment, R$^{5a}$ is —C(O)—R$^{5aa}$, where R$^{5aa}$ is —O—C$_{1-2}$alkylene-OC(O)O—C$_{1-6}$alkyl, for example, R$^5$ may be —CH$_2$SC(O)OCH(CH$_3$)—OC(O)O—CH(CH$_3$)$_2$.

In one embodiment, R$^5$ is —C$_{0-3}$alkylene-C(O)NR$^{5b}$R$^{5c}$. The R$^{5b}$ moiety is H, —OH, —OC(O)R$^{5ba}$, —CH$_2$COOH, —O-benzyl, -pyridyl, or —OC(S)NR$^{5bb}$R$^{5bc}$. R$^{5ba}$ is —C$_{1-6}$alkyl, —O—CH$_2$-aryl (for example, —OCH$_2$-phenyl), —CH$_2$—O-aryl (for example, —CH$_2$O-phenyl), or —NR$^{5bb}$R$^{5bc}$. The R$^{5bb}$ and R$^{5bc}$ moieties are independently selected from H and —C$_{1-4}$alkyl. In one embodiment, R$^{5b}$ is —OH or —OC(O)R$^{5ba}$, where —R$^{5ba}$ is —C$_{1-6}$alkyl. R$^5$ is H, —C$_{1-6}$alkyl, or —C(O)—R$^{5ca}$. R$^{5ca}$ is —C$_{1-6}$alkyl, —C$_{3-7}$cycloalkyl, aryl, or heteroaryl. In one particular embodiment, R$^5$ is H. In another embodiment, R$^{5b}$ is —OH and R$^{5c}$ is H, for example, R$^5$ may be —C(O)NH(OH) or —CH$_2$C(O)NH(OH). In another embodiment, R$^{5b}$ is —OC(O)R$^{5ba}$, where —R$^{5ba}$ is —C$_{1-6}$alkyl, and R$^{5c}$ is H, for example, R$^5$ may be —C(O)N[OC(O)CH$_3$]H or —C(O)N[OC(O)C(CH$_3$)$_3$]H. In still another embodiment, both R$^{5b}$ and R$^{5c}$ are H, for example, R$^5$ may be —C(O)NH$_2$. In another embodiment, R$^{5b}$ is —CH$_2$COOH and R$^{5c}$ is H, for example, R$^5$ may be —C(O)N(CH$_2$COOH)H. In yet another embodiment, R$^{5b}$ is —OC(O)R$^{5ba}$, where —R$^{5ba}$ is —O—CH$_2$-aryl or —CH$_2$—O-aryl, for example, R$^{5b}$ may be —OC(O)OCH$_2$-phenyl or —OC(O)CH$_2$—O-phenyl, and R$^{5c}$ is H. Therefore, examples of R$^5$ include —CH$_2$—C(O)NH[OC(O)OCH$_2$-phenyl] and —CH$_2$—C(O)N[OC(O)—CH$_2$O-phenyl]H. In another embodiment, R$^{5b}$ is —OC(S)NR$^{5bb}$R$^{5bc}$, where R$^{5bb}$ and R$^{5bc}$ are both —C$_{1-4}$alkyl, for example, R$^{5b}$ may be —O—C(S)N(CH$_3$)$_2$. In another embodiment, R$^{5b}$ is —OC(S)NR$^{5bb}$R$^{5bc}$ and R$^{5c}$ is H, for example, R$^5$ may be —CH$_2$—C(O)N[OC(S)N(CH$_3$)$_2$]H.

In one particular embodiment, R$^5$ is selected from —C$_{0-3}$alkylene-SR$^{5a}$ and —C$_{0-3}$alkylene-C(O)NR$^{5b}$R$^{5c}$; where R$^{5a}$ is selected from H and —C(O)—C$_{1-6}$alkyl; R$^{5b}$ is selected from H, —OH, and —OC(O)—C$_{1-6}$alkyl; and R$^{5c}$ is selected from H and —C$_{1-6}$alkyl.

In one embodiment, R$^5$ is —C$_{0-3}$alkylene-NR$^{5b}$—C(O)R$^{5d}$. R$^{5d}$ is H, —C$_{1-4}$alkyl, —C$_{0-3}$alkylenearyl, —NR$^{5da}$R$^{5db}$, —CH$_2$SH, or —O—C$_{1-6}$alkyl. The R$^{5da}$ and R$^{5db}$ moieties are independently selected from H and —C$_{1-4}$alkyl. In another embodiment, R$^{5b}$ is —OH and R$^{5d}$ is H, for example, R$^5$ may be —CH$_2$—N(OH)C(O)H. In another embodiment, $R^{5b}$ is —OH and $R^{5d}$ is —$C_{1-4}$alkyl, for example, $R^5$ may be —$CH_2$—N(OH)C(O)$CH_3$. In another embodiment, $R^{5b}$ is H and $R^{5d}$ is —$CH_2$SH, for example, $R^5$ may be —NHC(O)$CH_2$SH or —$CH_2$NHC(O)—$CH_2$SH.

In yet another embodiment, $R^5$ is —NH—$C_{0-1}$alkylene-P(O)(O$R^{5e}$)$_2$. The $R^{5e}$ moiety is H, —$C_{1-6}$alkyl, —$C_{1-3}$alkylenearyl, —$C_{1-3}$alkyleneheteroaryl, —$C_{3-7}$cycloalkyl, —CH($CH_3$)—O—C(O)$R^{5ea}$,

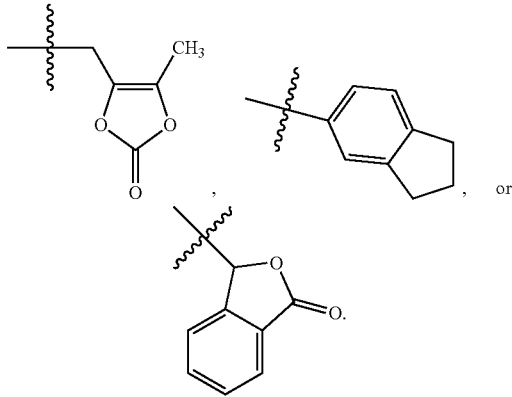

The $R^{5ea}$ group is —O—$C_{1-6}$alkyl, —O—$C_{3-7}$cycloalkyl, —N$R^{5eb}R^{5ec}$, or —CH(NH$_2$)CH$_2$COOCH$_3$. $R^{5eb}$ and $R^{5ec}$ are independently selected from H, —$C_{1-4}$alkyl, and —$C_{1-3}$ alkylenearyl (for example, benzyl). $R^{5eb}$ and $R^{5ec}$ may also be taken together to form —(CH$_2$)$_{3-6}$—. In one embodiment, $R^{5e}$ is H, for example, $R^5$ may be —NH—CH$_2$—P(O)(OH)$_2$.

In one embodiment, $R^5$ is —$C_{0-3}$alkylene-P(O)O$R^{5e}R^{5f}$. The $R^{5f}$ moiety is H, —$C_{1-4}$alkyl, —$C_{0-3}$alkylenearyl, —$C_{1-3}$ alkylene-N$R^{5fa}R^{5fb}$, or —$C_{1-3}$alkylene(aryl)-$C_{0-3}$alkylene-N$R^{5fa}R^{5fb}$. The $R^{5fa}$ and $R^{5fb}$ groups are independently selected from H and —$C_{1-4}$alkyl.

In one embodiment, $R^5$ is —$C_{0-2}$alkylene-CH$R^{5g}$—COOH. The $R^{5g}$ moiety is H, —$C_{1-6}$alkyl, —$C_{1-3}$alkylenearyl, or —CH$_2$—O—(CH$_2$)$_2$—OCH$_3$. In one embodiment, $R^{5g}$ is —CH$_2$—O—(CH$_2$)$_2$—OCH$_3$, for example, $R^5$ may be —CH$_2$—C[CH$_2$—O—(CH$_2$)$_2$—OCH$_3$]H—COOH. In another embodiment, $R^{5g}$ is H, for example, $R^5$ may be —CH$_2$COOH.

In one embodiment, $R^5$ is —$C_{0-3}$alkylene-C(O)N$R^{5h}$—CH$R^{5i}$—COOH. The $R^{5h}$ moiety is H or —$C_{1-4}$alkyl. The $R^{5i}$ moiety is H, —$C_{1-4}$alkyl, or —$C_{0-3}$alkylenearyl. In one embodiment, $R^{5h}$ is H and $R^{5i}$ is —$C_{0-3}$alkylenearyl, and the aryl is optionally substituted with 1 to 3 substituents such as —OH, for example, $R^5$ may be —C(O)NH—CH(CH$_2$-phenyl-OH)(COOH).

In one embodiment, $R^5$ is selected from —$C_{0-3}$alkylene-S$R^{5a}$, —$C_{0-3}$alkylene-C(O)N$R^{5b}R^{5c}$, and —$C_{0-3}$alkylene-N$R^{5b}$—C(O)$R^{5d}$. More particularly, in one embodiment, $R^5$ is selected from —$C_{0-1}$alkylene-SH, —$C_{0-1}$alkylene-C(O)N(OH)H, and —$C_{0-3}$alkylene-N(OH)—C(O)H. In another embodiment, $R^5$ is selected from —$C_{0-3}$alkylene-S$R^{5a}$ and —$C_{0-3}$alkylene-C(O)N$R^{5b}R^{5c}$, where $R^{5a}$ is H; $R^{5b}$ is —OH. In one particular embodiment, $R^{5c}$ is H.

In yet another embodiment, $R^5$ is selected from —$C_{0-3}$alkylene-S$R^{5a}$, —$C_{0-3}$alkylene-C(O)N$R^{5b}R^{5c}$, and —$C_{0-3}$alkylene-N$R^{5b}$—C(O)$R^{5d}$; where $R^{5a}$ is selected from —C(O)—$C_{1-6}$alkyl, —C(O)—$C_{0-6}$alkylene-$C_{3-7}$cycloalkyl, —C(O)—$C_{0-6}$alkylenearyl, —C(O)—$C_{0-6}$alkyleneheteroaryl, —C(O)—$C_{0-6}$alkylenemorpholine, —C(O)—$C_{0-6}$alkylenepiperazine-CH$_3$, —C(O)—CH(NH$_2$)-aa where aa is an amino acid side chain, —C(O)-2-pyrrolidine, —C(O)—O—$C_{1-6}$alkyl, —C(O)—O—$C_{0-6}$alkylenearyl, —$C_{1-2}$alkylene-OC(O)—$C_{1-6}$alkyl, —$C_{1-2}$alkylene-OC(O)—$C_{0-6}$alkylenearyl, and —O—$C_{1-2}$alkylene-OC(O)O—$C_{1-6}$alkyl; and $R^{5b}$ is selected from —OC(O)—$C_{1-6}$alkyl, —CH$_2$COOH, —O-benzyl, -pyridyl, —OC(O)O—CH$_2$-phenyl, —OC(O)CH$_2$—O-phenyl, —OC(O)N(CH$_3$)$_2$, and —OC(S)N(CH$_3$)$_2$. In one particular embodiment, $R^{5c}$ or $R^{5d}$ is H. In another particular embodiment, $R^{5a}$ is selected from —C(O)—$C_{1-6}$alkyl, —C(O)—$C_{0-6}$alkylene-$C_{3-7}$cycloalkyl, —C(O)—$C_{0-6}$alkylenearyl, and —C(O)—$C_{0-6}$alkyleneheteroaryl. In one aspect of the invention, these compounds may find particular utility as prodrugs or as intermediates in the synthetic procedures described herein.

$R^6$ is selected from —$C_{1-6}$alkyl, —CH$_2$O(CH$_2$)$_2$OCH$_3$, —$C_{1-6}$alkylene-O—$C_{1-6}$alkyl, $C_{0-3}$alkylenearyl, —$C_{0-3}$alkyleneheteroaryl, and —$C_{0-3}$alkylene-$C_{3-7}$cycloalkyl. In one particular embodiment, $R^6$ is selected from —$C_{1-6}$alkyl, —$C_{0-3}$alkylenearyl, and —$C_{0-3}$alkylene-$C_{3-7}$cycloalkyl. Each alkyl and each aryl in $R^6$ is optionally substituted with 1 to 7 fluoro atoms, where the term "alkyl" is intended to include divalent alkylene groups such as those present in —$C_{1-6}$alkylene-O—$C_{1-6}$alkyl and —$C_{0-3}$alkylene-$C_{3-7}$cycloalkyl, for example. In addition, each aryl in $R^6$ may be substituted with 1 to 3 —OH, —$C_{1-6}$alkyl, —$C_{2-4}$alkenyl, —$C_{2-4}$alkynyl, —CN, halo, —O—$C_{1-6}$alkyl, —S—$C_{1-6}$alkyl, —S(O)—$C_{1-6}$alkyl, —S(O)$_2$—$C_{1-4}$alkyl, -phenyl, —NO$_2$, —NH—$C_{1-6}$alkyl, or —N($C_{1-6}$alkyl)$_2$ groups. Further, each of the aforementioned alkyl, alkenyl and alkynyl groups may be substituted with 1 to 5 fluoro atoms.

In one embodiment, $R^6$ is —$C_{1-6}$alkyl, for example, —CH$_3$, —CH$_2$CH$_3$, —CH(CH$_3$)$_2$, —(CH$_2$)$_2$CH$_3$, —(CH$_2$)$_3$CH$_3$, —CH(CH$_3$)CH$_2$CH$_3$, —CH$_2$CH(CH$_3$)$_2$, —CH$_2$C(CH$_3$)$_3$, —(CH$_2$)$_2$CH(CH$_3$)$_2$, or —(CH$_2$)$_4$—CH$_3$. As noted above, each alkyl in $R^6$ is optionally substituted with 1 to 7 fluoro atoms. Examples of such fluoro-substituted $R^6$ groups include —(CH$_2$)$_2$CF$_3$ and —(CH$_2$)$_3$CF$_3$.

In another embodiment, $R^6$ is —CH$_2$O(CH$_2$)$_2$OCH$_3$. In still another one embodiment, $R^6$ is —$C_{1-6}$alkylene-O—$C_{1-6}$ alkyl, for example, —OCH$_3$ and —CH$_2$OCH$_3$.

In one embodiment, $R^6$ is —$C_{0-3}$alkylenearyl, for example, phenyl, benzyl, —CH$_2$-biphenyl, —(CH$_2$)$_2$-phenyl and —CH$_2$-naphthalen-1-yl. The aryl may be substituted with 1 to 3 substituents. Thus, other examples of $R^6$ include monosubstituted groups such as, methylbenzyl, chlorobenzyl, fluorobenzyl, fluorophenyl, bromobenzyl, iodobenzyl, -benzyl-CF$_3$, 2-trifluoromethyl-benzyl, -benzyl-CN, and -benzyl-NO$_2$; and di-substituted groups such as di-chlorobenzyl and di-fluorobenzyl. Each aryl may also be substituted with 1 to 7 fluoro atoms. Thus, other examples of $R^6$ include penta-fluorobenzyl.

In one embodiment, $R^6$ is —$C_{0-3}$alkyleneheteroaryl, for example, —CH$_2$-pyridyl, —CH$_2$-furanyl, —CH$_2$-thienyl, and —CH$_2$-thiophenyl.

In another embodiment, $R^6$ is —$C_{0-3}$alkylene-$C_{3-7}$cycloalkyl, for example, —CH$_2$-cyclopropyl, cyclopentyl, —CH$_2$-cyclopentyl, -cyclohexyl, and —CH$_2$-cyclohexyl.

$R^7$ is H or is taken together with $R^6$ to form —$C_{3-8}$cycloalkyl. In one embodiment, $R^7$ is H. In another embodiment, $R^7$ is taken together with $R^6$ to form —$C_{3-8}$cycloalkyl, for example cyclopentyl.

In one particular embodiment, the compound of formula I is the species embodied in formula Ia:

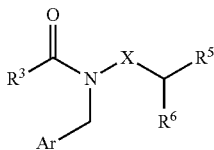

and in one specific embodiment, Ar is selected from

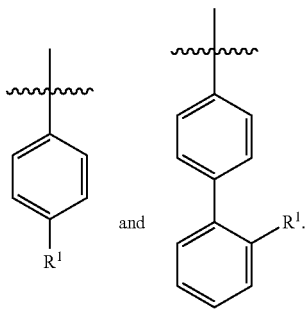

and $R^1$, $R^3$, X, and $R^{5-6}$ are as defined for formula I; and pharmaceutically acceptable salts thereof. In another embodiment, the compound of formula I is the species embodied in formula Ib:

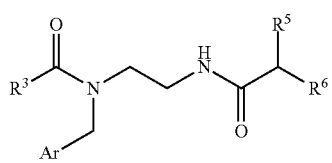

and in one specific embodiment, Ar is selected from

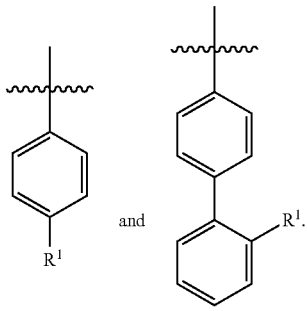

and $R^1$, $R^3$, and $R^{5-6}$ are as defined for formula I; and pharmaceutically acceptable salts thereof. In yet another embodiment, the compound of formula I is the species embodied in formula Ic:

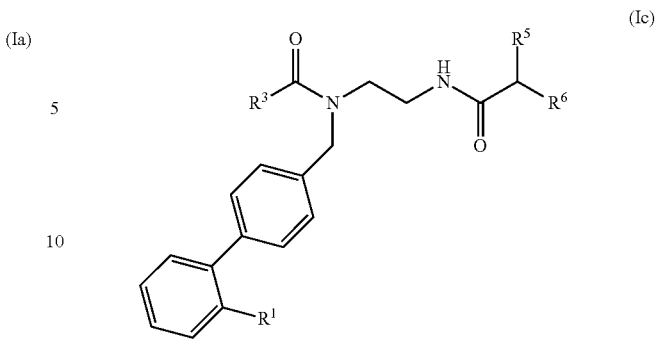

where $R^1$, $R^3$, and $R^{5-6}$ are as defined for formula I; and pharmaceutically acceptable salts thereof.

In one particular embodiment, $R^1$ is selected from —COOH, —$SO_2NHR^{1d}$, and tetrazol-5-yl; and $R^5$ is selected from —$C_{0-3}$alkylene-$SR^{5a}$, —$C_{0-3}$alkylene-C(O)$NR^{5b}R^{5e}$, and —$C_{0-3}$alkylene-$NR^{5b}$—C(O)$R^{5d}$; where $R^{5a}$, $R^{5c}$, and $R^{5d}$ are H, and $R^{5b}$ is —OH. In another aspect, this embodiment has formula Ia, Ib or Ic.

In one particular embodiment, $R^1$ is selected from —COOH, —$SO_2NHR^{1d}$, and tetrazol-5-yl; and $R^5$ is selected from —$C_{0-3}$alkylene-$SR^{5a}$, —$C_{0-3}$alkylene-C(O)$NR^{5b}R^{5c}$, and —$C_{0-3}$alkylene-$NR^{5b}$—C(O)$R^{5d}$; where $R^{5a}$ is selected from —C(O)—$C_{1-6}$alkyl, —C(O)—$C_{0-6}$alkylene-$C_{3-7}$cycloalkyl, —C(O)—$C_{0-6}$alkylenearyl, —C(O)—$C_{0-6}$alkyleneheteroaryl, —C(O)—$C_{0-6}$alkylenemorpholine, —C(O)—$C_{0-6}$alkylenepiperazine-$CH_3$, —C(O)—CH($NH_2$)-aa where aa is an amino acid side chain, —C(O)-2-pyrrolidine, —C(O)—O—$C_{1-6}$alkyl, —C(O)—O—$C_{0-6}$alkylenearyl, —$C_{1-2}$alkylene-OC(O)—$C_{1-6}$alkyl, —$C_{1-2}$alkylene-OC(O)—$C_{0-6}$alkylenearyl, and —O—$C_{1-2}$alkylene-OC(O)—O—$C_{1-6}$alkyl; and $R^{5b}$ is selected from —OC(O)—$C_{1-6}$alkyl, —$CH_2$COOH, —O-benzyl, -pyridyl, —OC(O)—O—$CH_2$-phenyl, —OC(O)$CH_2$—O-phenyl, —OC(O)N($CH_3$)$_2$, and —OC(S)N($CH_3$)$_2$. In another aspect, this embodiment has formula Ia, Ib or Ic. This embodiment may find particular utility as an intermediate or as a prodrug.

In one particular embodiment, $R^1$ is —$COOR^{1a}$ and $R^{1a}$ is —$C_{1-6}$alkyl, —$C_{1-3}$alkylenearyl, —$C_{1-3}$alkyleneheteroaryl, —$C_{3-7}$cycloalkyl, —CH($C_{1-4}$alkyl)OC(O)$R^{1aa}$, —$C_{0-6}$alkylenemorpholine,

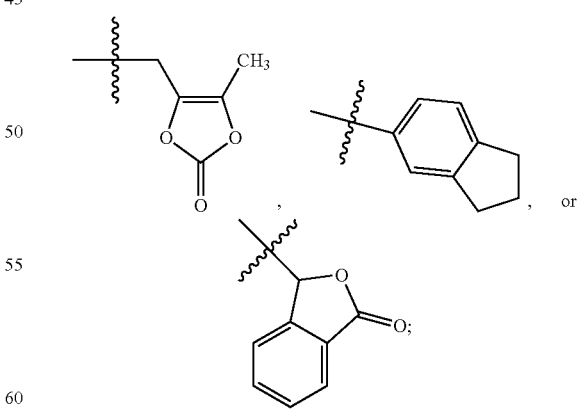

and $R^5$ is selected from —$C_{0-3}$alkylene-$SR^{5a}$, —$C_{0-3}$alkylene-C(O)$NR^{5b}R^{5e}$, and —$C_{0-3}$alkylene-$NR^{5b}$—C(O)$R^{5d}$; where $R^{5a}$, $R^{5c}$, and $R^{5d}$ are H, and $R^{5b}$ is —OH. In another aspect, this embodiment has formula Ia, Ib or Ic. This embodiment may find particular utility as an intermediate or as a prodrug.

In one particular embodiment, $R^1$ is —COOR$^{1a}$ and $R^{1a}$ is —C$_{1-6}$alkyl, —C$_{1-3}$alkylenearyl, —C$_{1-3}$alkyleneheteroaryl, —C$_{3-7}$cycloalkyl, —CH(C$_{1-4}$alkyl)OC(O)R$^{1aa}$, —C$_{0-6}$alkylenemorpholine,

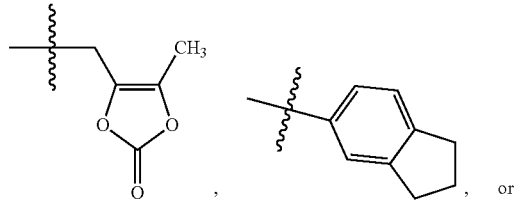

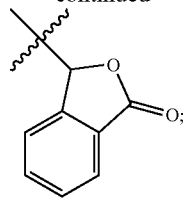

and $R^5$ is selected from —C$_{0-3}$alkylene-SR$^{5a}$, —C$_{0-3}$alkylene-C(O)NR$^{5b}$R$^{5c}$, and —C$_{0-3}$alkylene-NR$^{5b}$—C(O)R$^{5d}$; where R$^{5a}$ is selected from —C(O)—C$_{1-6}$alkyl, —C(O)—C$_{0-6}$ alkylene-C$_{3-7}$cycloalkyl, —C(O)—C$_{0-6}$alkylenearyl, —C(O)—C$_{0-6}$alkyleneheteroaryl, —C(O)—C$_{0-6}$alkylenemorpholine, —C(O)—C$_{0-6}$alkylenepiperazine-CH$_3$, —C(O)—CH(NH$_2$)-aa where aa is an amino acid side chain, —C(O)-2-pyrrolidine, —C(O)—O—C$_{1-6}$alkyl, —C(O)—O—C$_{0-6}$alkylenearyl, —C$_{1-2}$alkylene-OC(O)—C$_{1-6}$alkyl, —C$_{1-2}$alkylene-OC(O)—C$_{0-6}$alkylenearyl, and —O—C$_{1-2}$alkylene-OC(O)O—C$_{1-6}$alkyl; and R$^{5b}$ is selected from —OC(O)—C$_{1-6}$alkyl, —CH$_2$COOH, —O-benzyl, -pyridyl, —OC(O)O—CH$_2$-phenyl, —OC(O)CH$_2$—O-phenyl, —OC(O)N(CH$_3$)$_2$, and —OC(S)N(CH$_3$)$_2$. In another aspect, this embodiment has formula Ia, Ib or Ic. This embodiment may find particular utility as an intermediate or as a prodrug.

Another embodiment of the invention provides for an active compound of formula I where Ar**—COOH represents Ar—R$^1$ and R$^5$ is —C$_{0-3}$alkylene-SH. One corresponding prodrug (prodrug A) can contain a thioester linkage, which can be cleaved in vivo to form the —COOH(R$^1$) and —C$_{0-3}$alkylene-SH(R$^5$) moieties. Another corresponding prodrug (prodrug B, where Z is —C$_{1-6}$alkylene, optionally substituted with one or more moieties such as hydroxyl, phenyl, carboxyl, and so forth), contains both an ester and a thioester group, which can be similarly cleaved in vivo, but which also releases a physiologically acceptable acid such as α-hydroxy acid (Z is —CH$_2$—), β-hydroxy acid (Z is —(CH$_2$)$_2$—), (R)-2-hydroxypropionic or lactic acid (Z is —CH(CH$_3$)—), (R)-hydroxyphenylacetic or mandelic acid (Z is —CH(phenyl)-), salkylic acid (Z is -phenylene-), 2,3-dihydroxysuccinic or tartaric acid (Z is —CH(COOH)—CH(OH)—), citric acid (Z is —CH$_2$—C(CH$_2$—COOH)$_2$—), hydroxy bis- and hydroxy-tris acids, and so forth.

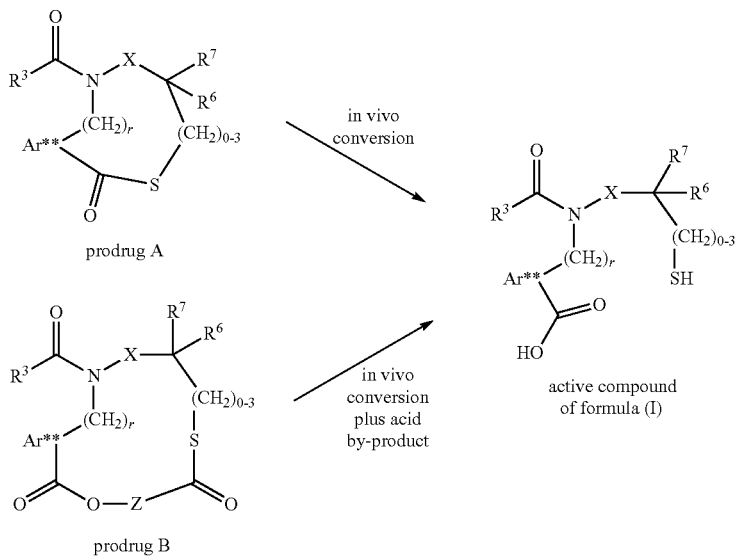

prodrug A prodrug B active compound of formula (I)

In one particular embodiment, the compound of formula I is the species embodied in formula Ia, wherein: Ar is an aryl group selected from:

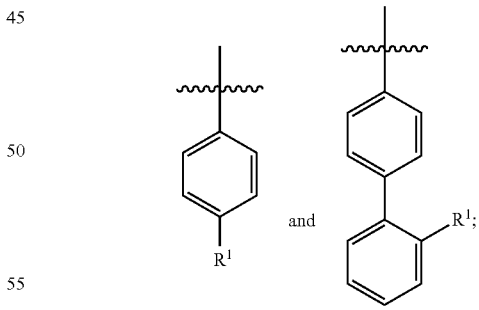

$R^1$ is selected from —COOR$^{1a}$, —SO$_2$NHR$^{1d}$, and tetrazol-5-yl; where R$^{1a}$ is selected from H and —C$_{1-6}$alkyl; R$^{1d}$ is —C(O)R$^{1c}$; and R$^{1c}$ is —C$_{1-6}$alkyl; R$^3$ is selected from —C$_{1-10}$ alkyl, —C$_{0-3}$alkylene-C$_{3-7}$cycloalkyl, —C$_{0-5}$alkylene-NR$^{3a}$—C$_{0-5}$alkylene-R$^{3b}$, —C$_{0-5}$alkylene-O—C$_{0-5}$alkylene-R$^{3b}$, and —C$_{0-3}$alkylenearyl; where R$^{1a}$ is H; and R$^{3b}$ is selected from H, —C$_{1-6}$alkyl, and phenyl; X is —C$_{2-11}$alkylene-, where 1, 2 or 3 —CH$_2$— moieties in the alkylene are replaced with a —NR$^{4a}$—C(O)— or —C(O)—NR$^{4a}$— moiety, where R$^{4a}$ is H; R$^5$ is selected from —C$_{0-3}$ alkylene-SR$^{5a}$, —C$_{0-3}$alkylene-C(O)NR$^{5b}$R$^{5c}$, and —C$_{0-1}$alkylene-NHC(O)CH$_2$SH; where R$^{5a}$ is selected from H and —C(O)—C$_{1-6}$ alkyl; R$^{5b}$ is selected from —OH and —OC(O)—C$_{1-6}$alkyl; and R$^{5c}$ is H; R$^6$ is selected from —C$_{1-6}$alkyl, —C$_{0-3}$alkylenearyl, and —C$_{0-3}$alkylene-C$_{3-2}$cycloalkyl; each carbon atom in X is optionally substituted with one or two R$^{4b}$ groups selected from —C$_{0-5}$alkylene-COOR$^{4c}$ and —C$_{1-6}$alkyl, where R$^{4c}$ is H; and pharmaceutically acceptable salts thereof. Each alkyl and each aryl in R$^1$, R$^3$, R$^{4a-4d}$, and R$^{5-6}$ as well as each ring in Ar and each aryl in R$^1$, R$^3$, and R$^{5-6}$ are optionally substituted as described above for formula I.

In yet another embodiment, the compound of formula I is the species embodied in formula Ia, wherein: Ar is:

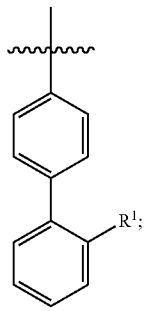

R$^1$ is selected from —SO$_2$NHR$^{1d}$ and tetrazol-5-yl; where R$^{1d}$ is —C(O)R$^{1c}$ and R$^{1c}$ is —C$_{1-6}$alkyl; R$^3$ is selected from —C$_{2-5}$alkyl and —C$_{0-1}$alkylene-C$_{3-5}$cycloalkyl; X is —C$_{2-5}$ alkylene-, where 1 or 2 —CH$_2$— moieties in the alkylene are replaced with a —NR$^{4a}$—C(O)— or —C(O)—NR$^{4a}$— moiety, where R$^{4a}$ is H; R$^5$ is selected from —C$_{0-3}$alkylene-SR$^{5a}$ and —C$_{0-3}$alkylene-C(O)NR$^{5b}$R$^{5c}$; where R$^{5a}$ is selected from H and —C(O)—C$_{1-6}$alkyl; R$^{5b}$ is selected from —OH and —OC(O)—C$_{1-6}$alkyl; and R$^{5e}$ is H; R$^6$ is selected from —C$_{1-6}$alkyl, —C$_{0-3}$alkylenearyl, and —C$_{0-3}$alkylene-C$_{3-2}$ cycloalkyl; one carbon atom in X is optionally substituted with one R$^{4b}$ group selected from —COOH and —C$_{1-3}$alkyl; and pharmaceutically acceptable salts thereof. Each alkyl and each aryl in R$^1$, R$^3$, R$^{4a-4d}$, and R$^{5-6}$ as well as each ring in Ar and each aryl in R$^1$, R$^3$, and R$^{5-6}$ are optionally substituted as described above for formula I.

In yet another embodiment, the compound of formula I is the species embodied in formula Id:

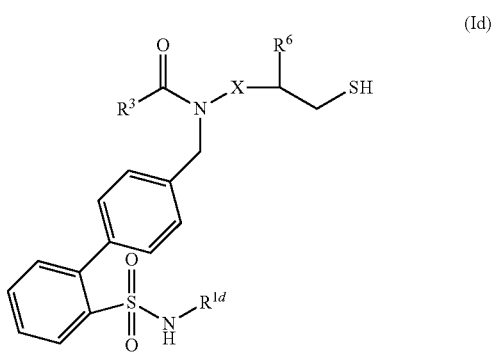

wherein: R$^{1d}$ is —C(O)R$^{1c}$; R$^{1c}$ is —C$_{1-6}$alkyl or —C$_{0-6}$alkylene-O-R$^{1ca}$; R$^{1ca}$ is H; R$^3$ is —C$_{1-10}$alkyl; X is —(CH$_2$)$_2$—NHC(O)— or —(CH$_2$)$_2$—C(O)NH—; and R$^6$ is selected from —C$_{1-6}$alkyl, —C$_{0-3}$alkylenearyl, and —C$_{0-3}$alkylene-C$_{3-2}$cycloalkyl; and pharmaceutically acceptable salts thereof. In addition, each alkyl and each aryl in R$^{1d}$, R$^3$, and R$^6$ as well as each ring in Ar and each aryl in R$^6$ are optionally substituted as described above for formula I. In one particular embodiment, one ring in Ar is optionally substituted with 1-2 halo groups, and in another embodiment substituted with one halo group such as fluoro. In another embodiment, the aryl in R$^6$ is optionally substituted with a halo group. In one exemplary embodiment, the compounds of formula Id have the (R) configuration at the R$^6$ carbon as shown in formula Id':

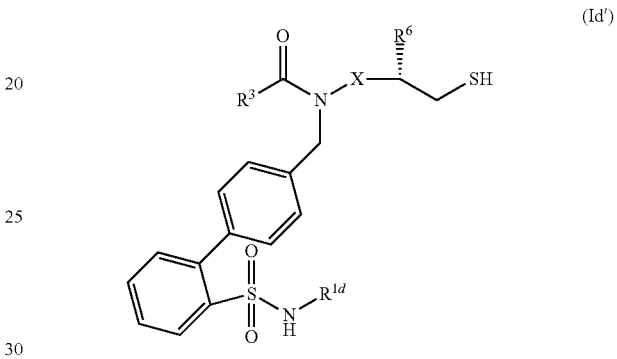

In another exemplary embodiment, the compounds of formula Id, where R$^{1d}$ is —C(O)CH$_3$ or —C(O)—CH(CH$_3$)OH; and R$^6$ is i-butyl, benzyl, -2-fluorobenzyl, -3-chlorobenzyl, or cyclohexyl.

A particular group of compounds of formula I are those disclosed in U.S. Provisional Application No. 60/899,264, filed on Feb. 2, 2007 and No. 60/901,531, filed on Feb. 15, 2007. This group includes compounds of formula I':

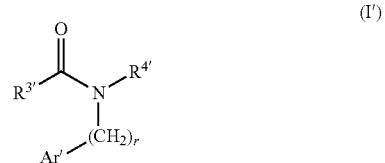

wherein: r is 0, 1 or 2; Ar' is an aryl group selected from:

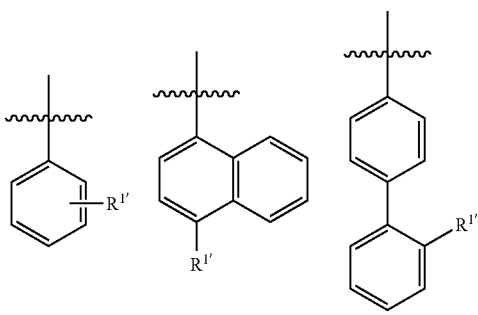

-continued

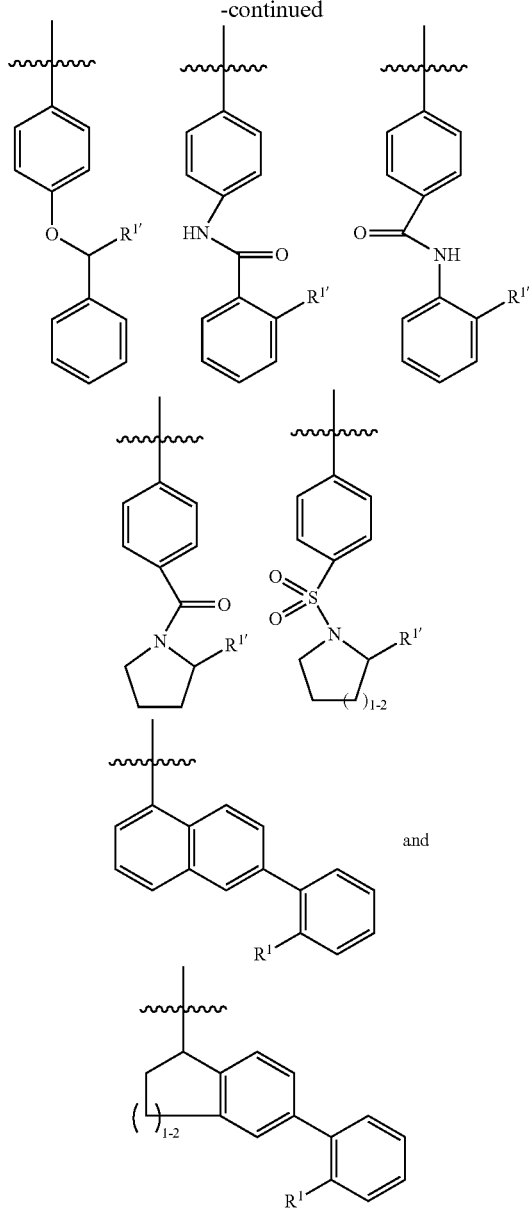

$R^{1'}$ is selected from —COOR$^{1a'}$, —NHSO$_2$C$_{1-6}$alkyl, —NHSO$_2$aryl, —NHSO$_2$NH—C(O)—C$_{1-6}$alkyl, —NHSO$_2$NH—C(O)-aryl, —SO$_2$NH—C(O)—C$_{1-6}$alkyl, —SO$_2$NH—C(O)—C$_{1-6}$aryl, —SO$_2$NH—C(O)—NH—C$_{1-6}$ alkyl, —SO$_2$NH—C(O)—NH-aryl, —SO$_2$OH, —SO$_2$NH$_2$, —SO$_2$NH—C$_{1-6}$alkyl, —SO$_2$NH—C$_{1-6}$aryl, —C(O)—NH—SO$_2$—C$_{1-6}$alkyl, —C(O)—NH—SO$_2$-aryl, —P(O)(OH)$_2$, —CN, —O—CH(CH$_3$)—COOH, —O—CH(aryl)-COOH, tetrazol-5-yl,

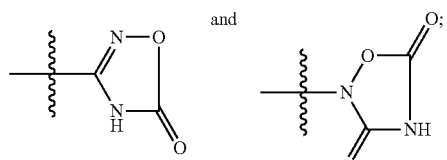

where R$^{1a'}$ is selected from H, —C$_{1-6}$alkyl, benzyl, —C$_{1-3}$alkylene-heteroaryl, cycloalkyl, —CH(CH$_3$)OC(O)R$^{1b'}$,

[structures shown: methyl-dioxolone and indane]

R$^{1b'}$ is selected from —O—C$_{1-6}$alkyl, —O-cycloalkyl, —NR$^{1c'}$R$^{1d'}$, CH(NH$_2$)CH$_2$COOCH$_3$; and R$^{1c'}$ and R$^{1d'}$ are independently selected from H, —C$_{1-6}$alkyl, and benzyl, or are taken together as —(CH$_2$)$_{3-6}$—;

R$^{3'}$ is selected from —C$_{1-10}$alkyl, —C$_{2-10}$alkenyl, —C$_{3-10}$alkynyl, —C$_{3-7}$cycloalkyl, —C$_{0-3}$alkylene-C$_{3-7}$cycloalkyl, —C$_{0-3}$alkenylene-C$_{3-7}$cycloalkyl, —C$_{0-3}$alkynylene-C$_{3-7}$cycloalkyl, —(CH$_2$)$_{0-5}$NR$^{3c'}$(CH$_2$)$_{0-5}$R$^{3b}$, —(CH$_2$)$_{0-5}$O(CH$_2$)$_{1-5}$R$^{3b'}$, —(CH$_2$)$_{1-5}$S(CH$_2$)$_{1-5}$R$^{3b'}$, and —C$_{0-3}$alkylenephenyl; where R$^{3b'}$ is selected from H, —C$_{1-6}$alkyl, —C$_{3-6}$cycloalkyl, —C$_{2-4}$alkenyl, —C$_{2-4}$alkynyl, and phenyl; and R$^{1c'}$ is selected from H, —C$_{1-6}$alkyl, —C$_{3-6}$cycloalkyl, phenyl, and benzyl;

R$^{4'}$ is selected from —X—CHR$^{5'}$R$^{6'}$ and $$—X'\underset{()_{1-6}}{\overset{R^{7'}}{\triangleleft}};$$

X' is C$_{1-12}$alkylene, where at least one —CH$_2$— moiety in the alkylene is replaced with a —NR$^{4a'}$—C(O)— or —C(O)—NR$^{4a'}$— moiety, where R$^{4a'}$ is selected from H, —OH, and —C$_{1-4}$alkyl;

R$^{5'}$ is selected from —C$_{0-3}$alkylene-SR$^{5a'}$, —C$_{0-3}$alkylene-C(O)NR$^{5b'}$R$^{5c'}$, —C$_{0-3}$alkylene-NR$^{5b'}$—C(O)R$^{5d'}$, —C$_{0-1}$alkylene-NHC(O)CH$_2$SH, —NH—C$_{0-1}$alkylene-P(O)(OH)$_2$, and —C$_{0-2}$alkylene-COOH; where R$^{5a'}$ is selected from H, —C(O)—C$_{1-6}$alkyl, —C(O)—C$_{0-6}$alkylene-cycloalkyl, —C(O)—C$_{0-6}$alkylene-aryl, and —C(O)—C$_{0-6}$alkylene-heteroaryl; R$^{5b'}$ is selected from H, —OH, —OC(O)C$_{1-6}$alkyl, —CH$_2$COOH, —O-benzyl, -pyridyl, —OC(O)O—CH$_2$-phenyl, —OC(O)CH$_2$O-phenyl, —OC(O)N(CH$_3$)$_2$, and —OC(S)N(CH$_3$)$_2$; R$^{5c'}$ is selected from H, —C$_{1-6}$ alkyl, and —C(O)—R$^{5e'}$, where R$^{5e'}$ is selected from —C$_{1-6}$ alkyl, —C$_{3-7}$cycloalkyl, aryl, and heteroaryl; and R$^{5d'}$ is selected from H, —C$_{1-4}$alkyl, —C$_{0-3}$alkylenearyl, —NR$^{5f'}$R$^{5g'}$, and —O—C$_{1-6}$alkyl, where R$^{5f'}$ and R$^{5g'}$ are independently selected from H and —C$_{1-4}$alkyl; and R$^{6'}$ is selected from —C$_{1-6}$alkyl, —CH$_2$O(CH$_2$)$_2$OCH$_3$, —C$_{0-3}$alkylene-aryl, —C$_{0-3}$alkylene-heteroaryl, —C$_{0-3}$alkylene-C$_{3-7}$cycloalkyl, and biphenyl;

wherein: each —CH$_2$— group in —(CH$_2$)$_r$— is optionally substituted with 1 or 2 substituents independently selected from —C$_{1-4}$alkyl and fluoro; each ring in Ar is optionally substituted with 1 to 3 substituents independently selected from —OH, —C$_{1-4}$alkyl, —C$_{2-4}$alkenyl, —C$_{2-4}$alkynyl, —CN, halo, —O(C$_{1-4}$alkyl), —S(C$_{1-4}$alkyl), —S(O)(C$_{1-4}$alkyl), —S(O)$_2$(C$_{1-4}$alkyl), -phenyl, —NH$_2$, —NH(C$_{1-4}$alkyl) and —N(C$_{1-4}$alkyl)$_2$, wherein each alkyl, alkenyl and alkynyl group is optionally substituted with 1 to 5 fluoro atoms; each alkyl in R$^{1'}$ and R$^{5e'}$ is optionally substituted with 1 to 7 fluoro atoms; each benzyl group in $R^{1'}$ is optionally substituted with fluoro, —$CF_3$ or —O—$CF_3$; each alkyl, alkenyl, alkynyl, —$(CH_2)_{0-5}NR^{3c'}(CH_2)_{0-5}R^{3b'}$, —$(CH_2)_{1-5}O(CH_2)_{1-5}R^{3b'}$, and —$(CH_2)_{1-5}S(CH_2)_{1-5}R^{3b'}$ group in $R^{3'}$ is optionally substituted with —$COOR^{3a'}$ and/or 1 to 9 fluoro atoms, where $R^{3a'}$ is selected from H, —$C_{1-8}$ perfluoroalkyl, —$C_{3-6}$cycloalkyl, phenyl and benzyl; the —$C_{0-3}$alkylenephenyl group in $R^{3'}$ is optionally substituted on the phenyl ring with 1 to 2 halo, —$C_{1-4}$alkyl, —$C_{1-4}$alkoxy, —OH, or —$NO_2$ groups; each carbon atom in the alkylene moiety in X' is optionally substituted with one more $R^{4b'}$ groups and one —$CH_2$— moiety in X' may be replaced with —$C_{4-8}$cycloalkylene; wherein $R^{4b'}$ is selected from —$C_{0-5}$alkylene-COOH, —$C_{1-6}$alkyl, —$C_{0-1}$alkylene-$CONH_2$, —$C_{1-2}$alkylene-OH, —$C_{0-3}$alkylene-$C_{3-7}$cycloalkyl, and benzyl; the aryl in $R^{5a'}$ is optionally substituted with 1 to 3 groups selected from —$C_{1-4}$alkyl, —$C_{1-4}$alkoxyl, —$C_{1-4}$alkylthio, —OH, —Cl, —Br, —F, —$NH_2$, —NH—$C_{1-4}$alkyl, —$N(C_{1-4}$alkyl$)_2$, —$NO_2$ and —$CF_3$; the alkyl in $R^{6'}$ is optionally substituted with 1 to 7 halo atoms; and each aryl in $R^{1'}$ and $R^{6'}$, and the benzyl group in $R^{1a'}$ is optionally substituted with one or more —$C_{1-6}$alkyl, —$C_{1-6}$alkoxy, halo, phenyl, trifluoromethyl, —$NO_2$, —CN or —OH groups; or a pharmaceutically acceptable salt thereof. In another embodiment, $R^{7'}$ is selected from —$C_{1-2}$alkylene-$CHR^{7a}$—COOH and —$C_{0-3}$alkylene-$C(O)NR^{7b'}$—$CHR^{7c'}$—COOH, where $R^{7a'}$ is selected from H, —$C_{1-9}$alkyl, and —$CH_2$—O—$(CH_2)_2$—$OCH_3$; $R^{7b'}$ is selected from H and —$C_{1-4}$alkyl; and $R^{7c'}$ is selected from H, —$C_{1-4}$alkyl, and hydroxybenzyl.

In addition, compounds of formula I that are of particular interest include those set forth in the Examples below, as well as the pharmaceutically acceptable salts thereof.

DEFINITIONS

When describing the compounds, compositions, methods and processes of the invention, the following terms have the meanings set forth below, unless indicated otherwise. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements.

The term "pharmaceutically acceptable" refers to a material that is not biologically or otherwise undesirable. For example, the term "pharmaceutically acceptable carrier" refers to a material that can be incorporated into a composition and administered to a patient without causing undesirable biological effects or interacting in a deleterious manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

As used herein, the term "prodrug" is intended to mean an inactive (or significantly less active) precursor of a drug that is converted into its active form in the body under physiological conditions, for example, by normal metabolic processes. The term is also intended to include certain protected derivatives of compounds of formula I that may be made prior to a final deprotection stage. Such compounds may not possess pharmacological activity at $AT_1$ and/or NEP, but may be administered orally or parenterally and thereafter metabolized in the body to form compounds of the invention which are pharmacologically active at $AT_1$ and/or NEP. Thus, all protected derivatives and prodrugs of compounds formula I are included within the scope of the invention. Prodrugs of compounds of formula I having a free carboxyl, sulfhydryl or hydroxy group can be readily synthesized by techniques that are well known in the art. These prodrug derivatives are then converted by solvolysis or under physiological conditions to be the free carboxyl, sulfhydryl and/or hydroxy compounds. Exemplary prodrugs include: esters including $C_{1-6}$alkylesters and aryl-$C_{1-6}$alkylesters, carbonate esters, hemi-esters, phosphate esters, nitro esters, sulfate esters, sulfoxides, amides, carbamates, azo-compounds, phosphamides, glycosides, ethers, acetals and ketals. In one embodiment, the compounds of formula I have a free sulfhydryl or a free carboxyl and the prodrug is an ester derivative.

The term "solvate" means a complex or aggregate formed by one or more molecules of a solute, for example, a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need thereof, that is, the amount of drug needed to obtain the desired therapeutic effect. For example, a therapeutically effective amount for treating hypertension could be the amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising an $AT_1$ receptor, an "effective amount" may be the amount needed to antagonize the receptor.

The term "treating" or "treatment" as used herein means the treating or treatment of a disease or medical condition (such as hypertension) in a patient, such as a mammal (particularly a human) that includes: (a) preventing the disease or medical condition from occurring, such as prophylactic treatment of a patient; (b) ameliorating the disease or medical condition such as by eliminating or causing regression of the disease or medical condition in a patient; (c) suppressing the disease or medical condition such as by slowing or arresting the development of the disease or medical condition in a patient; or (d) alleviating the symptoms of the disease or medical condition in a patient. For example, the term "treating hypertension" includes preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition. The term "patient" also includes test subjects in which compounds of the invention are being evaluated or test subjects being used in a assay, for example an animal model.

The term "alkyl" means a monovalent saturated hydrocarbon group which may be linear or branched. Unless otherwise defined, such alkyl groups typically contain from 1 to 10 carbon atoms and include, for example, —$C_{1-4}$alkyl, —$C_{1-6}$alkyl, and —$C_{1-10}$alkyl. Representative alkyl groups include, by way of example, methyl, ethyl, n-propyl, isopropyl, n-butyl, s-butyl, isobutyl, t-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "—$C_{1-6}$alkyl" means an alkyl group having from 1 to 6 carbon atoms, and the term "—$C_{3-7}$cycloalkyl" means a cycloalkyl group having from 3 to 7 carbon atoms, where the carbon atoms are in any acceptable configuration.

The term "alkylene" means a divalent saturated hydrocarbon group that may be linear or branched. Unless otherwise defined, such alkylene groups typically contain from 0 to 12 carbon atoms and include, for example, —$C_{0-1}$alkylene-, —$C_{0-2}$alkylene-, —$C_{0-3}$alkylene-, —$C_{0-5}$alkylene-, —$C_{0-6}$alkylene-, —$C_{1-2}$alkylene- and —$C_{1-12}$alkylene-. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term include zero carbons such as —$C_{0-1}$alkylene- or —$C_{0-5}$alkylene-, such terms are intended to include a single bond.

The term "alkylthio" means a monovalent group of the formula —S-alkyl, where alkyl is as defined herein. Unless otherwise defined, such alkylthio groups typically contain from 1 to 10 carbon atoms and include, for example, —S—$C_{1-4}$alkyl and —S—$C_{1-6}$alkyl. Representative alkylthio groups include, by way of example, ethylthio, propylthio, isopropylthio, butylthio, s-butylthio and t-butylthio.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms and include, for example, —$C_{2-4}$alkenyl and —$C_{2-10}$alkenyl. Representative alkenyl groups include, by way of example, ethenyl, n-propenyl, isopropenyl, n-but-2-enyl, n-hex-3-enyl and the like. The term "alkenylene" means a divalent alkenyl group, and includes groups such as —$C_{2-3}$alkenylene-.

The term "alkoxy" means a monovalent group of the formula —O-alkyl, where alkyl is as defined herein. Unless otherwise defined, such alkoxy groups typically contain from 1 to 10 carbon atoms and include, for example, —O—$C_{1-4}$alkyl and —O—$C_{1-6}$alkyl. Representative alkoxy groups include, by way of example, methoxy, ethoxy, n-propoxy, isopropoxy, n-butoxy, sec-butoxy, isobutoxy, t-butoxy and the like.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms and include, for example, —$C_{2-4}$alkynyl and —$C_{3-10}$alkynyl. Representative alkynyl groups include, by way of example, ethynyl, n-propynyl, n-but-2-ynyl, n-hex-3-ynyl and the like. The term "alkynylene" means a divalent alkynyl group and includes groups such as —$C_{2-3}$alkynylene-.

Amino acid residues are often designated as —C(O)—CHR—NH—, where the R moiety is referred to as the "amino acid side chain." Thus, for the amino acid valine, HO—C(O)—CH[—CH($CH_3$)$_2$]—$NH_2$, the side chain is —CH($CH_3$)$_2$. The term "amino acid side chain" is intended to include side chains of the twenty common naturally occurring amino acids: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Of particular interest are the side chains of non-polar amino acids such as isoleucine, leucine, and valine.

The term "aryl" means a monovalent aromatic hydrocarbon having a single ring (for example, phenyl) or fused rings. Fused ring systems include those that are fully unsaturated (for example, naphthalene) as well as those that are partially unsaturated (for example, 1,2,3,4-tetrahydronaphthalene). Unless otherwise defined, such aryl groups typically contain from 6 to 10 carbon ring atoms and include, for example, —$C_{6-10}$aryl. Representative aryl groups include, by way of example, phenyl and naphthalene-1-yl, naphthalene-2-yl, and the like. The term "arylene" means a divalent aryl group such as phenylene.

The term "cycloalkyl" means a monovalent saturated carbocyclic hydrocarbon group. Unless otherwise defined, such cycloalkyl groups typically contain from 3 to 10 carbon atoms and include, for example, —$C_{3-5}$cycloalkyl, —$C_{3-6}$cycloalkyl and —$C_{3-7}$cycloalkyl. Representative cycloalkyl groups include, by way of example, cyclopropyl, cyclobutyl, cyclopentyl, cyclohexyl and the like. The term "cycloalkylene" means a divalent aryl group such as —$C_{4-8}$cycloalkylene.

The term "halo" means fluoro, chloro, bromo and iodo.

The term "heteroaryl" means a monovalent aromatic group having a single ring or two fused rings and containing in the ring(s) at least one heteroatom (typically 1 to 3) selected from nitrogen, oxygen or sulfur. Unless otherwise defined, such heteroaryl groups typically contain from 5 to 10 total ring atoms and include, for example, —$C_{2-9}$heteroaryl. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzoimidazole, benzthiazole, quinoline, isoquinoline, quinazoline, quinoxaline and the like, where the point of attachment is at any available carbon or nitrogen ring atom.

The term "optionally substituted" means that group in question may be unsubstituted or it may be substituted one or several times, such as 1 to 3 times or 1 to 5 times. For example, an alkyl group that is "optionally substituted" with 1 to 5 fluoro atoms, may be unsubstituted, or it may contain 1, 2, 3, 4, or 5 fluoro atoms.

The term "protected derivatives thereof" means a derivative of the specified compound in which one or more functional groups of the compound are protected or blocked from undergoing undesired reactions with a protecting or blocking group. Functional groups that may be protected include, by way of example, carboxy groups, amino groups, hydroxyl groups, thiol groups, carbonyl groups and the like. Representative protecting groups for carboxy groups include esters (such as a p-methoxybenzyl ester), amides and hydrazides; for amino groups, carbamates (such as t-butoxycarbonyl) and amides; for hydroxyl groups, ethers and esters; for thiol groups, thioethers and thioesters; for carbonyl groups, acetals and ketals; and the like. Such protecting groups are well known to those skilled in the art and are described, for example, in T. W. Greene and G. M. Wuts, *Protective Groups in Organic Synthesis*, Third Edition, Wiley, New York, 1999, and references cited therein.

All other terms used herein are intended to have their ordinary meaning as understood by those of ordinary skill in the art to which they pertain.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (for example, reaction temperatures, times, mole ratios of reactants, solvents, pressures, etc.) are given, other process conditions can also be used unless otherwise stated. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well known in the art. Protecting groups other than those illustrated in the procedures described herein may be used, if desired. For example, numerous protecting groups, and their introduction and removal, are described in T. W. Greene and G. M. Wuts, *Protective Groups in Organic Synthesis*, supra. More specifically, the following abbreviations and reagents are used in the schemes presented below:

$P^1$ represents an "amino-protecting group," a term used herein to mean a protecting group suitable for preventing undesired reactions at an amino group. Representative amino-protecting groups include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like. Standard deprotection techniques are used to remove the $P^1$ group. For example, deprotection of an N—BOC group can involve reagents such as TFA in DCM or HCl in 1,4-dioxane, while a Cbz group can be removed by employing catalytic hydrogenation conditions such as $H_2$ (1 atm), 10% Pd/C in an alcoholic solvent.

$P^2$ represents a "carboxy-protecting group," a term used herein to mean a protecting group suitable for preventing undesired reactions at a carboxy group. Representative carboxy-protecting groups include, but are not limited to, methyl, ethyl, t-butyl, benzyl (Bn), p-methoxybenzyl (PMB), 9-fluoroenylmethyl (Fm), trimethylsilyl (TMS), t-butyldimethylsilyl (TBDMS), diphenylmethyl (benzhydryl, DPM) and the like. Standard deprotection techniques and reagents are used to remove the $P^2$ group, and may vary depending upon which group is used. For example, NaOH is commonly used when $P^2$ is methyl, an acid such as TFA or HCl is commonly used when $P^2$ is t-butyl, and catalytic hydrogenation conditions such as $H_2$ (1 atm) and 10% Pd/C in alcoholic solvent ("$H_2$/Pd/C") may be used when $P^2$ is benzyl.

$P^3$ represents a "thiol-protecting group," a term used herein to mean a protecting group suitable for preventing undesired reactions at a thiol group. Representative thiol-protecting groups include, but are not limited to, ethers, esters such as, —C(O)CH$_3$, and the like. Standard deprotection techniques and reagents such as NaOH, primary alkylamines, and hydrazine, may be used to remove the $P^3$ group.

$P^4$ represents a "tetrazole-protecting group," a term used herein to mean a protecting group suitable for preventing undesired reactions at a tetrazole group. Representative tetrazole-protecting groups include, but are not limited to trityl, benzoyl and diphenylmethyl. Standard deprotection techniques and reagents such as TFA in DCM or HCl in 1,4-dioxane may be used to remove the $P^4$ group.

$P^5$ represents a "hydroxyl-protecting group," a term used herein to mean a protecting group suitable for preventing undesired reactions at a hydroxyl group. Representative hydroxyl-protecting groups include, but are not limited to $C_{1-6}$alkyl, silyl groups including tri$C_{1-6}$alkylsilyl groups, such as trimethylsilyl (TMS), triethylsilyl (TES), and tert-butyldimethylsilyl (TBDMS); esters (acyl groups) including $C_{1-6}$alkanoyl groups, such as formyl, acetyl, and pivaloyl, and aromatic acyl groups such as benzoyl; arylmethyl groups such as benzyl (Bn), p-methoxybenzyl (PMB), 9-fluorenylmethyl (Fm), and diphenylmethyl (benzhydryl, DPM); and the like. Standard deprotection techniques and reagents are used to remove the $P^5$ group, and may vary depending upon which group is used. For example, H₂/Pd/C is commonly used when P⁵ is benzyl, while NaOH is commonly used when P⁵ is an acyl group.

P⁶ represents a "sulfonamide-protecting group," a term used herein to mean a protecting group suitable for preventing undesired reactions at a sulfonamide group. Representative sulfonamide-protecting groups include, but are not limited to t-butyl and acyl groups. Exemplary acyl groups include aliphatic lower acyl groups such as the formyl, acetyl, phenylacetyl, butyryl, isobutyryl, valeryl, isovaleryl and pivaloyl groups, and aromatic acyl groups such as the benzoyl and 4-acetoxybenzoyl. Standard deprotection techniques and reagents are used to remove the P⁶ group, and may vary depending upon which group is used. For example, HCl is commonly used when P⁶ is t-butyl, while NaOH is commonly used when P⁶ is an acyl group.

P⁷ represents a "phosphonate-protecting group or phosphinate-protecting group," a term used herein to mean a protecting group suitable for preventing undesired reactions at a phosphonate or phosphinate group. Representative phosphonate and phosphinate protecting groups include, but are not limited to $C_{1-4}$alkyl, aryl (for example, phenyl) and substituted aryls (for example, chlorophenyl and methylphenyl). The protected group can be represented by —P(O)(OR)₂, where R is a group such as a $C_{1-6}$alkyl or phenyl. Standard deprotection techniques and reagents such as TMS-I/2,6-lutidine and H₂/Pd/C are used to remove the P⁷ group such as ethyl, and benzyl, respectively.

In addition, L is used to designate a "leaving group," a term used herein to mean a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, triflate, tosylate, brosylate, nosylate and the like; acyloxy groups, such as acetoxy, trifluoroacetoxy; formyl groups; and so forth.

Suitable bases for use in these schemes include, by way of illustration and not limitation, potassium carbonate, calcium carbonate, sodium carbonate, triethylamine, pyridine, 1,8-diazabicyclo-[5.4.0]undec-7-ene (DBU), N,N-diisopropyl-ethylamine (DIPEA), sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), dimethyl sulfoxide (DMSO), toluene, dichloromethane (DCM), chloroform (CHCl₃), carbon tetrachloride (CCl₄), 1,4-dioxane, methanol, ethanol, water, and the like.

Suitable carboxylic acid/amine coupling reagents include benzotriazol-1-yloxytris(dimethylamino)phosphonium hexafluorophosphate (BOP), benzotriazol-1-yloxytris(dimethylamino)phosphonium hexafluorophosphate (PyBOP), O-(7-azabenzotriazol-1-yl-N,N,N',N'-tetramethyluronium hexafluorophosphate (HATU), dicyclohexylcarbodiimide (DCC), N-(3-dimethylaminopropyl)-N'-ethylcarbodiimide hydrochloride (EDC), carbonyldiimidazole (CDI), and the like. Coupling reactions are conducted in an inert diluent in the presence of a base, and are performed under conventional amide bond-forming conditions.

All reactions are typically conducted at a temperature within the range of about −78° C. to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, CHCl₃, DCM, chloroform, HCl); washing (for example, with saturated aqueous NaCl, saturated NaHCO₃, Na₂CO₃ (5%), CHCl₃ or 1M NaOH); drying (for example, over MgSO₄, over Na₂SO₄, or in vacuo); filtering; crystallizing (for example, from EtOAc and hexane); and/or being concentrated (for example, in vacuo).

By way of illustration, compounds of formula I, as well as their salts, solvates, and prodrugs can be prepared by one or more of the following exemplary processes.

In the compounds of formula I, X is $C_{1-12}$alkylene, where at least one —CH₂— moiety in the alkylene is replaced with a —NR⁴ᵃ—C(O)— or —C(O)—NR⁴ᵃ— moiety. Step 1 is performed when a —CH₂— moiety in the alkylene is replaced with a —NR⁴ᵃ—C(O)— moiety. Step 1a is performed when a —CH₂— moiety in the alkylene is replaced with a —C(O)—NR⁴ᵃ— moiety.

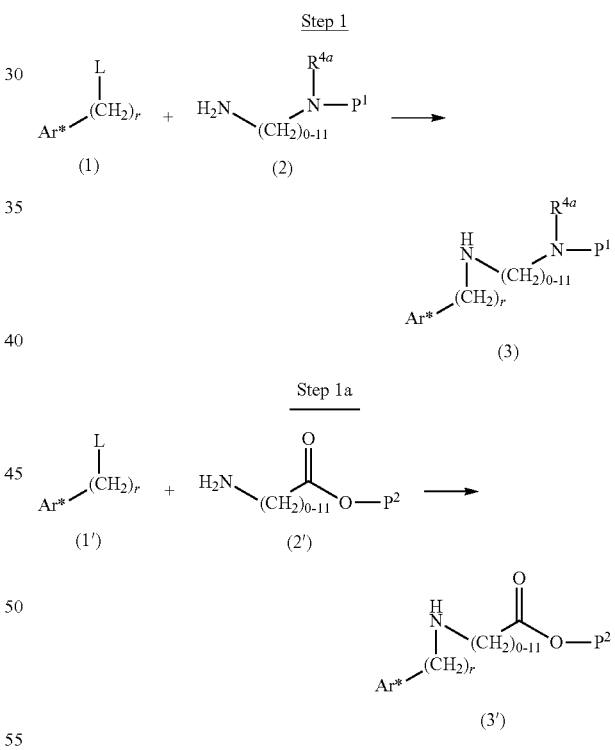

Steps 1 and 1a are standard alkylation reactions and are typically conducted in the presence of a suitable base such as potassium carbonate.

Compound (1): Ar* represents Ar—R¹*, where R¹* may represent R¹ as defined herein, or may represent a protected form of R¹ (for example, -tetrazol-5-yl-P⁴ or —C(O)O—P² such as —C(O)O—$C_{1-6}$alkyl), or may represent a precursor of R¹ (for example, —CN or nitro that is then converted to amino, from which the desired R¹ is prepared). Examples of compound (1) include:

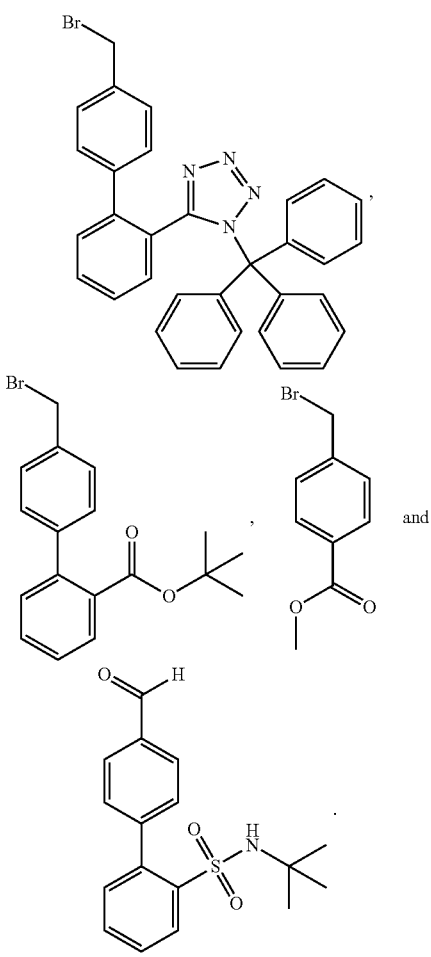

Compound (1) may be synthesized as follows:

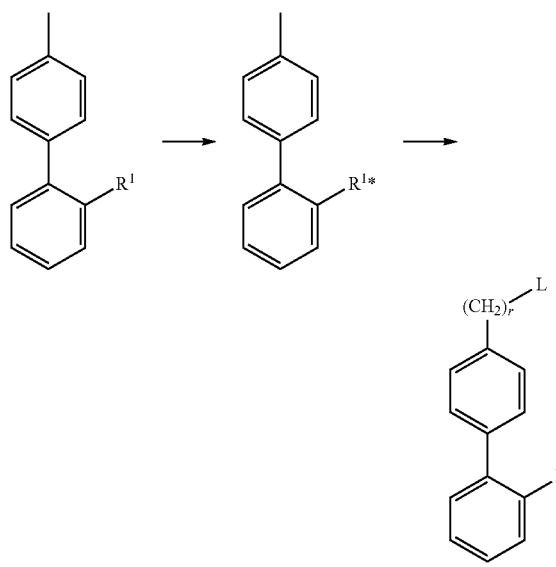

The starting material can be prepared using synthetic methods that are reported in the literature, for example Duncia et al. (1991) *J. Org. Chem.* 56: 2395-400, and references cited therein. Alternatively, the starting material in a protected form may be commercially available. Using a commercially available non-protected starting material, the $R^1$ group is first protected, then the $—(CH_2)_r-L^1$ moiety is added, for example, by a halogenation reaction with a material such as N-bromosuccinimide. For example, a bromination reaction of a methyl group of N-triphenylmethyl-5-[4'-methylbiphenyl-2-yl]tetrazole is described in Chao et al. (2005) *J. Chinese Chem. Soc.* 52:539-544.

In addition, when Ar* has a —CN group, it can be subsequently converted to the desired tetrazolyl group, which may be protected. Conversion of the nitrile group is readily achieved by reaction with a suitable azide such as sodium azide, trialkyltin azide (particularly tributyltin azide) or triaryltin azide.

Compound (1) where $R^1$ is $—SO_2NHR^{1d}$ may also be synthesized as follows:

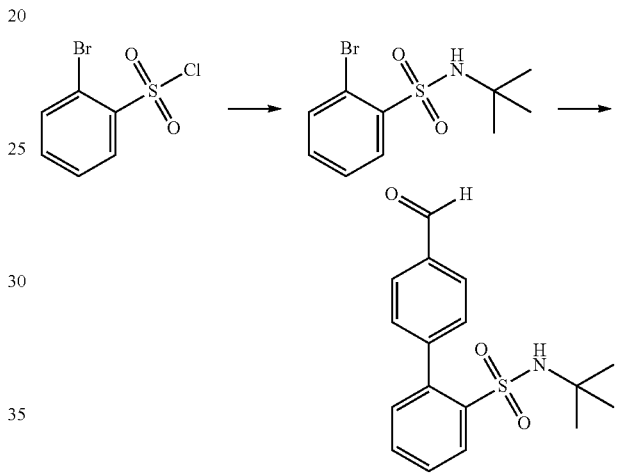

The starting material, 2-bromobenzenesulfonyl chloride, is commercially available. Reaction of 2-bromobenzenesulfonyl chloride in a solvent such as DCM, with t-butylamine in the presence of a base such as DIPEA, yields 2-bromo-N-t-butylbenzenesulfonamide. This intermediate is then coupled with 4-formylphenylboronic acid using Suzuki coupling reaction conditions, to provide compound (1). Representative catalysts include palladium and nickel catalysts, such as tetrakis(triphenylphosphine)palladium(0), [1,1'-bis(diphenylphosphino)ferrocene]dichloropalladium(II), bis[1,2-bis(diphenylphosphino)propane]palladium(0), palladium(II) acetate, [1,1'-bis(diphenylphosphino)ferrocene]dichloronickel(II) and the like. Optionally, a base is employed in this reaction, such as sodium carbonate, sodium bicarbonate, potassium phosphate, triethylamine and the like. Alternately, compound (1), where $R^1$ is $—SO_2NHR^{1d}$, may also be synthesized as follows:

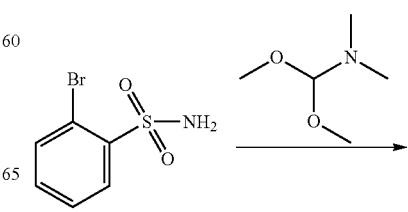

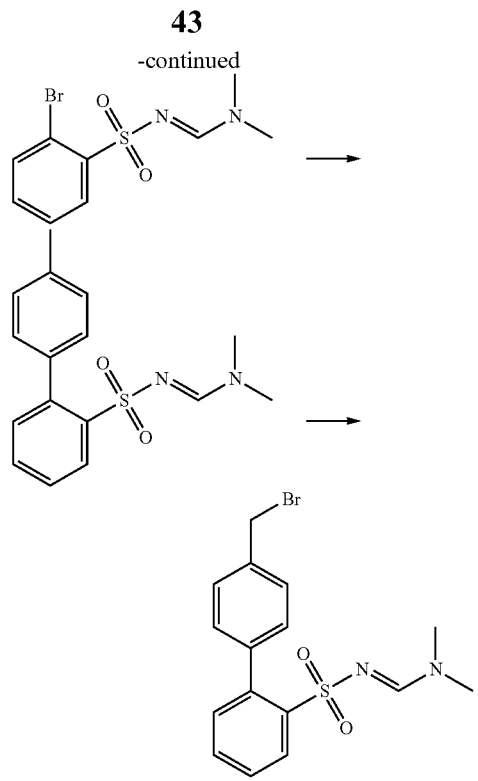

The starting material, 2-bromobenzene-1-sulfonamide, is commercially available. Reaction of 2-bromobenzene-1-sulfonamide in a solvent such as DMF, with 1,1-dimethoxy-N,N-dimethylmethanamine, followed by the addition of sodium hydrogen sulfate in water, yields 2-bromo-N-[1-dimethylaminometh-(E)-ylidene]benzenesulfonamide. This compound is reacted with 4-methylphenylboronic acid to yield 4'-methylbiphenyl-2-sulfonic acid 1-dimethylaminometh-(E)-ylideneamide, then the —$(CH_2)_r$-$L^1$ moiety is added, for example, by a halogenation reaction, to form compound (1).

Compound (1) when Ar has one of the remaining formulas can be readily synthesized using similar techniques or other methods that are well known in the art.

Compound (2): This compound is available commercially or can be readily synthesized by techniques that are well known in the art (Millet et al. (2005) *J. Med. Chem.* 48:7024-39), such as by reacting a diamine of the formula $H_2N$—$(CH_2)_{0-11}$—$NH_2$ and $P^1$—OC(O)OC(O)O—$P^1$, for example, $(CH_3)_3$—COC(O)OC(O)O—C$(CH_3)_3$ ((BOC)$_2$O). Examples of compound (2) include $H_2N$—$(CH_2)_2$—NHC(O)O—C$(CH_3)_3$ (N-(2-aminoethyl) (t-butoxy)carboxamide).

Compound (2'): This compound is available commercially or can be readily synthesized by techniques that are well known in the art. Examples of compound (2') include $H_2N$—$(CH_2)_2$—C(O)O—C$(CH_3)_3$ (Bachem AG, Switzerland).

Step 2

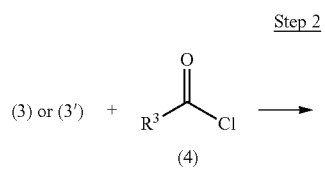

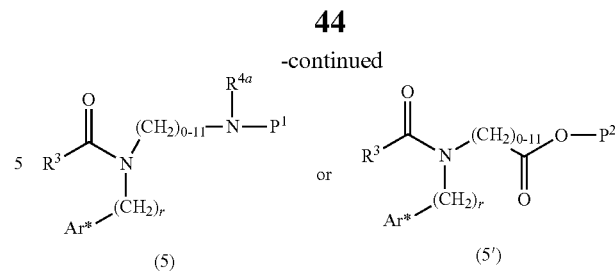

Compounds (5) and (5') are prepared by an acylation reaction of compound (3) or (3') using an appropriate base.

Compound (4): Compound (4) is an acyl halide, examples of which include butyryl chloride, valeryl chloride, isovaleryl chloride, 3-methylpentanoyl chloride, 4-methylpentanoyl chloride, and cyclopropylacetyl chloride. Compound (4) is available commercially or can be readily synthesized by techniques that are well known in the art, such as by treating the corresponding acid of formula $R^3$—COOH with thionyl chloride or oxalyl chloride.

As noted above, X is $C_{1-12}$alkylene, where at least one —$CH_2$— moiety in the alkylene is replaced with a —$NR^{4a}$—C(O)— or —C(O)—N—$R^{4a}$— moiety. Step 3 is performed when a —$CH_2$— moiety in the alkylene is replaced with a —$NR^{4a}$—C(O)— moiety. Step 3a is performed when a —$CH_2$— moiety in the alkylene is replaced with a —C(O)—$NR^{4a}$— moiety. When only one —$CH_2$— moiety is replaced, Step 3 or 3a is followed immediately by Step 4 or 4a, respectively. When more than one —$CH_2$— moiety in the alkylene is replaced, Step 3 or 3a may be followed by as many coupling reactions as is necessary to add the desired amide linkages to the X moiety, before proceeding with the next step.

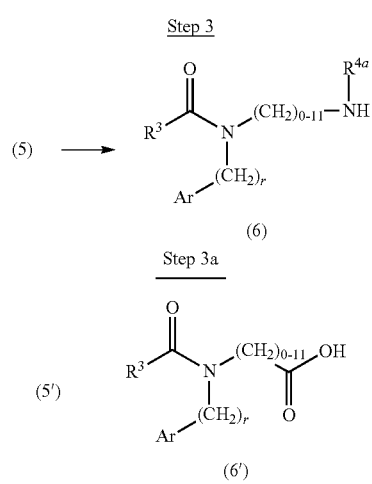

Compound (6) is prepared by deprotection of the protected amine, while compound (6') is prepared by deprotection of the protected ester. Any protecting groups on the Ar* moiety either remain unaffected from the deprotection conditions of the $P^1$ or $P^2$ group, or may also be deprotected in this step. These deprotecting steps can be done in any order or simultaneously.

As noted above, when more than one —$CH_2$— moiety in the alkylene is replaced, the additional replacements may be made prior to Step 4 or 4a. However, any additional replacements may also be present in compound (7) or (7') as is depicted in Steps 4 and 4a.

Step 4

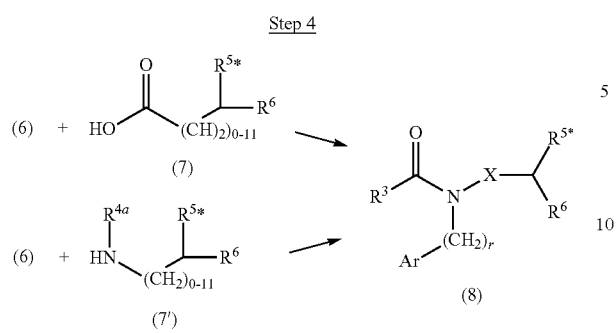

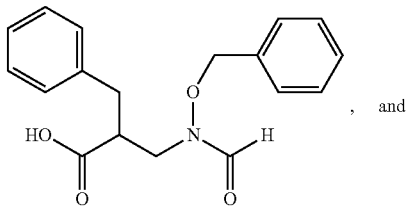
, and

Compound (8) is prepared by coupling of compound (6) and compound (7) or by coupling of compound (6') and compound (7') under conventional amide bond-forming conditions.

$R^{5*}$ may represent $R^5$ as defined herein, or it may represent a protected form of $R^5$. When $R^{5*}$ represents $R^5$, then the reaction is complete after this step, and compound (8) is a compound of formula I. On the other hand, if $R^{5*}$ represents a protected form of $R^5$, a subsequent deprotection step will yield the non-protected compound.

In general, compounds (7) and (7') can be readily synthesized by following techniques described in the literature, for example, Neustadt et al (1994) *J. Med. Chem.* 37:2461-2476 and Moree et al. (1995) *J. Org. Chem.* 60: 5157-69, as well as by using the exemplary procedures described below. Examples of compound (7) include:

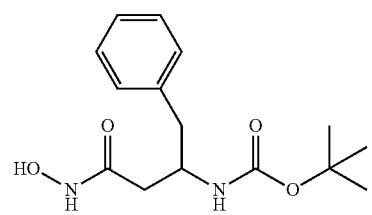

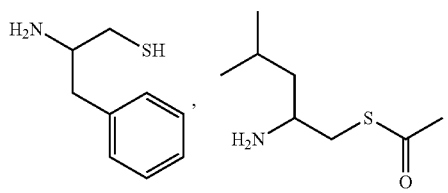

Examples of compound (7') include

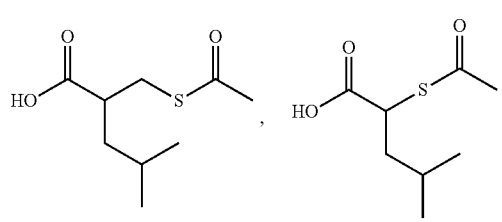

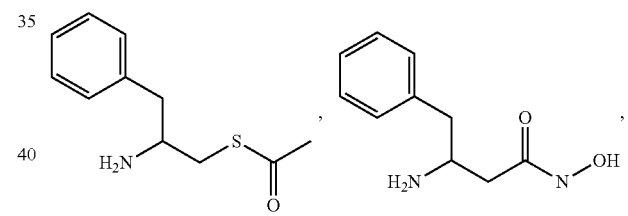

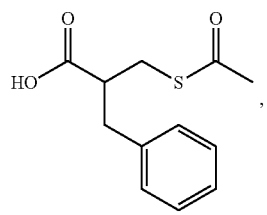

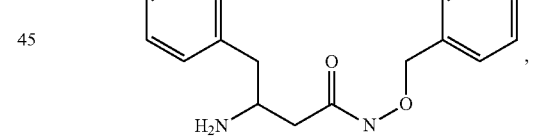

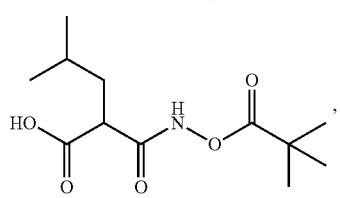

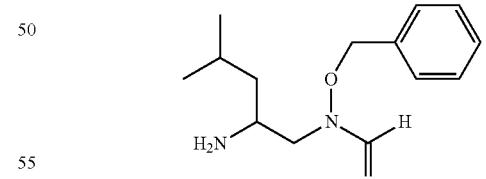

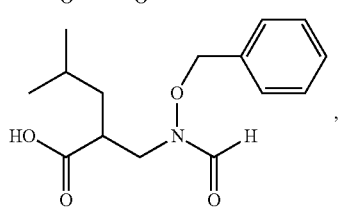

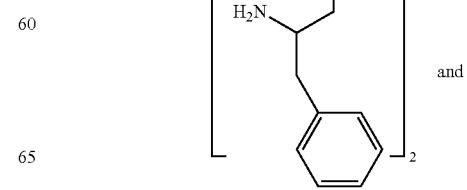
and

-continued

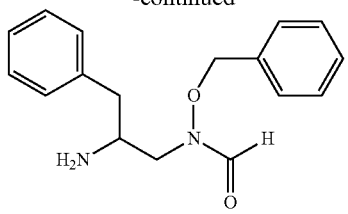

The synthesis of exemplary compounds (7) and (7') are described below. In addition, since compounds (7) and (7') can have a chiral center (not depicted in the above examples), it may be desirable to synthesize a particular stereoisomer, and examples are also provided below.

Preparation of Chiral Amino Hydroxamate Compound (7$^i$)

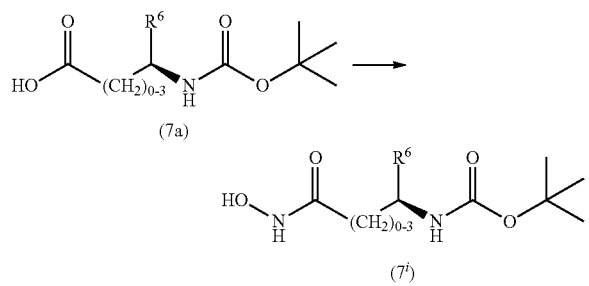

A base such as DIPEA and a coupling agent such as EDC are added to a solution of (7a) in DMF containing 1-hydroxybenzotriazole (HOBt) and hydroxylamine hydrochloride. The mixture is stirred at room temperature until completion (approximately 12 hours), then concentrated in vacuo. The resulting material is partitioned and the organic layer collected and washed with a base (for example, 1M NaOH). The alkaline aqueous layer is then acidified (for example, with 1M phosphoric acid), and extracted. The organic layer is evaporated and the residue purified by silica gel chromatography to afford compound (7'). An exemplary compound (7a) is (R)-3-t-butoxycarbonylamino-4-phenylbutyric acid.

Preparation of Sulfanyl Acid Compound (7$^{ii}$)

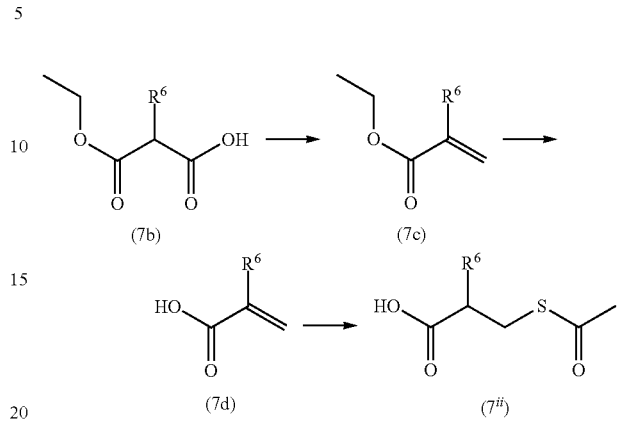

Compound (7b) is mixed with diethylamine and cooled in an ice bath. An aqueous formaldehyde solution (37%) is then added, and the mixture stirred at 0° C. for approximately 2 hours, warmed to room temperature and stirred overnight. The mixture is then extracted with ether, washed, dried, and evaporated to dryness, to provide compound (7c). Compound (7c) is then dissolved in 1,4-dioxane, and a 1M NaOH solution is added. The mixture is stirred at room temperature until completion (approximately 2 days). The organic solvent is removed in vacuo, and the aqueous residue is rinsed with ethyl acetate and acidified to approximately pH 1 with concentrated HCl. The product is extracted with ethyl acetate, dried, and evaporated to dryness to yield compound (7d). Compound (7d) is combined with thiolacetic acid (10 mL), and the mixture is stirred at 80° C. until completion (approximately 2 hours), then concentrated to dryness to yield compound (7), which is dissolved in toluene and concentrated to remove any trace of thiolacetic acid. Examples of compound (7b) include 2-benzylmalonic acid monoethyl ester ($R^6$=benzyl) and 2-isobutylmalonic acid monoethyl ester ($R^6$=isobutyl).

Preparation of Chiral Amino Sulfhydryl Dimer Compound (7$^{iii}$)

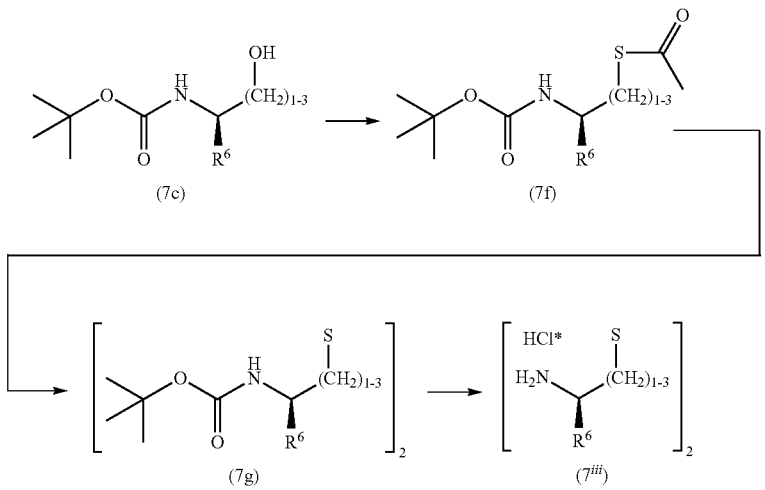

Diisopropyl azodicarboxylate is added to a solution of triphenylphosphine in a solvent such as THF, cooled in an ice bath. The solution is stirred and (7e) and thioacetic acid are added. The mixture is first stirred at 0° C., then at room temperature until the reaction is complete (approximately 12 hours). The mixture is stripped, diluted with ethyl acetate, and washed. The organic layer is dried and the filtrate evaporated to dryness. The resulting material is flash chromatographed to provide (7f). Compound (7f) is dissolved in a suitable solvent, followed by the addition of a base such as 1M LiOH. Air is bubbled through the solution for 1 hour followed by the addition of solvent. The mixture is stirred at room temperature until the reaction is complete (approximately 24 hours). The solution is then acidified to approximately pH 5, for example with acetic acid. The precipitate is filtered and rinsed, to provide the dimer (7g). This solid is suspended in MeCN, then concentrated in vacuo. The recovered material is dissolved in 4M HCl in 1,4-dioxane and stirred at room temperature until the reaction is complete (approximately 2 hours). The mixture is then concentrated under reduced pressure, and triturated with ethyl acetate. The product is filtered, washed, and dried in vacuo to provide compound (7$^{iii}$). An exemplary compound (7e) is ((12)-1-benzyl-(2-hydroxyethyl)carbamic acid t-butyl ester.

Preparation of Chiral Sulfanyl Acid Compound (7$^{iv}$)

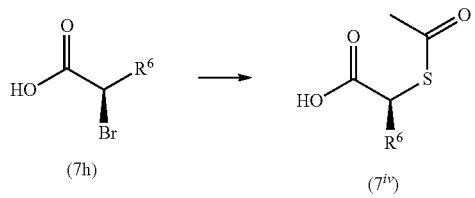

Compound (7h) is formed by dissolving a compound such as D-leucine (for R$^6$=isobutyl) in 3M HBr (aqueous) and cooled to 0° C. A solution of sodium nitrite in water is added, and the mixture is stirred at 0° C. until the reaction is complete (approximately 2.5 hours). The mixture is then extracted with ethyl acetate, washed, dried, filtered, and concentrated to afford (7h). Compound (7h) is combined with potassium thioacetate and DMF, and the mixture stirred at room temperature until the reaction is complete (approximately 1 hour). Water is added, and the mixture is extracted, washed, dried, filtered, and concentrated to provide compound (7$^{iv}$). The product is purified by silica gel chromatography. An exemplary compound (7h) is (R)-2-bromo-4-methylpentanoic acid.

Preparation of Chiral Sulfanyl Acid Compound (7$^v$)

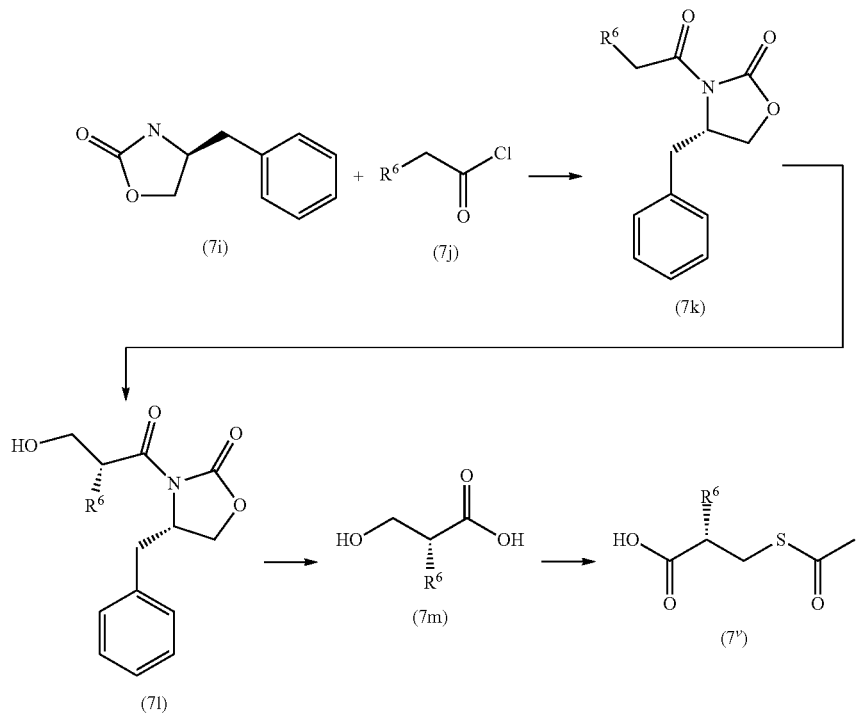

Compound (7i), (S)-4-benzyl-2-oxazolidinone, is commercially available. Compound (7j) is also typically commercially available or can be readily synthesized. For example, R$^6$—CH$_2$—COOH (for example, isocaproic acid or 3-phenylpropionic acid) is dissolved in methylene chloride and thionyl chloride is added. The mixture is stirred at room temperature until the reaction is complete (for example, overnight), and then concentrated to provide (7j). Examples of compound (7j) include 4-methylpentanoyl chloride and 3-phenylpropionyl chloride.

Compound (7i) is dissolved in a suitable solvent and cooled (−78° C.) under nitrogen. n-Butyllithium in hexanes is added dropwise and stirred, followed by the addition of (7j) dropwise. The mixture is stirred at −78° C., then warmed to 0° C. Saturated NaHCO$_3$ is added and the mixture warmed to room temperature. The mixture is extracted, washed, dried, filtered, and concentrated to afford (7k). Compound (7k) is dissolved in DCM and stirred at 0° C. under nitrogen. 1M Titanium tetrachloride is added, followed by 1,3,5-trioxane, all in appropriate solvents. A second equivalent of 1M titanium tetrachloride is added and the mixture stirred at 0° C. until the reaction is complete. The mixture is then quenched with saturated ammonium chloride. Appropriate solvents are added, the aqueous phase is extracted, and the organic layers are combined, dried, filtered, and concentrated to provide (7l), which can then be purified by silica gel chromatography or used in the next step without further purification. Compound (7l) is dissolved in a solvent, to which is added 9 M hydrogen peroxide in water, followed by the dropwise addition of 1.5 M lithium hydroxide monohydrate in water. The mixture is warmed to room temperature and stirred. Optionally, potassium hydroxide may be added and the mixture heated at 60° C. then cooled at room temperature. To this is added an aqueous solution of sodium sulfite followed by water and chloroform. The aqueous layer is extracted, acidified and extracted again. The organic layer is washed, dried, filtered, and rotovaped to provide (7m). Triphenylphosphine is dissolved in an appropriate solvent and cooled at 0° C. (ice bath). Diisopropyl azodicarboxylate is added dropwise and the mixture stirred. Compound (7m) and thioacetic acid, dissolved in an appropriate solvent, are added dropwise to the mixture. After the addition, the mixture is removed from the ice bath and stirred at room temperature until the reaction is complete (approximately 3.5 hours), concentrated, and then partitioned. The organic layer is extracted and the combined aqueous extracts washed, acidified and extracted. The organic layer is washed again, dried, filtered, and rotovaped to provide compound (7ʹ).

Alternately, the coupling step can be done by the two-step method shown below:

Step 4a

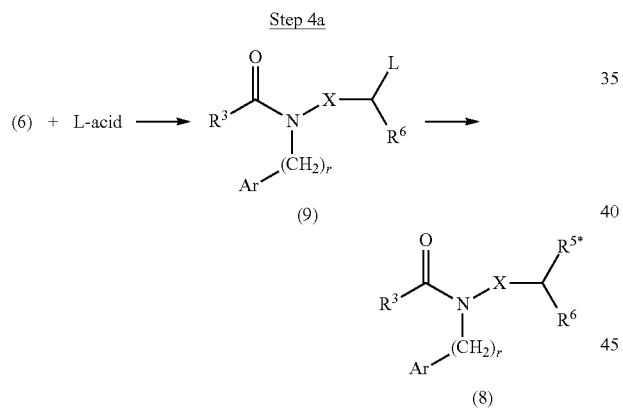

The coupling reaction can be done, for example, in the presence of a halogen-substituted alkanoic acid ("L-acid") such as α-bromoisocaproic acid to provide compound (9), where L is a leaving group such as bromo. Compound (9) is then reacted with a thiol or sulfur-containing nucleophilic reactant that contains the desired $R^{5*}$ group, for example, potassium thioacetate or thiourea.

Step 5 (Optional)

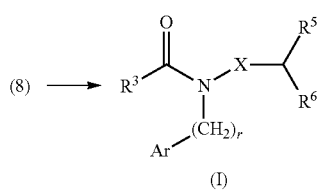

The reaction is complete after Step 4 when $R^{5*}$ represents $R^5$ in compound (8) and $R^1$ does not contain any protecting groups. However, when $R^{5*}$ represents a protected form of $R^5$ and $R^1$ is a protected form, a global or sequential deprotection step of compound (8) will provide the desired compound. Reagents and conditions for the deprotection vary with the nature of protecting groups in the compound (8). Typical deprotection conditions when $R^{5*}$ represents $C_{0-3}$alkylene-S—$P^3$, include treating the compound with NaOH in an alcoholic solvent at room temperature to yield the non-protected compound. Typical deprotection conditions when $R^{1*}$ represents $C(O)O$—$P^2$ where $P^2$ refers to t-butyl include treating the compound with TFA in DCM at room temperature to yield the non-protected compound.

In an alternate synthesis, compound (3) is reacted with a protecting reagent ($P^{1ʺ}$-L) such as Cbz-Cl to provide compound (10), where L is a leaving group such as chloro and $P^{1ʺ}$ is a different amino-protecting group than $P^1$:

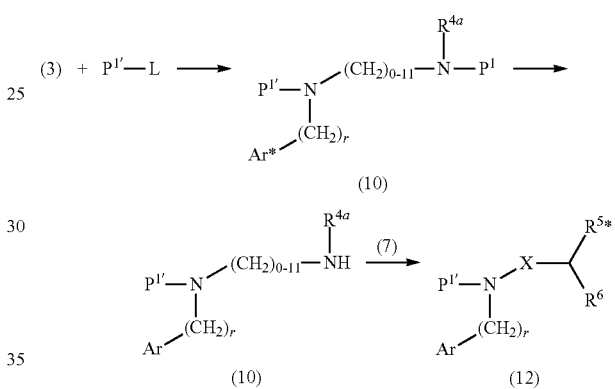

Compound (10) is then selectively deprotected to yield compound (11), which is then coupled with compound (7) to provide compound (12).

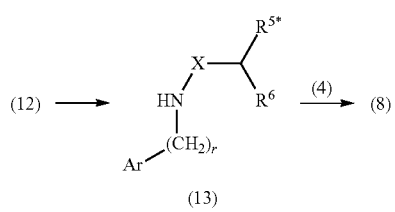

Compound (12) is then selectively deprotected to yield compound (13), which is then acylated with compound (4) to yield compound (8).

The following synthesis is useful, for example, when a carbon atom in the alkylene moiety in X is substituted with an $R^{4b}$ group:

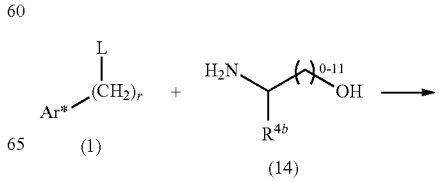

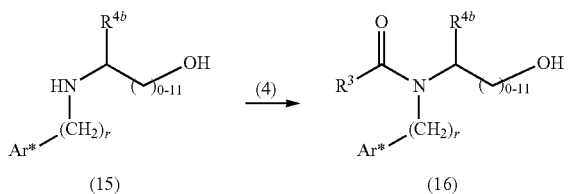

A standard alkylation reaction between compounds (1) and (14) provides compound (15), which is then acylated using compound (4) to provide (16). Examples of compound (14) include (2S)-2-aminopropan-1-ol.

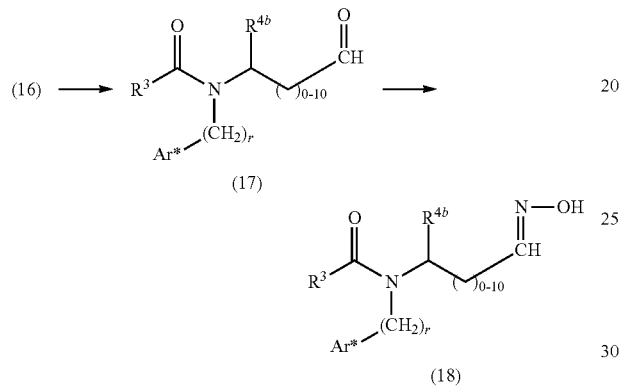

Compound (16) then undergoes an oxidation reaction of the alcohol to form the aldehyde (17), which is then converted to the oxime (18) by reaction with hydroxylamine hydrochloride.

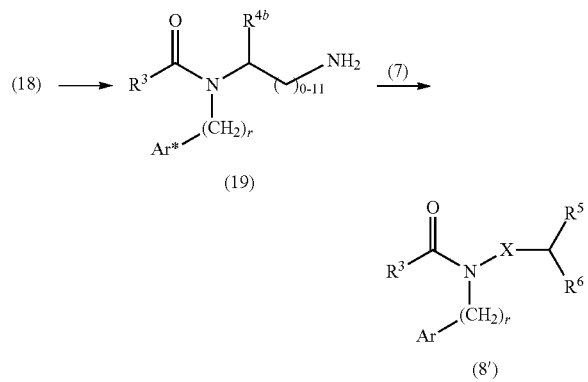

Compound (18) is then reduced to the amine (19), which is then coupled with compound (7) and deprotected, if needed, to provide (8'), where X is substituted an $R^{4b}$ group.

If desired, pharmaceutically acceptable salts of the compounds of formula I can be prepared by contacting the free acid or base form of a compound of formula I with a pharmaceutically acceptable base or acid.

Certain of the intermediates described herein are believed to be novel and accordingly, such compounds are provided as further aspects of the invention including, for example, the compounds of formulas II, III and IV, and salts thereof:

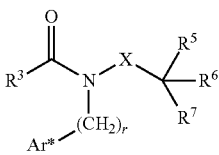

where Ar* is Ar—$R^{1*}$; Ar, r, $R^3$, X, and $R^{5-7}$ are as defined for formula I; and $R^{1*}$ is selected from —C(O)O—$P^2$, —SO$_2$O—$P^5$, —SO$_2$NH—$P^6$, —P(O)(O—$P^7$)$_2$, —OCH(CH$_3$)—C(O)O—$P^2$, —OCH(aryl)-C(O)O—$P^2$, and tetrazol-5-yl-$P^4$; where $P^2$ is a carboxy-protecting group, $P^4$ is a tetrazole-protecting group, $P^5$ is a hydroxyl-protecting group, $P^6$ is a sulfonamide-protecting group, and $P^7$ is a phosphonate-protecting group or phosphinate-protecting group;

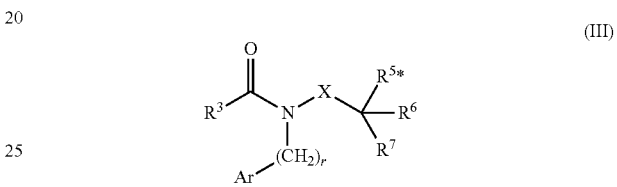

where Ar, r, $R^3$, X, and $R^{6-7}$ are as defined for formula I; $R^{5*}$ is selected from —C$_{0-3}$alkylene-S—$P^3$, —C$_{0-3}$alkylene-C(O)NH(O—$P^5$), —C$_{0-3}$alkylene-N(O—$P^5$)—C(O)$R^{5d}$, —C$_{0-1}$alkylene-NHC(O)CH$_2$S—$P^3$, —NH—C$_{0-3}$alkylene-P(O)(O—$P^7$)$_2$, —C$_{0-3}$alkylene-P(O)(O—$P^7$)—$R^{5f}$, —C$_{0-2}$alkylene-CHR$^{5g}$—C(O)O—$P^2$ and —C$_{0-3}$alkylene-C(O)NR$^{5h}$—CHR$^{5i}$—C(O)O—$P^2$; and $R^{5d}$ to $R^{5i}$ are as defined for formula I; where $P^2$ is a carboxy-protecting group, $P^3$ is a thiol-protecting group, $P^5$ is a hydroxyl-protecting group, and $P^7$ is a phosphonate-protecting group or phosphinate-protecting group; and

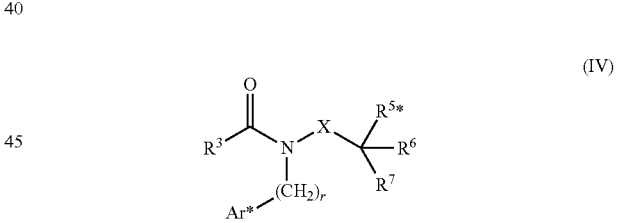

Where Ar* is Ar—$R^{1*}$; Ar, r, $R^3$, X, and $R^{6-7}$ are as defined for formula I; $R^{1*}$ is selected from —C(O)O—$P^2$, —SO$_2$O—$P^5$, —SO$_2$NH—$P^6$, —P(O)(O—$P^7$)$_2$, —OCH(CH$_3$)—C(O)O—$P^2$, —OCH(aryl)-C(O)O—$P^2$, and tetrazol-5-yl-$P^4$; $R^{5*}$ is selected from —C$_{0-3}$alkylene-S—$P^3$, —C$_{0-3}$alkylene-C(O)NH(O—$P^5$), —C$_{0-3}$alkylene-N(O—$P^5$)—C(O)$R^{5d}$, —C$_{0-1}$alkylene-NHC(O)CH$_2$S—$P^3$, —NH—C$_{0-1}$alkylene-P(O)(O—$P^7$)$_2$, —C$_{0-3}$alkylene-P(O)(O—$P^7$)—$R^{5f}$, —C$_{0-2}$alkylene-CHR$^{5g}$—C(O)O—$P^2$ and —C$_{0-3}$alkylene-C(O)NR$^{5i}$—CHR$^{5l}$—C(O)O—$P^2$; and $R^{5d}$ to $R^{5i}$ are as defined for formula I; where $P^2$ is a carboxy-protecting group, $P^3$ is a thiol-protecting group, $P^4$ is a tetrazole-protecting group, $P^5$ is a hydroxyl-protecting group, $P^6$ is a sulfonamide-protecting group, and $P^7$ is a phosphonate-protecting group or phosphinate-protecting group. Thus, another method of preparing compounds of the invention involves deprotecting a compound of formula II, III, or IV.

Further details regarding specific reaction conditions and other procedures for preparing representative compounds of the invention or intermediates thereof are described in the Examples set forth below.

Utility

Compounds of the invention possess angiotensin II type 1 (AT$_1$) receptor antagonist activity. In one embodiment, compounds of the invention are selective for inhibition of the AT$_1$ receptor over the AT$_2$ receptor. Compounds of the invention also possess neprilysin (NEP) inhibition activity, that is, the compounds are able to inhibit enzyme-substrate activity. In another embodiment, the compounds do not exhibit significant inhibitory activity of the angiotensin-converting enzyme. Compounds of formula I may be active drugs as well as prodrugs. Thus, when discussing the activity of compounds of the invention, it is understood that any such prodrugs have the expected AT$_1$ and NEP activity once metabolized.

One measure of a compound's affinity for the AT$_1$ receptor is the inhibitory constant (K$_i$) for binding to the AT$_1$ receptor. The pK$_i$ value is the negative logarithm to base 10 of the K. One measure of the ability of a compound to inhibit NEP activity is the inhibitory concentration (IC$_{50}$), which is the concentration of compound that results in half-maximal inhibition of substrate conversion by the NEP enzyme. The pIC$_{50}$ value is the negative logarithm to base 10 of the IC$_{50}$. Compounds of formula I and pharmaceutically acceptable salts thereof that have both AT$_1$ receptor-antagonizing activity and NEP enzyme-inhibiting activity are of particular interest, including those that exhibit a pK$_i$ at the AT$_1$ receptor greater than or equal to about 5.0, and having a pIC$_{50}$ for NEP greater than or equal to about 5.0.

In one embodiment, compounds of interest have a pK$_i$ at the AT$_1$ receptor ≧about 6.0, a pK$_i$ at the AT$_1$ receptor ≧about 7.0, or a pK$_i$ at the AT$_1$ receptor ≧about 8.0. Compounds of interest also include those having a pIC$_{50}$ for NEP≧about 6.0 or a pIC$_{50}$ for NEP≧about 7.0. In another embodiment, compounds of interest have a pK$_i$ at the AT$_1$ receptor within the range of about 8.0-10.0 and a pIC$_{50}$ for NEP within the range of about 7.0-10.0.

In one embodiment, compounds of interest have a pK$_i$ for binding to an AT$_1$ receptor greater than or equal to about 7.5 and a NEP enzyme pIC$_{50}$ greater than or equal to about 7.0. In another embodiment, compounds of interest have a pK$_i$ greater than or equal to about 8.0 and a pIC$_{50}$ greater than or equal to about 8.0.

It is noted that in some cases, compounds of the invention, while still having dual activity, may possess either weak AT$_1$ receptor antagonist activity or weak NEP inhibition activity. In such cases, those of skill in the art will recognize that these compounds still have utility as primarily either a NEP inhibitor or a AT$_1$ receptor antagonist, respectively, or have utility as research tools.

Exemplary assays to determine properties of compounds of the invention, such as the AT$_1$ receptor binding and/or NEP inhibiting activity, are described in the Examples and include by way of illustration and not limitation, assays that measure AT$_1$ and AT$_2$ binding (described in Assay 1), and NEP inhibition (described in Assay 2). Useful secondary assays include assays to measure ACE inhibition (also described in Assay 2) and aminopeptidase P (APP) inhibition (described in Sulpizio et al. (2005) *JPET* 315:1306-1313). A pharmacodynamic assay to assess the in vivo inhibitory potencies for ACE, AT$_1$, and NEP in anesthetized rats is described in Assay 3 (see also Seymour et al. *Hypertension* 7(Suppl I):I-35-I-42, 1985 and Wigle et al. *Can. J. Physiol. Pharmacol.* 70:1525-1528, 1992), where AT$_1$ inhibition is measured as the percent inhibition of the angiotensin II pressor response, ACE inhibition is measured as the percent inhibition of the angiotensin I pressor response, and NEP inhibition is measured as increased urinary cyclic guanosine 3', 5'-monophosphate (cGMP) output. Useful in vivo assays include the conscious spontaneously hypertensive rat (SHR) model, which is a renin dependent hypertension model useful for measuring AT$_1$ receptor blocking (described in Assay 4; see also Intengan et al. (1999) *Circulation* 100(22):2267-2275 and Badyal et al. (2003) *Indian Journal of Pharmacology* 35:349-362), and the conscious desoxycorticosterone acetate-salt (DOCA-salt) rat model, which is a volume dependent hypertension model useful for measuring NEP activity (described in Assay 5; see also Trapani et al. (1989) *J. Cardiovasc. Pharmacol.* 14:419-424, Intengan et al. (1999) *Hypertension* 34(4):907-913, and Badyal et al. (2003) supra). Both the SHR and DOCA-salt models are useful for evaluating the ability of a test compound to reduce blood pressure. The DOCA-salt model is also useful to measure a test compound's ability to prevent or delay a rise in blood pressure. Compounds of the invention are expected to antagonize the AT$_1$ receptor and/or inhibit the NEP enzyme in any of the assays listed above, or assays of a similar nature. Thus, the aforementioned assays are useful in determining the therapeutic utility of compounds of the invention, for example, their utility as antihypertensive agents. Other properties and utilities of compounds of the invention can be demonstrated using other in vitro and in vivo assays well known to those skilled in the art.

Compounds of the invention are expected to be useful for the treatment and/or prevention of medical conditions responsive to AT$_1$ receptor antagonism and/or NEP inhibition. Thus it is expected that patients suffering from a disease or disorder that is treated by antagonizing the AT$_1$ receptor and/or by inhibiting the NEP enzyme can be treated by administering a therapeutically effective amount of a compound of the invention. For example, by antagonizing the AT$_1$ receptor and thus interfering with the action of angiotensin II on its receptors, these compounds are expected to find utility in preventing the increase in blood pressure produced by angiotensin II, a potent vasopressor. In addition, by inhibiting NEP, these compounds are also expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. For example, by potentiating the effects of the natriuretic peptides, compounds of the invention are expected to be useful to treat glaucoma. These compounds are also expected to have other physiological actions, for example, on the renal, central nervous, reproductive and gastrointestinal systems.

Compounds of the invention are expected to find utility in treating and/or preventing medical conditions such as cardiovascular and renal diseases. Cardiovascular diseases of particular interest include heart failure such as congestive heart failure, acute heart failure, chronic heart failure, and acute and chronic decompensated heart failure. Renal diseases of particular interest include diabetic nephropathy and chronic kidney disease. One embodiment of the invention is directed to a method for treating hypertension, comprising administering to a patient a therapeutically effective amount of a compound of the invention. Typically, the therapeutically effective amount is the amount that is sufficient to lower the patient's blood pressure. In one embodiment, the compound is administered as an oral dosage form.

Another embodiment of the invention is directed to a method for treating heart failure, comprising administering to a patient a therapeutically effective amount of a compound of the invention. Typically, the therapeutically effective amount is the amount that is sufficient to lower blood pressure and/or improve renal functions. In one embodiment, the compound is administered as an intravenous dosage form. When used to treat heart failure, the compound may be administered in combination with other therapeutic agents such as diuretics, natriuretic peptides, and adenosine receptors antagonist.

Compounds of the invention are also expected to be useful in preventative therapy, for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

In addition, as NEP inhibitors, compounds of the invention are expected to inhibit enkephalinase, which will inhibit the degradation of endogenous enkephalins. Thus, such compounds may also find utility as analgesics. Due to their NEP inhibition properties, compounds of the invention are also expected to be useful as antitussive agents and antidiarrheal agents (for example, for the treatment of watery diarrhea), as well as find utility in the treatment of menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction, which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, compounds of the invention may be combined with one or more of the following secondary agents: PDE5 inhibitors, dopamine agonists, estrogen receptor agonists and/or antagonists, androgens, and estrogens.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the compound, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and then continue for the period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for the other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of compound that exhibits the desired effectiveness is administered and, further, that administration is continued only so long as is necessary to successfully treat the disease or medical condition.

Since compounds of the invention possess $AT_1$ receptor antagonist activity and/or NEP enzyme inhibition activity, these compounds are also useful as research tools for investigating or studying biological systems or samples having $AT_1$ receptors or a NEP enzyme, for example to study diseases where the $AT_1$ receptor or NEP enzyme plays a role. Any suitable biological system or sample having $AT_1$ receptors and/or a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention an $AT_1$ receptor in a mammal is antagonized by administering an $AT_1$-antagonizing amount of a compound of the invention. In another particular embodiment, NEP enzyme activity in a mammal is inhibited by administering a NEP-inhibiting amount of a compound of the invention. Compounds of the invention can also be used as research tools by conducting biological assays using these compounds.

When used as a research tool, a biological system or sample comprising an $AT_1$ receptor and/or a NEP enzyme is typically contacted with an $AT_1$ receptor-antagonizing or NEP enzyme-inhibiting amount of a compound of the invention. After the biological system or sample is exposed to the compound, the effects of antagonizing the $AT_1$ receptor and/or inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., i.v. or s.c. administration, and so forth. The determining step can involve measuring a response (a quantitative analysis) or can involve making an observation (a qualitative analysis). Measuring a response involves, for example, determining the effects of the compound on the biological system or sample using conventional procedures and equipment, such as radioligand binding assays or measuring ligand-mediated changes in functional assays. The assay results can be used to determine the activity level as well as the amount of compound necessary to achieve the desired result, such as an $AT_1$ receptor-antagonizing and/or a NEP enzyme-inhibiting amount. Typically, the determining step will involve determining the $AT_1$ receptor ligand-mediated effects and/or determining the effects of inhibiting the NEP enzyme.

Additionally, compounds of the invention can be used as research tools for evaluating other chemical compounds, and thus are also useful in screening assays to discover, for example, new compounds having $AT_1$ receptor-antagonizing activity and/or NEP-inhibiting activity. In this manner, a compound of the invention is used as a standard in an assay to allow comparison of the results obtained with a test compound and with compounds of the invention to identify those test compounds that have about equal or superior activity, if any. For example, $K_i$ data (as determined, for example, by a binding assay) for a test compound or a group of test compounds is compared to the $K_i$ data for a compound of the invention to identify those test compounds that have the desired properties, for example, test compounds having a $K_i$ value about equal or superior to a compound of the invention, if any. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include $AT_1$ receptor binding assays and NEP enzyme inhibition assays.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood that any form of the compounds of the invention, (free base, free acid, pharmaceutically acceptable salt, solvate, etc.) that is suitable for the particular mode of administration can be used in the pharmaceutical compositions discussed herein.

Accordingly, in one embodiment, the invention is directed to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount, such as in bulk compositions, or less than a therapeutically effective amount, such as in individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20<sup>th</sup> Edition, Lippincott Williams & White, Baltimore, Md. (2000); and H. C. Ansel et al., *Pharmaceutical Dosage Forms and Drug Delivery Systems*, 7<sup>th</sup> Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In formulations where the compound of the invention contains a thiol group, additional consideration may be given to minimize or eliminate oxidation of the thiol to form a disulfide. In solid formulations, this may be accomplished by reducing the drying time, decreasing the moisture content of the formulation, and including materials such as ascorbic acid, sodium ascorbate, sodium sulfite and sodium bisulfite, as well as materials such as a mixture of lactose and microcrystalline cellulose. In liquid formulations, stability of the thiol may be improved by the addition of amino acids, antioxidants, or a combination of disodium edetate and ascorbic acid.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient such that each unit contains a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages, or dimerization of thiols that may be present in the compound. These formulations may be rendered sterile by use of a sterile injectable medium, a sterilizing agent, filtration, irradiation, or heat.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the compounds of the invention may be administered in combination with one or more other therapeutic agents. Thus, in one embodiment, pharmaceutical compositions of the invention contain other drugs that are co-administered with the compound of the invention. For example, the composition may further comprise one or more drugs, also referred to as "secondary agents(s)", selected from the group of diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, and combinations thereof. Such therapeutic agents are well known in the art, and examples are described below. By combining a compound of the invention with a secondary agent, triple therapy can be achieved; $AT_1$ receptor antagonist activity, NEP inhibition activity and activity associated with the secondary agent (for example, $\beta_1$ adrenergic receptor blocker) can be achieved using only two active components. Since compositions containing two active components are typically easier to formulate than compositions containing three active components, such two-component compositions provide a significant advantage over compositions containing three active components. Accordingly, in yet another aspect of the invention, a pharmaceutical composition comprises a compound of the invention, a second active agent, and a pharmaceutically acceptable carrier. Third, fourth, etc. active agents may also be included in the composition. In combination therapy, the amount of the compound of the invention that is administered, as well as the amount of secondary agents, may be less than the amount typically administered in monotherapy.

Compounds of the invention may be either physically mixed with the second active agent to form a composition containing both agents; or each agent may be present in separate and distinct compositions which are administered to the patient simultaneously or at separate times. For example, compounds of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of a compound of the invention, ranging anywhere from concurrent with administration of a compound of the invention to about 24 hours post-dose. This is also referred to as sequential administration. Thus, compounds of the invention can be orally administered simultaneously or sequentially with another active agent using two tablets, with one tablet for each active agent, where sequential may mean being administered immediately after administration of the compound of the invention or at some predetermined time later (for example, one hour later or three hours later). Alternatively, the combination may be administered by different routes of administration, for example, one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc,) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed below are intended to include all such forms, and are commercially available or can be prepared using conventional procedures and reagents.

In one embodiment, a compound of the invention is administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosernide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with a $\beta_1$ adrenergic receptor blocker. Representative $\beta_1$ adrenergic receptor blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate or metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $\beta_1$ adrenergic receptor blocker is selected from atenolol, bisoprolol, metoprolol, propranolol, sotalol, and combinations thereof.

In one embodiment, a compound of the invention is administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, niludipine, nilvadipine, nimodipine, nisoldipine, nitrendipine, nivaldipine, perhexyline, prenylamine, ryosidine, semotiadil, terodiline, tiapamil, verapamil, and combinations thereof. In one particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof.

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramiprilat, saralasin acetate, spirapril, temocapril, trandolapril, zofenopril, and combinations thereof. In a particular embodiment, the ACE inhibitor is selected from benazepril, enalapril, lisinopril, ramipril, and combinations thereof.

In one embodiment, a compound of the invention is administered in combination with an $AT_1$ receptor antagonist, also known as an angiotensin II type 1 receptor blocker (ARB). Representative ARBs include, but are not limited to, abitesartan, benzyllosartan, candesartan, candesartan cilexetil, elisartan, embusartan, enoltasosartan, eprosartan, fonsartan, forasartan, glycyllosartan, irbesartan, isoteoline, losartan, medoximil, milfasartan, olmesartan, opomisartan, pratosartan, ripisartan, saprisartan, saralasin, sarmesin, tasosartan, telmisartan, valsartan, zolasartan, and combinations thereof. In a particular embodiment, the ARB is selected from candesartan, eprosartan, irbesartan, losartan, olmesartan, saprisartan, tasosartan, telmisartan, valsartan, and combinations thereof. Exemplary salts include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

In another embodiment, a compound of the invention is administered in combination with a neprilysin (NEP) inhibitor. Representative NEP inhibitors include, but are not limited to: candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680 to Hepworth et al. (Pfizer Inc.); JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyppropionamide); SCH-32615 ((S)—N—[N-(1-carboxy-2-phenylethyl)-L-phenylalanyl]-O-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino]cyclohexanecarboxylic acid); and combinations thereof. In a particular embodiment, the NEP inhibitor is selected from candoxatril, candoxatrilat, CGS-24128, phosphoramidon, SCH-32615, SCH-34826, SQ-28603, thiorphan, and combinations thereof. The NEP inhibitor will be administered in an amount sufficient to provide from about 20-800 mg per day, with typical daily dosages ranging from 50-700 mg per day, more commonly 100-600 or 100-300 mg per day.

In yet another embodiment, a compound of the invention is administered in combination with a non-steroidal anti-inflammatory agent (NSAID). Representative NSAIDs include, but are not limited to, acemetacin, acetyl salkylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diflalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lomoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In yet another embodiment, a compound of the invention is administered in combination with an anti-lipid agent. Representative anti-lipid agents include, but are not limited to: statins such as atorvastatin, fluvastatin, lovastatin, pravastatin, rosuvastatin and simvastatin; cholesteryl ester transfer proteins (CETPs); and combinations thereof.

In yet another embodiment, a compound of the invention is administered in combination with an anti-diabetic agent. Representative anti-diabetic agents include, but are not limited to: injectable drugs such as insulin and insulin derivatives; orally effective drugs including biguanides such as metformin, glucagon antagonists, α-glucosidase inhibitors such as acarbose and miglitol, meglitinides such as repaglinide, oxadiazolidinediones, sulfonylureas such as chlorpropamide, glimepiride, glipizide, glyburide and tolazamide, thiazolidinediones such as pioglitazone and rosiglitazone; and combinations thereof.

In one embodiment, a compound of the invention is administered in combination with an anti-thrombotic agent, representative examples of which include, but are not limited to, aspirin, anti-platelet agents, heparin, and combinations thereof. Compounds of the invention may also be administered in combination with a renin inhibitor, examples of which include, but are not limited to, aliskiren, enalkiren, remikiren, and combinations thereof. In another embodiment, a compound of the invention is administered in combination with an endothelin receptor antagonist, representative examples of which include, but are not limited to, bosentan, darusentan, tezosentan, and combinations thereof. Compounds of the invention may also be administered in combination with an endothelin converting enzyme inhibitor, examples of which include, but are not limited to, phosphoramidon, CGS 26303, and combinations thereof. In yet another embodiment, a compound of the invention is administered in combination with an aldosterone antagonist, representative examples of which include, but are not limited to, eplerenone, spironolactone, and combinations thereof.

Combined therapeutic agents may also be helpful in further combination therapy with compounds of the invention. For example, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, may all also be used with the compounds of the invention. Dual-acting agents may also be helpful in combination therapy with compounds of the invention. For example, angiotensin-converting enzyme/neprilysin (ACE/NEP) inhibitors such as: AVE-0848 ((4S,7S,12bR)-7-[3-methyl-2(S)-sulfanylbutyramido]-6-oxo-1,2,3,4,6,7,8,12b-octahydropyrido[2,1-a][2]benzazepine-4-carboxylic acid); AVE-7688 (ilepatril) and its parent compound; BMS-182657 (2-[2-oxo-3(S)-[3-phenyl-2(S)-sulfanylpropionamido]-2,3,4,5-tetrahydro-1H-1-benzazepin-1-yl]acetic acid); CGS-26303 ([N-[2-(biphenyl-4-yl)-1(S)-(1H-tetrazol-5-yl)ethyl]amino]methylphosphonic acid); CGS-35601 (N-[1-[4-methyl-2(S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8,12b-octahydropyrido[2,1-a][2]benzazepine-4-carboxylic acid); MDL-101287 ([4S-[4α,7α(R*),12bβ]]-7-[2-(carboxymethyl)-3-phenylpropionamido]-6-oxo-1,2,3,4,6,7,8,12b-octahydropyrido[2,1-a][2]benzazepine-4-carboxylic acid); omapatrilat; RB-105 (N-[2(S)-(mercaptomethyl)-3(R)-phenylbutyl]-L-alanine); sampatrilat; SA-898 ((2R,4R)—N-[2-(2-hydroxyphenyl)-3-(3-mercaptopropionyl)thiazolidin-4-ylcarbonyl]-L-phenylalanine); Sch-50690 (N-[1(S)-carboxy-2-[N2-(methanesulfonyl)-L-lysylamino]ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine. Exemplary vasopressin receptor antagonists include tolvaptan.

The following formulations illustrate representative pharmaceutical compositions of the invention.

Exemplary Hard Gelatin Capsules for Oral Administration

A compound of the invention (50 g), 440 g spray-dried lactose, and 10 g magnesium stearate are thoroughly blended. The resulting composition is then loaded into hard gelatin capsules to provide 500 mg of composition per capsule. Alternately, 20 mg of a compound of the invention is thoroughly blended with 89 mg starch, 89 mg microcrystalline cellulose, and 2 mg magnesium stearate. The mixture is then passed through a No. 45 mesh U.S. sieve and loaded into a hard gelatin capsule having 200 mg of composition per capsule.

Exemplary Gelatin Capsule Formulation for Oral Administration

A compound of the invention (100 mg) is thoroughly blended with 50 mg polyoxyethylene sorbitan monooleate and 250 mg starch powder. The mixture is then loaded into a gelatin capsule to provide 300 mg of composition per capsule. Alternately, 40 mg of a compound of the invention is thoroughly blended with 260 mg microcrystalline cellulose (Avicel PH 103) and 0.8 mg magnesium stearate. The mixture is then loaded into a gelatin capsule (Size #1, White, Opaque) having 300 mg of composition per capsule.

Exemplary Tablet Formulation for Oral Administration

A compound of the invention (10 mg), 45 mg starch, and 35 mg microcrystalline cellulose are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with 4.5 mg sodium carboxymethyl starch, 0.5 mg magnesium stearate, and 1 mg talc, and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, 250 mg of a compound of the invention is thoroughly blended with 400 mg microcrystalline cellulose, 10 mg silicon dioxide (fumed), and 5 mg stearic acid. The mixture is then compressed to form tablets having 665 mg of composition per tablet.

Alternately, 400 mg of a compound of the invention is thoroughly blended with 50 mg cornstarch, 25 mg croscarmellose sodium, 120 mg lactose, and 5 mg magnesium stearate. The mixture is then compressed to form a single-scored tablet having 600 mg of composition per tablet.

Alternately, 100 mg of a compound of the invention is thoroughly blended with 100 mg cornstarch and an aqueous solution of gelatin (20 mg). The mixture is dried and ground to a fine powder. Microcrystalline cellulose (50 mg) and 5 mg magnesium stearate are the admixed with the gelatin formulation, granulated and the resulting mixture compressed to form tablets having 100 mg of active agent per tablet.

Exemplary Suspension Formulation for Oral Administration

The following ingredients are mixed to form a suspension containing 100 mg of active agent per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous HCL or 0.5 N aqueous NaOH, as necessary, and then sufficient water for injection is added to provide a total volume of 20 mL. The mixture is then filtered through a sterile 0.22 µm filter to provide a sterile solution suitable for administration by injection.

Exemplary Compositions for Administration by Inhalation

A compound of the invention (0.2 mg) is micronized and then blended with 25 mg lactose. This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving 0.2 g lecithin in 200 mL demineralized water. The resulting suspension is spray dried and then micronized to form a micronized composition comprising particles having a mean diameter less than about 1.5 p.m. The micronized composition is then loaded into metered-dose inhaler cartridges containing pressurized 1,1,1,2-tetrafluoroethane in an amount sufficient to provide about 10 µg to about 500 µg of active agent per dose when administered by the inhaler.

Alternately, 25 mg of a compound of the invention is dissolved in 125 mL citrate buffered (pH 5) isotonic saline. The mixture is stirred and sonicated until the compound is dissolved. The pH of the solution is checked and adjusted, if necessary, to pH 5 by slowly adding aqueous 1N NaOH. The solution is administered using a nebulizer device that provides about 10 µg to about 500 µg of active agent per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard meaning:
ACE angiotensin converting enzyme
AcOH acetic acid
APP aminopeptidase P
$AT_1$ angiotensin II type 1 (receptor)
$AT_2$ angiotensin II type 2 (receptor)
BCA bicinchoninic acid
BOP benzotriazol-1-yloxytris(dimethylamino)phosphonium hexafluorophosphate
BSA bovine serum albumin
DCM dichloromethane (methylene chloride)
DIPEA N,N-diisopropylethylamine
DMF dimethylformamide
DMSO dimethyl sulfoxide
Dnp 2,4-dinitrophenyl
DOCA deoxycorticosterone acetate
EDTA ethylenediaminetetraacetic acid
EGTA ethylene glycol bis((β-aminoethyl ether)-N,N,N'N'-tetraacetic acid
EtOAc ethyl acetate
EtOH ethanol
HATU O-(7-azabenzotriazol-1-yl-N,N,N',N'-tetramethyluronium hexafluorophosphate
Mca (7-methoxycoumarin-4-yl)acyl
MeOH methanol
NBS N-bromosuccinimide
NEP neprilysin (EC 3.4.24.11)
PBS phosphate buffered saline
SHR spontaneously hypertensive rat
TFA trifluoroacetic acid
THF tetrahydrofuran
Tris tris(hydroxymethyl)aminomethane
Tween-20 polyethylene glycol sorbitan monolaurate Any other abbreviations used herein but not defined have their standard, generally accepted meaning. Unless noted otherwise, all materials, such as reagents, starting materials and solvents, were purchased from commercial suppliers (such as Sigma-Aldrich, Fluka Riedel-de Haën, and the like) and were used without further purification.

Preparation 1

5-(4'-Bromomethylbiphenyl-2-yl)-1-trityl-1H-tetrazole

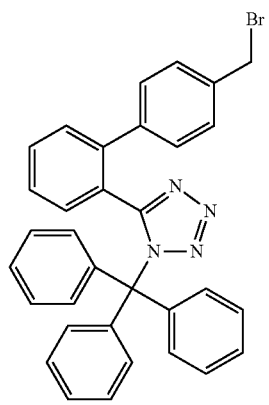 [SMILES: BrCc1ccc(-c2ccccc2-c2nnnn2C(c2ccccc2)(c2ccccc2)c2ccccc2)cc1]

To a nitrogen-saturated suspension of N-triphenylmethyl-5-[4'-methylbiphenyl-2-yl]tetrazole (10 g, 20.9 mmol) in DCM was added NBS (3.7 g, 20.9 mmol) and a catalytic amount of benzoyl peroxide (60 mg, 0.2 mmol). The mixture was stirred at reflux for 15 hours. After cooling to room temperature, the precipitate was filtered and the organic solution was concentrated in vacuo. Silica gel chromatography (EtOAc/hexane) gave the title compound as a white solid.

$^1$H-NMR (400 MHz, DMSO-$d_6$): δ (ppm) 4.61 (s, 2H), 6.80 (d, 6H), 7.01 (d, 2H), 7.24 (d, 2H), 7.28-7.35 (m, 9H), 7.43-7.45 (dd, 1H), 7.50-7.56 (td, 1H), 7.58-7.60 (td, 1H), 7.77-7.79 (dd, 1H).

Example 1

2-Mercaptomethyl-4-methylpentanoic Acid (2-Butyryl-[2'-(1H-tetrazol-5-yl)biphenyl-4-ylmethyl]aminoethyl)amide

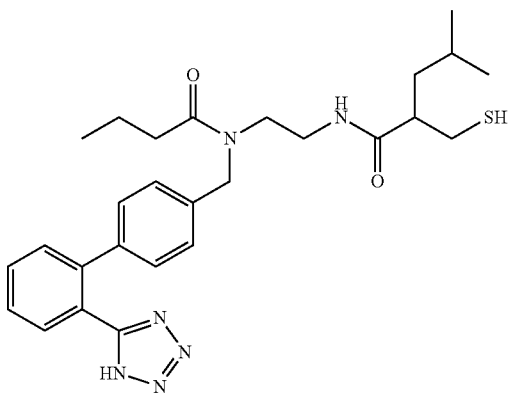 [SMILES: CCCC(=O)N(CCNC(=O)C(CS)CC(C)C)Cc1ccc(-c2ccccc2-c2nnn[nH]2)cc1]

(2-[2'-(1-Trityl-1H-tetrazol-5-yl)biphenyl-4-ylmethyl] aminoethyl)carbamic acid t-butyl ester (1a): A solution of 5-(4'-bromomethylbiphenyl-2-yl)-1-trityl-1H-tetrazole made as described in Preparation 1 (23.2 g, 41.6 mmol), N-(2-aminoethyl)(t-butoxy)carboxamide (20 g, 125 mmol), and potassium carbonate (8.6 g, 62.4 mmol) in THF (100 mL) was stirred at room temperature for 48 hours. The mixture was concentrated in vacuo and extracted with 1M aqueous KOH (20 mL) and EtOAc (2×200 mL). The combined organic extracts were dried over $Na_2SO_4$, filtered, and concentrated in vacuo. Intermediate (1a) was used without further purification.

(2-Butyryl-[2'-(1-trityl-1H-tetrazol-5-yl)biphenyl-4-ylmethyl]aminoethyl)carbamic acid t-butyl ester (1b) and N-(2-aminoethyl)-N-[2'-(1H-tetrazol-5-yl)biphenyl-4-ylmethyl] butyramide as the TFA salt (1c): Butyryl chloride (1.5 mL, 14.8 mmol) was added to a solution of intermediate (1a) (8.6 g, 13.5 mmol) in toluene (70 mL) at 0° C. followed by the addition of DIPEA (7.1 mL, 40.5 mmol). The mixture was stirred for 1 hour at room temperature. 1M aqueous NaOH (10 mL) was added and the solution concentrated in vacuo. The concentrate was extracted with EtOAc (2×100 mL) and water (75 mL). The combined organic extracts were dried over $Na_2SO_4$, filtered, and concentrated in vacuo to afford intermediate (1b). A solution of intermediate (1b), 1,4-dioxane (50 mL) and 4M HCl in 1,4-dioxane (50 mL) was stirred at room temperature for 3 hours. The precipitate was filtered and purified by reverse phase HPLC to afford intermediate (1c) (22% yield).

Thioacetic acid S-[2-(2-butyryl-[2'-(1H-tetrazol-5-yl)biphenyl-4-ylmethyl]aminoethylcarbamoyl)-4-methylpentyl] ester (1d) and title compound: BOP (305 mg, 0.7 mmol) was added to a solution of intermediate (1c) (300 mg), 2-acetylsulfanylmethyl-4-methylpentanoic acid (141 mg, 0.7 mmol), and DIPEA (0.15 mL) in DMF (4 mL) at room temperature. After 5 minutes, DIPEA (0.13 mL) was added and the solution was stirred overnight. The mixture was concentrated in vacuo to afford the crude intermediate (1d), which was then dissolved in MeOH (2 mL), 1M aqueous NaOH (2 mL) and 6M aqueous NaOH (0.4 mL) under nitrogen at room temperature. After 3 hours, the mixture was neutralized with 6M aqueous HCl and was concentrated in vacuo. Reverse phase HPLC gave the title compound (75% yield). MS m/z: [M+H$^+$] calcd for $C_{27}H_{36}N_6O_2S$, 509.26. found, 509.2.

$^1$H NMR (CDCl$_3$) δ (ppm) 0.8-1.0 (m, 6H), 1.0-1.1 (m, 3H), 1.2-1.3 (m, 1H), 1.4-1.5 (m, 3H), 1.7-1.9 (m, 2H), 2.2-2.3 (m, 1H), 2.5-2.7 (m, 6H), 3.5-3.7 (m, 2H), 4.5-4.7 (m, 2H), 7.1-7.2 (m, 3H), 7.2-7.3 (m, 2H), 7.5-7.7 (m, 3H), 7.9 (d, 1H).

Example 2

N-Hydroxy-2-isobutyl-N'-(2-{pentanoyl[2'-(1H-tetrazol-5-yl)biphenyl-4-ylmethyl]amino}ethyl)malonamide

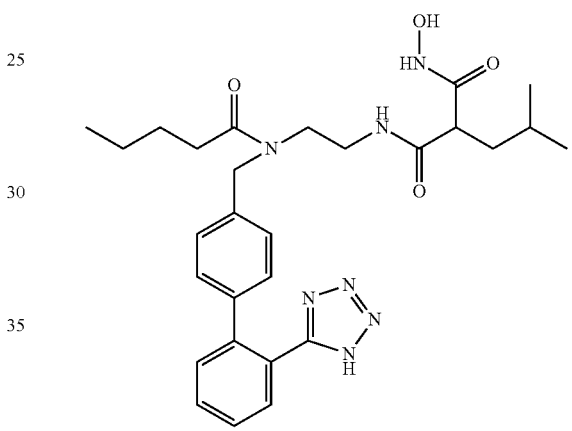

(2-[2'-(1-Trityl-1H-tetrazol-5-yl)biphenyl-4-ylmethyl] aminoethyl)carbamic acid t-butyl ester (2a): A solution of 5-(4'-bromomethylbiphenyl-2-yl)-1-trityl-1H-tetrazole made as described in Preparation 1 (20.9 g, 37.4 mmol), N-(2-aminoethyl)(t-butoxy) carboxamide (15 g, 93.6 mmol), and potassium carbonate (10.4 g, 74.9 mmol) in THF (150 mL) was stirred overnight at room temperature. The solvent was removed in vacuo and extracted with 1M aqueous KOH (70 mL) and DCM (3×200 mL). The combined organic extracts were dried over MgSO$_4$, filtered, and concentrated in vacuo. The crude intermediate (2a) was used in the next step.

(2-Pentanoyl-[2'-(1-trityl-1H-tetrazol-5-yl) biphenyl-4-ylmethyl]aminoethyl) carbamic acid t-butyl ester (2b): Valeryl chloride (1.4 mL, 12.2 mmol) was added to a solution of intermediate (2a) (7.1 g, 11.1 mmol) in toluene (80 mL) at 0° C. followed by the addition of DIPEA (5.8 mL, 33.2 mmol). After 2 hours at room temperature, 1M aqueous NaOH (20 mL) was added and the mixture was concentrated in vacuo. The concentrate was extracted with EtOAc (2×100 mL) and water (50 mL). The combined organic extracts were dried over MgSO$_4$ and concentrated in vacuo (75.3% yield). The crude intermediate (2b) was used in the next step.

Pentanoic acid (2-aminoethyl)-[2'-(1H-tetrazol-5-yl)biphenyl-4-ylmethyl]amide as the TFA salt (2c): A solution of the crude intermediate (2b) (6.5 g, 9 mmol) in 1,4-dioxane (50 mL) and 4M HCl in 1,4-dioxane (50 mL) was stirred at room temperature for 4 hours. The precipitate was filtered and purified by reverse phase HPLC to afford intermediate (2c) (81.8% yield).

N-(2,2-Dimethyl-1-propionyloxy)-2-isobutyl-N-(2-{pentanoyl[2'-(1H-tetrazol-5-yl)biphenyl-4-ylmethyl]amino}ethyl)malonamide (2d): HATU (46 mg) was added to intermediate (2c) (50 mg), 2-(2,2-dimethylpropionyloxycarbamoyl)-4-methyl pentanoic acid (31 mg), and DIPEA (0.02 mL) in DMF (1 mL), and was stirred at room temperature for 10 minutes. DIPEA (0.02 mL) was added and the mixture was stirred overnight. The mixture was concentrated and crude intermediate (2d) was used in the next step.

Title compound: Intermediate (2d) in MeOH (1 mL), 1M aqueous NaOH (1 mL), and 6M aqueous NaOH (0.3 mL) was stirred under nitrogen overnight. The mixture was neutralized with 6M aqueous HCl and concentrated in vacuo. Reverse phase HPLC gave the title compound. MS m/z: [M+H$^+$] calcd for $C_{28}H_{37}N_7O_4$, 536.29. found 536.4.

Preparation 2

4'-Bromomethylbiphenyl-2-carboxylic Acid t-Butyl Ester

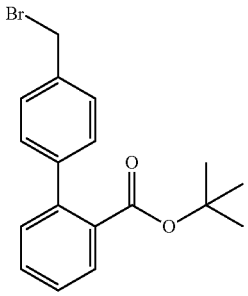 [SMILES: CC(C)(C)OC(=O)c1ccccc1-c1ccc(CBr)cc1]

A solution of 4'-methylbiphenyl-2-carboxylic acid (48.7 g, 230 mmol) and thionyl chloride (150 mL) was stirred at room temperature. After 5.5 hours, the mixture was concentrated in vacuo. Excess thionyl chloride was removed by co-distillation with toluene to afford a yellow solid (52.6 g). The material was then dissolved in THF (500 mL) and cooled to 0° C. Potassium t-butoxide (15 g, 130 mmol) was added portion wise, followed by a 1M solution of potassium t-butoxide in THF (250 mL). Additional solid potassium t-butoxide (21.4 g, 100 mmol) was added and the mixture was stirred at 0° C. for 1.5 hours. The mixture was partitioned between EtOAc and water. The organic layer was washed with saturated aqueous NaCl, dried over MgSO$_4$, filtered, and concentrated to afford 4'-methylbiphenyl-2-carboxylic acid t-butyl ester (62.3 g) as a yellow oil, which was used directly in the next step.

Benzoyl peroxide (3.9 g, 16 mmol) was added to a solution of the above oil (62 g, 230 mmol) in benzene (800 mL) and NBS (41.2 g, 230 mmol) and was heated at reflux. After 4.5 hours, benzoyl peroxide (1 g) was added, followed by NBS (16 g, 66 mmol) 30 minutes later. The mixture was stirred for a total of 6 hours and then cooled, filtered, and concentrated in vacuo. The resulting residue was then crystallized from diethyl ether and hexane at 4° C. overnight to give the title compound (40.7 g) as a pale yellow solid.

$^1$H NMR (DMSO) δ (ppm) 1.1 (s, 9H), 4.6 (s, 2H), 7.1-7.6 (m, 8H).

Example 3

4'-({[2-(2-Mercaptomethyl-3-phenylpropionylamino)ethyl]pentanoylamino}methyl)biphenyl-2-carboxylic Acid (3-1; R$^6$=benzyl) and 4'-({[2-(2-Mercaptomethyl-4-methylpentanoylamino) ethyl]pentanoylamino}methyl)biphenyl-2-carboxylic Acid (3-2; R$^6$=i-butyl)

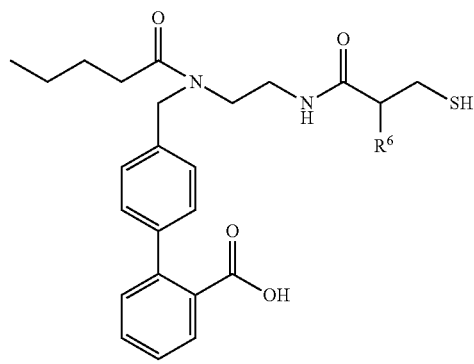

4'-[(2-t-Butoxycarbonylaminoethylamino)methyl]biphenyl-2-carboxylic acid t-butyl ester (3a): A solution of 4'-bromomethylbiphenyl-2-carboxylic acid t-butyl ester made as described in Preparation 2 (7.2 g, 20.8 mmol), N-(2-aminoethyl)(t-butoxy)carboxamide (10 g, 62.4 mmol), and potassium carbonate (4.3 g, 31.2 mmol) in THF (40 mL) was stirred at room temperature overnight. The mixture was concentrated then extracted with EtOAc (3×150 mL) and water (80 mL). The combined organic extracts were dried over Na$_2$SO$_4$, filtered, and concentrated in vacuo to afford crude intermediate (3a) (98.4% yield), which was used in the next step without further purification.

4'-[(2-t-Butoxycarbonylaminoethyl)pentanoylamino]methylbiphenyl-2-carboxylic acid t-butyl ester (3b) and 4'[(2-aminoethyl)pentanoylamino]methylbiphenyl-2-carboxylic acid (3c): Valeryl chloride (4.6 mL, 38.7 mmol) was added to a solution of crude intermediate (3a) (15 g, 35.2 mmol) in toluene (100 mL) at 0° C. followed by the addition of DIPEA (18.4 mL, 105 mmol). The mixture was stirred at room temperature for 3 hours. 1M aqueous NaOH (10 mL) was added and the mixture was concentrated in vacuo. The concentrate was extracted with EtOAc (3×150 mL) and water (80 mL). The organic extracts were dried over Na$_2$SO$_4$, filtered, and concentrated in vacuo to afford crude intermediate (3b). A solution of crude intermediate (3b), 1,4-dioxane (50 mL) and 4M HCl in 1,4-dioxane (50 mL) was stirred for 40 minutes at room temperature. The precipitate was filtered and purified by reverse phase HPLC to afford intermediate (3c).

Title compounds (3-1) and (3-2): In two separate vials. HATU (47.2 mg, 124 μmol) was added to a solution of 2-acetylsulfanylmethyl-4-methylpentanoic acid (25.4 mg, 124 μmol) or 2-acetylsulfanylmethyl-3-phenylpropionic acid (29.6 mg, 124 μmol) in DMF (0.3 ml) and DIPEA (27 μL). The solutions were stirred at room temperature for 15 minutes before the addition of a solution of intermediate (3c) (40 mg, 0.1 mmol) in DMF (0.3 mL) to each solution. The solutions were stirred for a further 3 hours. The solutions were concentrated in vacuo to afford intermediates, which were each dissolved in MeOH (1 mL), 1M aqueous NaOH (1 mL), and 6M aqueous NaOH (0.2 mL) in two separate vials. The mixtures were stirred at room temperature under nitrogen for 3 hours. The mixtures were neutralized with 6M aqueous HCl and concentrated in vacuo. Reverse phase HPLC gave the title compounds:

(3-1) MS m/z: [M+H$^+$] calcd for $C_{31}H_{36}N_2O_4S$, 533.24. found 533.2; and (3-2) MS m/z: [M+H$^+$] calcd for $C_{28}H_{38}N_2O_4S$, 499.26. found 499.2.

Example 4

4-({[2-(2-Mercaptomethyl-3-phenylpropionylamino) ethyl]pentanoylamino}methyl)benzoic Acid (4-1; $R^5$=—$CH_2SH$; $R^6$=benzyl), 4-({[2-((S)-2-mercapto-3-phenylpropionylamino) ethyl]pentanoylamino methyl}yl)benzoic Acid (4-2; $R^5$=—SH; $R^6$=benzyl), 4-({[2-(3-Mercaptomethyl-4-methyl-pentanoylamino)ethyl]pentanoylamino}methyl)benzoic Acid (4-3; $R^5$=—$CH_2SH$; $R^6$=i-butyl), 4-({[2-(2-Mercaptomethyl-3-methylbutyrylamino)ethyl] pentanoylamino}methyl)benzoic Acid (4-4; $R^5$= —$CH_2SH$; $R^6$=i-propyl), and 4-({[2-(3-Mercapto-2-methylpropionylamino)ethyl] pentanoylamino}methyl)benzoic Acid (4-5; $R^5$= —$CH_2SH$; $R^6$=methyl)

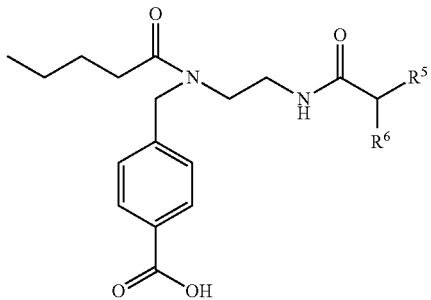

4-{[(2-t-Butoxycarbonylaminoethylamino)methylbenzoic acid methyl ester (4a): A solution of methyl 4-bromomethylbenzoate (10 g), N-(2-aminoethyl)(t-butoxy) carboxamide (28 g), and potassium carbonate (9.1 g) in THF (200 mL) was stirred at room temperature overnight. The mixture was concentrated and extracted with DCM (2×200 mL) and water (60 mL). The combined organic extracts were dried over $Na_2SO_4$, filtered, and concentrated in vacuo to afford the crude intermediate (4a) (87.8% yield), which was used without further purification.

4{[(2-t-Butoxycarbonylaminoethyl)pentanoylamino] methyl}benzoic acid methyl ester (4b) and 4-[(2-aminoethyl) pentanoylamino]methylbenzoic acid methyl ester as the TFA salt (4c): DIPEA (10.6 mL, 60.9 mmol) was added to a solution of the crude intermediate (4a) (6.3 g, 20.3 mmol) and valeryl chloride (2.7 mL, 22.3 mmol) in toluene (80 mL) at 0° C. The mixture was stirred for 3 hours at room temperature. 1M aqueous NaOH (5 mL) was added to the mixture at 0° C. and the resulting solution was concentrated in vacuo. The concentrate was extracted with EtOAc (3×70 mL) and water (40 mL). The combined organic extracts were dried over $MgSO_4$, filtered, and concentrated in vacuo giving intermediate (4b) (87.8%). Intermediate (4b) (7g) was dissolved in 1,4-dioxane (50 mL) and 4M HCl in 1,4-dioxane (50 mL) at room temperature. After 3 hours, the precipitate was filtered. Reverse phase HPLC gave intermediate (4c) (54.1% yield).

Title compounds (4-1), (4-2), (4-3), (4-4) and (4-5): BOP (99.8 mg, 226 μmol) was added to a solution of intermediate (4c), DIPEA (0.1 mL) in DMF (1 mL), and either 2-acetylsulfanylmethyl-3-phenylpropionic acid (53.8 mg, 226 μmol), (S)-2-acetylsulfanyl-3-phenylpropionic acid (50.6 mg, 226 μmol), 2-acetylsulfanylmethyl-4-methylpentanoic acid (46.1 mg, 226 μmol), 2-acetylsulfanylmethyl-3-methylbutyric acid (42.9 mg, 226 μmol), or 3-acetylsulfanyl-2-methylpropionic acid (36.6 mg, 226 μmol), to 5 separate 20 mL vials at room temperature. Additional DIPEA (0.1 mL) was added to each vial after 5 minutes. After 3 hours, the mixtures were concentrated and each intermediate was used without further purification in the next step. The concentrate of each mixture was dissolved separately in MeOH (1 mL), 1M aqueous NaOH, and 6M aqueous NaOH (0.2 mL), and was stirred under an atmosphere of nitrogen for 4 hours. Each mixture was neutralized with 6M aqueous HCl and concentrated in vacuo. Reverse phase HPLC gave the title compounds:

(4-1) MS m/z: [M+H$^+$] calcd for $C_{25}H_{32}N_2O_4S$, 457.21. found 457.2;

(4-2) MS m/z: [M+H$^+$] calcd for $C_{24}H_{30}N_2O_4S$, 443.19. found 443.2;

(4-3) MS m/z: [M+H$^+$] calcd for $C_{22}H_{34}N_2O_4S$, 423.22. found 423.2;

(4-4) MS m/z: [M+H$^+$] calcd for $C_{21}H_{32}N_2O_4S$, 409.21. found 409.2; and (4-5) MS m/z: [M+H$^+$] calcd for $C_{19}H_{28}N_2O_4S$, 381.18. found 381.2.

Example 5

2-Mercaptomethyl-4-methylpentanoic Acid ((S)-2-{Butyryl[2'-(1H-tetrazol-5-yl) biphenyl-4-ylmethyl] amino}propyl)amide (5-1)

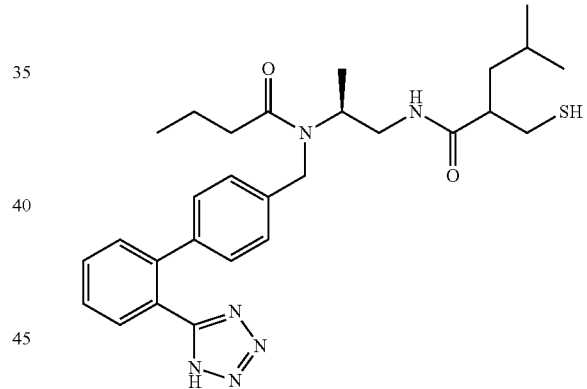

(S)-2-[2'-(1-Trityl-1H-tetrazol-5-yl)biphenyl-4-ylmethyl] aminopropan-1-ol (5a): A solution of 5-(4'-bromomethylbiphenyl-2-yl)-1-trityl-1H-tetrazole made as described in Preparation 1 (9.7 g, 17.4 mmol), (2S)-2-aminopropan-1-ol (3.9 g, 52.3 mmol), and potassium carbonate (2.4 g, 17.4 mmol), in THF (170 mL) was stirred at room temperature overnight. Water (100 mL) was added, and the aqueous phase was extracted with EtOAc (3×100 mL). The combined organic extracts were dried over $MgSO_4$, filtered, and concentrated in vacuo. Silica gel chromatography gave intermediate (5a).

N—((S)-2-Hydroxy-1-methylethyl)-N-[2'-(1-trityl-1H-tetrazol-5-yl)biphenyl-4-ylmethyl]butyramide (5b): Butyryl chloride (258 μL, 2.5 mmol) was added to a solution of intermediate (5a) (1.1 g, 2.1 mmol), and DIPEA (504 μL, 2.9 mmol) in toluene (20 mL) at 0° C. The solution was stirred at room temperature for 30 minutes. Water was added (20 mL), and the aqueous phase was extracted with EtOAc (3×30 mL). The combined organic extracts were washed with saturated aqueous NaCl, dried over MgSO$_4$, filtered, and concentrated in vacuo. Silica gel chromatography gave intermediate (5b) as a white solid (942 mg).

N—((S)-1-Methyl-2-oxoethyl)-N-[2'-(1-trityl-1H-tetrazol-5-yl)biphenyl-4-ylmethyl]butyramide (5c): Dess-Martin periodinane (971 mg, 2.3 mmol) was added to a solution of intermediate (5b) (474 mg, 0.8 mmol) in DCM (20 mL) at room temperature. After 30 minutes, water (20 mL) and saturated aqueous sodium thiosulfate (20 mL) was added. The mixture was extracted with DCM (3×30 mL), washed with saturated aqueous NaCl (20 mL), dried over MgSO$_4$, and concentrated in vacuo. Silica gel chromatography gave intermediate (5c) as a white solid (411 mg).

N—((S)-2-Hydroxyimino-1-methylethyl)-N-[2'-(1-trityl-1H-tetrazol-5-yl)-biphenyl-4-ylmethyl]butyramide (5d): Hydroxylamine hydrochloride (25.4 mg, 0.4 mmol) was added to a solution of intermediate (5c) (174 mg, 0.3 mmol), pyridine (3 mL, 37 mmol) and water (1.5 mL, 83 mmol) at room temperature. After 15 minutes, water (10 mL) was added and the mixture was extracted with EtOAc (3×20 mL). The combined organic extracts were washed with saturated aqueous NaCl (10 mL), dried over MgSO$_4$, filtered, and concentrated in vacuo. Silica gel chromatography gave intermediate (5d) as a white solid (148 mg).

N—((S)-2-Amino-1-methylethyl)-N-[2'-(1-trityl-1H-tetrazol-5-yl)biphenyl-4-ylmethyl]butyramide (5e): A solution of intermediate (5d) (105 mg, 0.2 mmol), sodium cyanoborohydride (47 mg, 0.7 mmol), ammonium acetate (28 mg, 0.4 mmol), and MeOH (6.0 mL) was cooled to 0° C. After 15 minutes, titanium (III) chloride (83 mg, 0.5 mmol) was added. After 10 minutes, ammonium hydroxide (1 mL) was added and the mixture was stirred at room temperature for 5 minutes. The mixture was filtered through Celite®, rinsing with MeOH, and the filtrate was concentrated in vacuo to yield a white solid. The solid was extracted with DCM and water. The combined organic extracts were washed with saturated aqueous NaCl, dried over MgSO$_4$, filtered, and concentrated in vacuo to afford intermediate (5e) (95 mg), which was used directly in the next step.

Thioacetic acid S-[2-((S)-2-butyryl-[2'-(1-trityl-1H-tetrazol-5-yl)biphenyl-4-ylmethyl]aminopropylcarbamoyl)-4-methylpentyl]ester (5f): BOP (74.4 mg, 0.2 mmol), followed by DIPEA (40.0 µL, 0.2 mmol) was added to a solution of intermediate (5e) (95 mg, 0.2 mmol), 2-acetylsulfanylmethyl-4-methyl-pentanoic acid (34.4 mg, 0.2 mmol) and DMF (4.0 mL, 51 mmol) at room temperature. After 20 minutes, the mixture was concentrated in vacuo. Silica gel chromatography gave intermediate (5f as a colorless oil (67 mg).

Title compound (5-1): A solution of intermediate (5f) (34 mg, 42 µmol), MeOH (1.0 mL), and 1.0 M aqueous HCl (0.3 mL) was stirred under an atmosphere of nitrogen at room temperature. After 30 minutes, 1M aqueous NaOH (1.3 mL), and 6M aqueous NaOH (0.2 mL) was added. After 90 minutes, the mixture was neutralized with 6.0 N HCl and concentrated in vacuo. Reverse phase HPLC gave compound (5-1) as a white solid (7.8 mg). MS m/z: [M+H$^+$] calcd for C$_{28}$H$_{38}$N$_6$O$_2$S, 523.28. found 523.4.

2-Mercaptomethyl-4-methylpentanoic acid ((S)-2-{butyryl[2'-(1H-tetrazol-5-yl)biphenyl-4-ylmethyl]amino}-3-methylbutyl)amide (5-2) was made in a similar manner. MS m/z: [M+H$_+$] calcd for C$_{30}$H$_{42}$N$_6$O$_2$S, 551.31. found 551.4.

Example 6

Thioacetic Acid S-[3-methyl-1-(2-{pentanoyl-[2'-(1H-tetrazol-5-yl)-biphenyl-4-ylmethyl]amino}ethylcarbamoyl)butyl]ester (6-1; R$^5$=—S—C(O)—CH) and 2-Mercapto-4-methylpentanoic Acid (2-{pentanoyl[2'-(1H-tetrazol-5-yl)biphenyl-4-ylmethyl]amino}ethyl)amide (6-2; R$^5$=—SH)

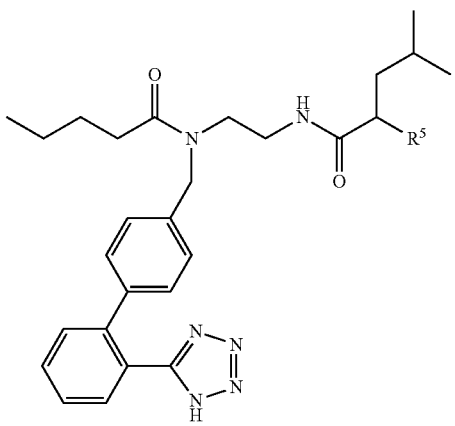

(2-[2'-(1-Trityl-1H-tetrazol-5-yl)-biphenyl-4-ylmethyl]aminoethyl)carbamic acid t-butyl ester (6a): A solution of 5-(4'-bromomethylbiphenyl-2-yl)-1-trityl-1H-tetrazole (20.9 g, 37.4 mmol) made as described in Preparation 1, N-(2-aminoethyl)(t-butoxy) carboxamide (15 g, 93.6 mmol), and potassium carbonate (15.5 g, 112 mmol) in THF (75 mL) was stirred at room temperature for 48 hours. The mixture was concentrated and extracted with 1M aqueous KOH (20 mL) and EtOAc (2×200 mL). The combined organic extracts were dried over Na$_2$SO$_4$, filtered, and concentrated in vacuo. Intermediate (6a) was used without further purification.

(2-Pentanoyl-[2'-(1-trityl-1H-tetrazol-5-yl)biphenyl-4-ylmethyl]aminoethyl) carbamic acid t-butyl ester (6b) and pentanoic acid (2-aminoethyl)-[2'-(1H-tetrazol-5-yl)biphenyl-4-ylmethyl]amide (6c): Valeryl chloride (1.4 mL, 11.9 mmol) was added to a solution of intermediate (6a) (6.9 g, 10.8 mmol) in toluene (70 mL) at 0° C. followed by DIPEA (3.8 mL, 21.6 mmol). After 3 hours at room temperature, 1M aqueous NaOH (5 mL) was added and the solvent was removed in vacuo. The concentrate was extracted with EtOAc and water. The combined organic fractions were dried over Na$_2$SO$_4$, filtered, and concentrated in vacuo to afford intermediate (6b). A solution of intermediate (6b) in 1,4-dioxane (30 mL) and 4M HCl (30 mL), and was stirred at room temperature for 1 hour. The precipitate was filtered and purified by reverse phase HPLC to afford (6c) as a TFA salt.

Title compounds (6-1) and (6-2): A solution of HATU (127 mg, 0.3 mmol), α-bromoisocaproic acid (51.3 µL, 340 µmol), and DIPEA (53 µL) was dissolved in DMF (2.5 mL) at room temperature. After 15 minutes, a solution of intermediate (6c) (150 mg) and DIPEA (53 µL, 1 eq) in DMF (2.5 mL) was added. After 10 minutes, potassium thioacetate (243 mg, 2.1 mmol) was added. After 20 minutes, water (5 mL) was added and the mixture was extracted with EtOAc (3×15 mL), washed with saturated aqueous NaCl (2×5 mL), dried over Na$_2$SO$_4$, filtered and concentrated in vacuo. Reverse phase HPLC gave the title compound (6-1). Compound (6-1) was dissolved in MeOH (4 mL), 1N NaOH (4 mL), and 6N NaOH (0.2 mL), under an atmosphere of nitrogen. After 90 minutes, the mixture was neutralized with 6M aqueous HCl, and was concentrated in vacuo. Reverse phase HPLC gave title compound (6-2) (50.8 mg).

(6-1) MS m/z: [M+H$^+$] calcd for C$_{29}$H$_{38}$N$_6$O$_3$S, 551.27. found 551.2; and (6-2) MS m/z: [M+H$^+$] calcd for C$_{27}$H$_{36}$N$_6$O$_2$S, 509.26. found 509.5.

Preparation 3

3-Methylpentanoyl Chloride

Thionyl chloride (4.7 mL, 64.6 mmol) was added to a solution of 3-methylpentanoic acid (2.5 g, 21.5 mmol) in DCM (10 mL) at room temperature. After stirring overnight, the solvent was removed in vacuo to afford the crude title compound as a colorless oil (2.7 g).

Preparation 4

Cyclopropylacetyl Chloride

Thionyl chloride (1.1 mL, 15 mmol) was added to a solution of cyclopropylacetic acid (0.5 g, 5 mmol) in DCM (2.3 mL, 35.1 mmol). The mixture was stirred at room temperature overnight, then concentrated to afford the crude title compound (0.4 g).

Preparation 5

4-Methylpentanoyl Chloride

Thionyl chloride (4.8 mL, 66.4 mmol) was added to a solution of isocaproic acid (2.6 g, 22.1 mmol) in DCM (10 mL, 156 mmol) at room temperature and was stirred overnight. Thionyl chloride was removed in vacuo to give the crude title compound (2.9 g) as a colorless oil.

Example 7

2-Mercaptomethyl-4-methylpentanoic Acid (2-{(3-Methylpentanoyl)[2'-(1H-tetrazol-5-yl)biphenyl-4-ylmethyl]amino}ethyl)amide (7-1; $R^3$=—$CH_2$—$CH(CH_3)CH_2CH_3$), 2-Mercaptomethyl-4-methylpentanoic Acid (2-{(2-cyclopropylacetyl)[2'-(1H-tetrazol-5-yl)biphenyl-4-ylmethyl]amino}ethyl)amide (7-2; $R^3$=—$CH_2$-cyclopropyl), 2-Mercaptomethyl-4-methylpentanoic Acid (2-{(4-Methylpentanoyl)[2'-(1H-tetrazol-5-yl)biphenyl-4-ylmethyl]amino}ethyl)amide (7-3; $R^3$=—$(CH_2)_2$—$CH(CH_3)_2$), and 2-Mercaptomethyl-4-methylpentanoic Acid (2-{(3-Methylbutyryl)[2'-(1H-tetrazol-5-yl)biphenyl-4-ylmethyl]amino}ethyl)amide (7-4; $R^3$=—$CH_2$—$CH(CH_3)_2$)

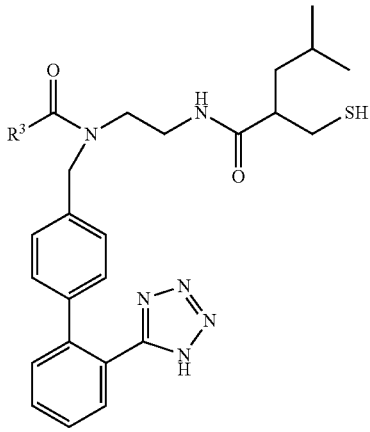

(2-[2'-(1-Trityl-1H-tetrazol-5-yl)biphenyl-4-ylmethyl]aminoethyl)carbamic acid t-butyl ester (7a): A solution of 5-(4'-bromomethylbiphenyl-2-yl)-1-trityl-1H-tetrazole made as described in Preparation 1 (20.9 g, 40 mmol), N-(2-aminoethyl)(t-butoxy) carboxamide (15 g, 90 mmol), and potassium carbonate (15.5 g, 110 mmol) in THF (75 mL) was stirred for 48 hours at room temperature. The mixture was concentrated and extracted with 1M aqueous KOH (20 mL) and EtOAc (2×200 mL). The combined organic extracts were dried over $Na_2SO_4$, filtered, and concentrated. Silica gel chromatography (EtOAc:hexanes) gave intermediate (7a) as a white solid (12.7 g).

(2-{Benzyloxycarbonyl-[2'-(1-trityl-1H-tetrazol-5-yl)biphenyl-4-ylmethyl]amino}ethyl)carbamic acid t-butyl ester (7b): Intermediate (7a) (3.3 g, 5.2 mmol) was dissolved in DCM and cooled to 0° C. DIPEA (2.7 mL, 15.6 mmol) was added, followed by benzyl chloroformate (804 µL, 5.7 mmol). After 90 minutes, water (20 mL) was added and the mixture was extracted DCM (3×80 mL) then washed with saturated aqueous NaCl. The combined organic extracts were dried over $MgSO_4$, filtered, and concentrated in vacuo to afford intermediate (7b) as a white solid (4.6 g).

(2-Aminoethyl)-[2'-(1H-tetrazol-5-yl)biphenyl-4-ylmethyl]carbamic acid benzyl ester as the TFA salt (7c): A solution of intermediate (7b), 1,4-dioxane (46 mL), and 4M HCl in 1,4-dioxane (46 mL) was stirred at room temperature. After 2 hours, the solvent was removed in vacuo. Reverse phase HPLC gave intermediate (7c) (2.1 g).

Thioacetic acid S-[2-(2-benzyloxycarbonyl-[2'-(1H-tetrazol-5-yl)biphenyl-4-ylmethyl]aminoethylcarbamoyl)-4-methylpentyl]ester (7d): A solution of intermediate (7c) (2.1 g) in DMF (10 mL) was added to a solution of 2-acetylsulfanylmethyl-4-methylpentanoic acid (1 g, 5 mmol) and DIPEA (1.2 mL, 6.9 mmol) in DMF (20 mL) at room temperature. BOP (2.2 g, 5.1 mmol) was added, followed by DIPEA (1.2 mL, 6.9 mmol). After 2 hours, the solvent was removed in vacuo. Silica gel chromatography gave intermediate (7d) (953 mg).

Thioacetic acid S-[4-methyl-2-(2-[2'-(1H-tetrazol-5-yl)-biphenyl-4-ylmethyl]aminoethylcarbamoyl)pentyl]ester as the TFA salt (7e): Iodotrimethylsilane (2 mL, 14 mmol) was added to a solution of intermediate (7d) (2.2 g, 3.5 mmol) in DCM (35 mL) at room temperature under an atmosphere of nitrogen. After stirring overnight, the solvent was removed in vacuo. Reverse phase HPLC gave intermediate (7e) as a white solid (1.7 g).

Title compounds (7-1), (7-2), (7-3) and (7-4): In 4 separate vials, intermediate (7e) (60 mg, 101 µmol) was dissolved in THF (1 mL, 12.3 mmol). Into each mixture was added 3-methylpentanoyl chloride (15.2 µL, 111 µmol) made as described in Preparation 3, or cyclopropylacetyl chloride (12.4 µL, 111 µmol) made as described in Preparation 4, 4-methylpentanoyl chloride (15.2 µL, 111 µmol) made as described in Preparation 5, or isovaleryl chloride (13.5 µL, 111 µmol). Into each mixture was added DIPEA (52.7 µL, 0.3 mmol) at room temperature. After 2 hours, to each mixture was added 0.33 eq of the respective acid chloride. After 15 minutes, the solvent was removed in vacuo. Each crude mixture was dissolved in MeOH (1 mL), 1M aqueous NaOH (1 mL), and 6M aqueous NaOH (0.2 mL) under an atmosphere of nitrogen at room temperature. After 90 minutes, each mixture was neutralized with 6M aqueous HCl, and concentrated in vacuo. Reverse phase HPLC gave the title compounds:

(7-1) 20.1 mg, 100% purity; MS m/z: [M+H$^+$] calcd for $C_{29}H_{40}N_6O_2S$, 537.29. found 537.4;

(7-2) 21.3 mg, 99% purity; MS m/z: [M+H$^+$] calcd for $C_{28}H_{36}N_6O_2S$, 521.26. found 521.2;

(7-3) 24.0 mg, 100% purity; MS m/z: [M+H$^+$] calcd for $C_{29}H_{40}N_6O_2S$, 537.29. found 537.4; and (7-4) 24.4 mg, 100% purity; MS m/z: [M+H$^+$] calcd for $C_{28}H_{38}N_6O_2S$, 523.28. found 523.2.

Preparation 6

4'-Formylbiphenyl-2-sulfonic Acid t-Butylamide

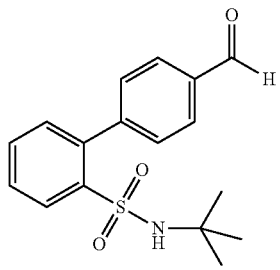 [SMILES: CC(C)(C)NS(=O)(=O)c1ccccc1-c1ccc(C=O)cc1]

2-Bromo-N-t-butylbenzenesulfonamide (6a): t-Butylamine (10 mL, 98 mmol), followed by DIPEA (19 mL, 110 mmol) was added to a solution of 2-bromobenzenesulfonyl chloride (25 g, 98 mmol) in DCM (210 mL) at 0° C. The mixture was allowed to warm to room temperature and was stirred overnight. The mixture was then extracted with 1M aqueous HCl (2×80 mL), followed by saturated aqueous NaHCO$_3$ (80 mL) and saturated aqueous NaCl (80 mL). The organic phase was dried over Na$_2$SO$_4$, filtered, and concentrated in vacuo. Crystallization from EtOAc and hexane afforded intermediate (6a) (21.5 g). MS m/z: [M+H$^+$] calcd 292.19. found 292.0.

A solution of intermediate (6a) (10 g, 30 mmol), 4-formylphenylboronic acid (6.2 g, 41 mmol), tetrakis(triphenylphosphine)palladium(0) (2 g, 2 mmol), potassium carbonate (9.5 g, 68.4 mmol), water (30 mL), EtOH (74 mL), and toluene (150 mL) was stirred overnight at 80° C. under nitrogen. The mixture was then concentrated in vacuo. The concentrate was extracted with EtOAc (3×200 mL) and 1M aqueous HCl (150 mL). The combined organic extracts were dried over Na$_2$SO$_4$, filtered, and concentrated in vacuo. The crude material was crystallized from EtOAc and hexane to afford the title compound (7.5 g).

Preparation 7

(S)-3-Acetylsulfanyl-2-benzylpropionic Acid

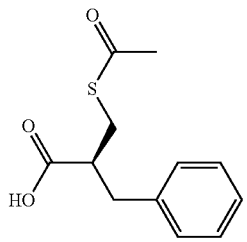 [SMILES: CC(=O)SC[C@@H](Cc1ccccc1)C(=O)O]

3-Phenylpropionyl chloride (7a): Thionyl chloride (21.8 mL, 300 mmol) was added to a solution of 3-phenylpropionic acid (15 g, 99.9 mol) in DCM (40 mL) and was stirred overnight. The mixture was concentrated in vacuo to yield intermediate (7a), which was used in the next step without further purification.

(S)-4-Benzyl-3-(3-phenylpropionyl)oxazolidin-2-one (7b): 1.6 M of n-Butyllithium in hexanes (35 mL) was added to a solution of (S)-4-benzyloxazolidin-2-one (10 g, 56.4 mmol) in THF (150 mL) at −78° C. After 15 minutes, intermediate (7a) (9.5 g, 56.4 mmol) in THF (20 mL) was added dropwise at −78° C. After 30 minutes, the mixture was allowed to warm to room temperature and was stirred overnight. The mixture was concentrated in vacuo and the crude material was extracted with EtOAc (3×200 mL) and water (100 mL). The combined organic extracts were dried over Na$_2$SO$_4$, filtered, and concentrated in vacuo to yield intermediate (7b), which was used in the next step without further purification.

(S)-4-Benzyl-3-((R)-2-hydroxymethyl-3-phenylpropionyl)-oxazolidin-2-one (7c): 1 M of titanium tetrachloride in DCM (43 mL) was added to a solution of intermediate (7b) (12.7 g, 41 mmol) in DCM (150 mL) at 0° C. under nitrogen. After 20 minutes, DIPEA (7.9 mL, 45.2 mmol) was added dropwise at 0° C. After 80 minutes, 1,3,5-trioxane (4.1 g, 45.2 mmol) in DCM (30 mL) was added, followed by a second equivalent of 1 M titanium tetrachloride in DCM after 10 minutes. After 2.5 hours at 0° C., the mixture was quenched with saturated aqueous NH$_4$Cl (150 mL). The product was extracted with water (100 mL) and DCM (3×200 mL). The combined organic extracts were dried over Na$_2$SO$_4$, filtered, and concentrated in vacuo to yield intermediate (7c), which was used in the next step without further purification.

(R)-2-Hydroxymethyl-3-phenylpropionic acid (7d): 9 M of Hydrogen peroxide in water (50 mL) was added to a solution of intermediate (7c) (14.8 g, 43.6 mmol) in THF (100 mL) at 0° C. followed by the addition of aqueous 1.5 M lithium hydroxide monohydrate (58 mL). After 2.5 hours at room temperature, sodium sulfite (10 g) in water (100 mL) was added and the mixture was stirred for 30 minutes. The mixture was extracted with water (300 mL) and chloroform (2×150 mL). The aqueous layer was acidified to pH2 with aqueous 6M HCl and extracted with EtOAc (3×200 mL). The combined organic extracts were dried over Na$_2$SO$_4$, filtered, and concentrated in vacuo to yield intermediate (7d), which was used in the next step without further purification.

Diisopropyl azodicarboxylate (14.8 mL, 75.2 mmol) was added to a solution of triphenylphosphine (19.7 g, 75.2 mmol) and THF (100 mL) at 0° C. After 10 minutes, a solution of thioacetic acid (8.1 mL, 113 mmol) and intermediate (7d) (6.8 g, 37.6 mmol) in THF (15 mL) was added dropwise to the mixture at 0° C. After 3.5 hours at room temperature, the mixture was concentrated and then extracted with saturated aqueous NaHCO$_3$ (2×200 mL) and EtOAc (150 mL). The aqueous layer was combined and acidified to pH2 with 6M aqueous HCl, then extracted with EtOAc (3×200 mL). The organic layer was dried over Na$_2$SO$_4$, filtered, and concentrated in vacuo. Silica gel chromatography (hexane:EtOAc (5% AcOH)) afforded the title compound (3.6 g).

Example 8

Pentanoic acid (2'-acetylsulfamoylbiphenyl-4-ylmethyl)-[2-((S)-2-benzyl-3-mercaptopropionylamino) ethyl]amide

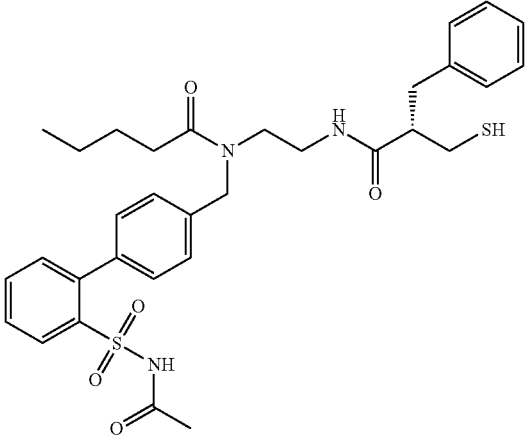 [SMILES: CCCCC(=O)N(CCNC(=O)[C@@H](CS)Cc1ccccc1)Cc1ccc(-c2ccccc2S(=O)(=O)NC(C)=O)cc1]

{2-[(2'-t-Butylsulfamoylbiphenyl-4-ylmethyl)amino] ethyl}carbamic acid t-butyl ester.C₂HF₃O₂ (8a): 4'-Formyl-biphenyl-2-sulfonic acid t-butylamide (5.8 g, 18 mmol; prepared as described in Preparation 6) was added to a solution of N-(2-aminoethyl)(t-butoxy)carboxamide (2.7 g, 16.6 mmol) in 1% AcOH in MeOH (40 mL), followed by the addition of sodium cyanoborohydride (1.2 g, 18.3 mmol). The mixture was concentrated in vacuo. Reverse phase HPLC afforded intermediate (8a) as a TFA salt (5.6 g). MS m/z: [M+H⁺] calcd 461.62. found 462.3.

Pentanoic acid (2-aminoethyl)-(2'-sulfamoylbiphenyl-4-ylmethyl)amide.C₂HF₃O₂ (8b): Valeryl chloride (394 μL, 3.3 mmol) was added to a solution of intermediate (8a) (1.8 g) and DIPEA (1.7 mL, 9.6 mmol) in toluene (9 mL) at 0° C. After stirring overnight, the mixture was concentrated in vacuo and extracted with EtOAc (2×100 mL) and 1M aqueous HCl (50 mL). The combined organic extracts were dried over Na₂SO₄, filtered, and concentrated in vacuo to afford the crude intermediate (8b). A solution of (8b) in DCM (5 mL) and TFA (12 mL) was heated at 40° C. After 8 hours, the mixture was concentrated in vacuo. Reverse phase HPLC afforded intermediate (8b) as a TFA salt (1.1 g). MS m/z: [M+H⁺] calcd 389.51. found 390.4.

Thioacetic acid S—((S)-2-{2-[pentanoyl-(2'-sulfamoylbiphenyl-4-ylmethyl)amino]ethylcarbamoyl}-3-phenylpropyl) ester (8c): A solution of (S)-3-acetylsulfanyl-2-benzylpropionic acid (248 mg, 1 mmol; prepared as described in Preparation 7) and HATU (396 mg, 1 mmol) in DMF (2.5 mL) was prepared. After 30 minutes, intermediate (8b) (500 mg) followed by DIPEA (0.5 mL, 3 mmol) was added. After 2 hours, the mixture was concentrated in vacuo. Silica gel chromatography [hexane:EtOAc (5% AcOH)] afforded intermediate (8c) (636 mg). MS m/z: [M+H⁺] calcd 609.80. found 610.4.

Title compound: Acetyl chloride (222 μL, 3.1 mmol), followed by DIPEA (727 μL, 4.3 mmol) was added to a solution of intermediate (8c) (636 mg, 1 mmol) in DCM (3 mL) After stirring overnight, the mixture was extracted with 0.5M aqueous HCl (15 mL) and DCM (2×20 mL). The combined organic fractions were dried over Na₂SO₄, filtered, and concentrated in vacuo to afford a crude intermediate. A solution of the crude intermediate in MeOH (2 mL) and 1M aqueous NaOH (1 mL) was stirred under nitrogen for 1 hour. The mixture was neutralized with 6M aqueous HCl and concentrated in vacuo. Reverse phase HPLC afforded the title compound (63.7 mg). MS m/z: [M+H⁺] calcd for C₃₂H₃₉N₃O₅S₂ 610.23. found 610.5.

Example 9

Following the procedures described in Examples above, and substituting the appropriate starting materials and reagents, compounds 9-1 to 9-15, having the following formula, were also prepared:

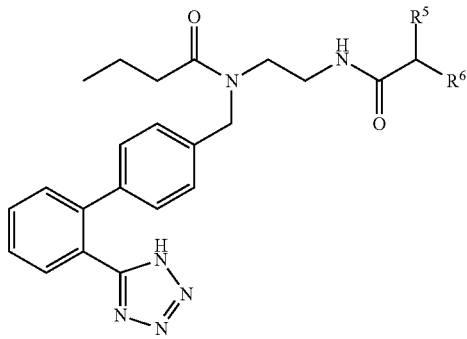

| Ex. | R⁵ | R⁶ |
|---|---|---|
| 9-1 | —CH₂—SH | —(CH₂)₂CH(CH₃)₂ |
| 9-2 | —CH₂—SH | —(CH₂)₃CH₃ |
| 9-3 | —CH₂—SH | —CH(CH₃)CH₂CH₃ |
| 9-4 | —CH₂—SH | —CH₂-cyclopentyl |
| 9-5 | —CH₂—SH | —CH₂-cyclohexyl |
| 9-6 | —CH₂—SH | —CH₂-naphthalen-1-yl |
| 9-7 | —SH | —CH₂CH(CH₃)₂ |
| 9-8 | —SH | —CH₂CH(CH₃)₂ |
| 9-9 | —SH | —(CH₂)₂CH₃ |
| 9-10 | —SH | —(CH₂)₂CH₃ |
| 9-11 | —CH₂—SH | —CH₂-cyclopropyl |
| 9-12 | —CH₂—SH | -cyclohexyl |
| 9-13 | —SH | —CH₂C(CH₃)₃ |
| 9-14 | —SH | —CH₂C(CH₃)₃ |
| 9-15 | —CH₂—SH | -benzyl |

(9-1) 2-mercaptomethyl-5-methylhexanoic acid (2-{butyryl-[2'-(1H-tetrazol-5-yl)biphenyl-4-ylmethyl]amino}ethyl)amide. MS m/z: [M+H⁺] calcd for C₂₈H₃₈N₆O₂S, 523.28. found 523.2.

(9-2) 2-mercaptomethylhexanoic acid (2-{butyryl-[2'-(1H-tetrazol-5-yl)-biphenyl-4-ylmethyl]amino}ethyl) amide. MS m/z: [M+H⁺] calcd for C₂₇H₃₆N₆O₂S, 509.26. found 509.2.

(9-3) 2-mercaptomethyl-3-methylpentanoic acid (2-{butyryl-[2'-(1H-tetrazol-5-yl) biphenyl-4-ylmethyl] amino}ethyl)amide. MS m/z: [M+H⁺] calcd for C₂₇H₃₆N₆O₂S, 509.26. found 509.2.

(9-4) N-[2-(3-cyclopentyl-2-mercaptomethylpropionylamino)ethyl]-N-[2'-(1H-tetrazol-5-yl)-biphenyl-4-ylmethyl]butyramide. MS m/z: [M+H⁺] calcd for C₂₉H₃₈N₆O₂S, 535.28. found 535.2.

(9-5) N-[2-(3-cyclohexyl-2-mercaptomethylpropionylamino)ethyl]-N-[2'-(1H-tetrazol-5-yl)-biphenyl-4-ylmethyl]butyramide. MS m/z: [M+H⁺] calcd for C₃₀H₄₀N₆O₂S, 549.29. found 549.2.

(9-6) N-[2-(2-mercaptomethyl-3-naphthalen-1-ylpropionylamino)ethyl]-N-[2'-(1H-tetrazol-5-yl)-biphenyl-4-ylmethyl]butyramide. MS m/z: [M+H⁺] calcd for C₃₄H₃₆N₆O₂S, 593.26. found 593.2.

(9-7) (R)-2-mercapto-4-methylpentanoic acid (2-{butyryl-[2'-(1H-tetrazol-5-yl) biphenyl-4-ylmethyl] amino}ethyl)amide. MS m/z: [M+H⁺] calcd for C₂₆H₃₄N₆O₂S, 495.25. found 495.2.

(9-8) (S)-2-mercapto-4-methylpentanoic acid (2-{butyryl-[2'-(1H-tetrazol-5-yl) biphenyl-4-ylmethyl]amino}ethyl) amide. MS m/z: [M+H⁺] calcd for C₂₆H₃₄N₆O₂S, 495.25. found 495.2.

(9-9) (R)-2-mercaptopentanoic acid (2-{butyryl-[2'-(1H-tetrazol-5-yl)biphenyl-4-ylmethyl]-amino}ethyl)amide. MS m/z: [M+H⁺] calcd for C₂₅H₃₂N₆O₂S, 481.23. found 480.6.

(9-10) (S)-2-mercaptopentanoic acid (2-{butyryl-[2'-(1H-tetrazol-5-yl)biphenyl-4-ylmethyl]-amino}ethyl)amide. MS m/z: [M+H⁺] calcd for $C_{25}H_{32}N_6O_2S$, 481.23. found 481.2.

(9-11) N-[2-(2-cyclopropylmethyl-3-mercaptopropionylamino)ethyl]-N-[2'-(1H-tetrazol-5-yl)biphenyl-4-ylmethyl]butyramide. MS m/z: [M+H⁺] calcd for $C_{27}H_{34}N_6O_2S$, 507.25. found 507.2.

(9-12) N-[2-(2-cyclohexyl-3-mercaptopropionylamino)ethyl]-N-[2'-(1H-tetrazol-5-yl) biphenyl-4-ylmethyl]butyramide. MS m/z: [M+H⁺] calcd for $C_{29}H_{38}N_6O_2S$, 535.28.

(9-13) (S)-2-mercapto-4,4-dimethylpentanoic acid (2-{butyryl[2'-(1H-tetrazol-5-yl) biphenyl-4-ylmethyl]amino}ethyl)amide. MS m/z: [M+H⁺] calcd for $C_{27}H_{36}N_6O_2S$, 509.26. found 509.2.

(9-14) (R)-2-mercapto-4,4-dimethylpentanoic acid (2-{butyryl[2'-(1H-tetrazol-5-yl) biphenyl-4-ylmethyl]amino}ethyl)amide. MS m/z: [M+H⁺] calcd for $C_{27}H_{36}N_6O_2S$, 509.26. found 509.2.

(9-15) N-[2-((S)-2-benzyl-3-mercaptopropionylamino)ethyl]-N-[2'-(1H-tetrazol-5-yl) biphenyl-4-ylmethyl]butyramide. MS m/z: [M+H⁺] calcd for $C_{30}H_{34}N_6O_2S$, 543.25. found 543.4.

Example 10

Following the procedures described in Examples above, and substituting the appropriate starting materials and reagents, compounds 10-1 and 10-2, having the following formula, were also prepared:

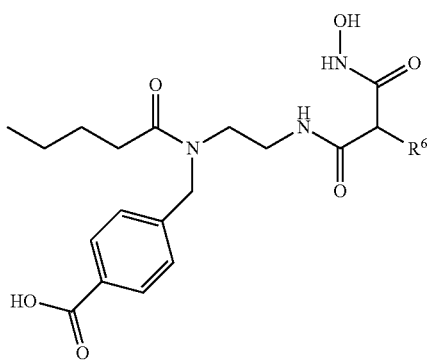

(10-1) 4-({[2-(2-hydroxycarbamoyl-4-methylpentanoylamino)ethyl]pentanoylamino}methyl)benzoic acid ($R^6$=i-butyl). MS m/z: [M+H⁺] calcd for $C_{22}H_{33}N_3O_6$, 436.24. found 436.2.

(10-2) 4-({[2-(2-hydroxycarbamoyl-3-phenylpropionylamino)ethyl]pentanoylamino}methyl)benzoic acid ($R^6$=benzyl). MS m/z: [M+H⁺] calcd for $C_{25}H_{31}N_3O_6$, 470.22. found 470.2.

Example 11

Following the procedures described in Examples above, and substituting the appropriate starting materials and reagents, compounds 11-1 to 11-10, having the following formula, were also prepared:

| Ex. | $R^5$ | $R^6$ |
|---|---|---|
| 11-1 | —CH₂—SH | —CH₂CH(CH₃)₂ |
| 11-2 | —CH₂—SH | benzyl |
| 11-3 | —CH₂—SH | —CH(CH₃)₂ |
| 11-4 | —SH | —CH(CH₃)CH₂CH₃ |
| 11-5 | —CH₂—SH | —CH₃ |
| 11-6 | —NHC(O)CH₂SH | —CH₂CH(CH₃)₂ |
| 11-7 | —C(O)NH(OH) | benzyl |
| 11-8 | —CH₂—SH | —CH₂CH(CH₃)₂ |
| 11-9 | —CH₂—SH | —CH₂CH(CH₃)₂ |
| 11-10 | —CH₂—SH | benzyl |

(11-1) 2-mercaptomethyl-4-methylpentanoic acid (2-{pentanoyl[2'-(1H-tetrazol-5-yl) biphenyl-4-ylmethyl]amino}ethyl)amide. MS m/z: [M+H⁺] calcd for $C_{28}H_{38}N_6O_2S$, 523.28. found 523.4.

(11-2) pentanoic acid [2-(2-benzyl-3-mercaptopropionylamino)ethyl][2'-(1H-tetrazol-5-yl)biphenyl-4-ylmethyl]amide. MS m/z: [M+H⁺] calcd for $C_3H_{36}N_6O_2S$, 557.26. found 557.4.

(11-3) pentanoic acid [2-(2-mercaptomethyl-3-methylbutyrylamino)ethyl][2'-(1H-tetrazol-5-yl)biphenyl-4-ylmethyl]amide. MS m/z: [M+H⁺] calcd for $C_{27}H_{36}N_6O_2S$, 509.26. found 509.4.

(11-4) 2-mercapto-3-methylpentanoic acid (2-{pentanoyl[2'-(1H-tetrazol-5-yl) biphenyl-4-ylmethyl]amino}ethyl)amide. MS m/z: [M+H⁺] calcd for $C_{27}H_{36}N_6O_2S$, 509.26. found 509.4.

(11-5) pentanoic acid [2-((S)-3-mercapto-2-methylpropionylamino)ethyl][2'-(1H-tetrazol-5-yl)biphenyl-4-ylmethyl]amide. MS m/z: [M+H⁺] calcd for $C_{25}H_{32}N_6O_2S$, 481.23. found 481.2.

(11-6) (S)-2-(2-mercaptoacetylamino)-4-methylpentanoic acid (2-{pentanoyl[2'-(1H-tetrazol-5-yl)biphenyl-4-ylmethyl]amino}ethyl)amide. MS m/z: [M+H⁺] calcd for $C_{29}H_{39}N_7O_3S$, 566.28. found 566.4.

(11-7) 2-benzyl-N-hydroxy-N'-(2-{pentanoyl[2'-(1H-tetrazol-5-yl)biphenyl-4-ylmethyl]amino}ethyl)malonamide. MS m/z: [M+H⁺] calcd for $C_{31}H_{35}N_7O_4$, 570.28. found 570.4.

(11-8) (S)-2-mercaptomethyl-4-methylpentanoic acid (2-{pentanoyl[2'-(1H-tetrazol-5-yl)biphenyl-4-ylmethyl]amino}ethyl)amide. MS m/z: [M+H⁺] calcd for $C_{28}H_{38}N_6O_2S$, 523.28. found 523.2.

(11-9) (R)-2-mercaptomethyl-4-methylpentanoic acid (2-{pentanoyl[2'-(1H-tetrazol-5-yl)biphenyl-4-ylmethyl]amino}ethyl)amide. MS m/z: [M+H⁺] calcd for $C_{28}H_{38}N_6O_2S$, 523.28. found 523.3.

(11-10) pentanoic acid [2-((R)-2-benzyl-3-mercaptopropionylamino)ethyl][2'-(1H-tetrazol-5-yl)biphenyl-4-ylmethyl]amide. MS m/z: [M+H$^+$] calcd for $C_{31}H_{36}N_6O_2S$, 557.26. found 557.2.

Example 12

Following the procedures described in Examples above, and substituting the appropriate starting materials and reagents, compounds 12-1 and 12-2, having the following formula, were also prepared:

yl)biphenyl-4-ylmethyl]amide ($R^6$=—CH$_2$CH(CH$_3$)$_2$). MS m/z: [M+H$^+$] calcd for $C_{30}H_{42}N_6O_2S$, 551.31. found 551.4.

Example 13

Following the procedures described in Examples above, and substituting the appropriate starting materials and reagents, compounds 13-1 to 13-17, having the following formula, were also prepared:

| Ex. | $R^1$ | $R^3$ | $R^5$ | $R^6$ |
|---|---|---|---|---|
| 13-1 | tetrazol-5-yl | —(CH$_2$)$_2$CH$_3$ | —CH$_2$—SH | benzyl |
| 13-2 | tetrazol-5-yl | —(CH$_2$)$_2$CH$_3$ | —C(O)NH(OH) | —CH$_2$CH(CH$_3$)$_2$ |
| 13-3 | tetrazol-5-yl | —(CH$_2$)$_2$CH$_3$ | —C(O)NH(OH) | benzyl |
| 13-4 | tetrazol-5-yl | —(CH$_2$)$_2$CH$_3$ | —CH$_2$—SH | —CH(CH$_3$)$_2$ |
| 13-5 | tetrazol-5-yl | —CH$_3$ | —C(O)NH(OH) | benzyl |
| 13-6 | tetrazol-5-yl | —CH$_2$CH$_3$ | —CH$_2$—SH | —CH$_2$CH(CH$_3$)$_2$ |
| 13-7 | tetrazol-5-yl | —CH$_2$CH$_3$ | —CH$_2$—SH | benzyl |
| 13-8 | tetrazol-5-yl | —CH$_2$CH$_3$ | —CH$_2$—SH | —CH$_3$ |
| 13-9 | tetrazol-5-yl | —CH$_2$CH$_3$ | —CH$_2$—SH | —CH$_2$-cyclopropyl |
| 13-10 | tetrazol-5-yl | —CH$_2$CH$_3$ | —SH | benzyl |
| 13-11 | tetrazol-5-yl | —CH$_2$CH$_3$ | —C(O)NH(OH) | —CH$_2$CH(CH$_3$)$_2$ |
| 13-12 | tetrazol-5-yl | —CH$_2$CH$_3$ | —C(O)NH(OH) | benzyl |
| 13-13 | tetrazol-5-yl | —CH$_2$CH$_3$ | —CH$_2$—SH | —CH$_3$ |
| 13-14 | tetrazol-5-yl | —(CH$_2$)$_2$CH$_3$ | —CH$_2$—SH | —CH$_2$CH(CH$_3$)$_2$ |
| 13-15 | tetrazol-5-yl | —(CH$_2$)$_2$CH$_3$ | —CH$_2$—SH | —CH$_2$CH(CH$_3$)$_2$ |
| 13-16 | tetrazol-5-yl | —CH(CH$_2$CH$_3$)$_2$ | —CH$_2$—SH | —CH$_2$CH(CH$_3$)$_2$ |
| 13-17 | —SO$_2$NHC(O)CH$_3$ | —(CH$_2$)$_2$CH$_3$ | —CH$_2$—SH | —CH$_2$CH(CH$_3$)$_2$ |

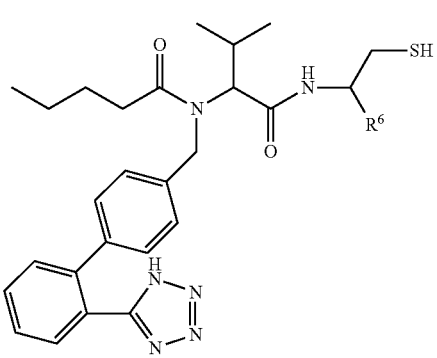

(12-1) pentanoic acid [(S)-1-((R)-1-benzyl-2-mercaptoethylcarbamoyl)-2-methylpropyl][2'-(1H-tetrazol-5-yl)biphenyl-4-ylmethyl]amide ($R^6$=benzyl). MS m/z: [M+H$^+$] calcd for $C_{33}H_{40}N_6O_2S$, 585.29. found 585.5.

(12-2) pentanoic acid [(S)-1-((R)-1-mercaptomethyl-3-methylbutylcarbamoyl)-2-methylpropyl][2'-(1H-tetrazol-5-

(13-1) N-[2-(2-mercaptomethyl-3-phenylpropionylamino)ethyl]-N-[2'-(1H-tetrazol-5-yl)biphenyl-4-ylmethyl]butyramide. MS m/z: [M+H$^+$] calcd for $C_{30}H_{34}N_6O_2S$, 543.25; found 543.2.

(13-2) N-(2-{butyryl[2'-(1H-tetrazol-5-yl)biphenyl-4-ylmethyl]amino}ethyl)-N'-hydroxy-2-isobutylmalonamide. MS m/z: [M+H$^+$] calcd for $C_{27}H_{35}N_7O_4$, 522.28. found 522.2.

(13-3) 2-benzyl-N-(2-{butyryl[2'-(1H-tetrazol-5-yl)biphenyl-4-ylmethyl]amino}ethyl)-N'-hydroxymalonamide. MS m/z: [M+H$^+$] calcd for $C_{30}H_{33}N_7O_4$, 556.26. found 556.2.

(13-4) N-(2-{butyryl[2'-(1H-tetrazol-5-yl)biphenyl-4-ylmethyl]amino}ethyl)-2-mercaptomethyl-3-methylbutyramide. MS m/z: [M+H$^+$] calcd for $C_{26}H_{34}N_6O_2S$, 495.25. found 495.2.

(13-5) N-(2-{acetyl[2'-(1H-tetrazol-5-yl)biphenyl-4-ylmethyl]amino}ethyl)-2-benzyl-N'-hydroxymalonamide. MS m/z: [M+H$^+$] calcd for $C_{28}H_{29}N_7O_4$, 528.23. found 528.2.

(13-6) 2-mercaptomethyl-4-methylpentanoic acid (2-{propionyl[2'-(1H-tetrazol-5-yl)biphenyl-4-ylmethyl]amino}ethyl)amide. MS m/z: [M+H$^+$] calcd for $C_{26}H_{34}N_6O_2S$, 495.25. found 495.0.

(13-7) 2-mercaptomethyl-3-phenyl-N-(2-{propionyl-[2'-(1H-tetrazol-5-yl)biphenyl-4-ylmethyl]amino}ethyl)propionamide. MS m/z: [M+H$^+$] calcd for C$_{29}$H$_{32}$N$_6$O$_2$S, 529.23. found 529.0.

(13-8) 3-mercapto-2-methyl-N-(2-{propionyl[2'-(1H-tetrazol-5-yl)biphenyl-4-ylmethyl]amino}ethyl)propionamide. MS m/z: [M+H$^+$] calcd for C$_{23}$H$_{28}$N$_6$O$_2$S, 453.20. found 453.0.

(13-9) 3-cyclopropyl-2-mercaptomethyl-N-(2-{propionyl[2'-(1H-tetrazol-5-yl) biphenyl-4-ylmethyl]amino}ethyl) propionamide. MS m/z: [M+H$^+$] calcd for C$_{26}$H$_{32}$N$_6$O$_2$S, 493.23. found 493.0.

(13-10) (S)-2-mercapto-3-phenyl-N-(2-{propionyl[2'-(1H-tetrazol-5-yl)biphenyl-4-ylmethyl]amino}ethyl)propionamide. MS m/z: [M+H$^+$] calcd for C$_{28}$H$_{30}$N$_6$O$_2$S, 515.22; found 515.0.

(13-11) N-hydroxy-2-isobutyl-N'-(2-{propionyl[2'-(1H-tetrazol-5-yl)biphenyl-4-ylmethyl]amino}ethyl)malonamide. MS m/z: [M+H$^+$] calcd for C$_{26}$H$_{33}$N$_7$O$_4$, 508.26. found 508.0.

(13-12) 2-benzyl-N-hydroxy-N'-(2-{propionyl[2'-(1H-tetrazol-5-yl)biphenyl-4-ylmethyl]amino}ethyl)malonamide. MS m/z: [M+H$^+$] calcd for C$_{29}$H$_{31}$N$_7$O$_4$, 542.24. found 542.0.

(13-13) (S)-3-mercapto-2-methyl-N-(2-{propionyl[2'-(1H-tetrazol-5-yl)biphenyl-4-ylmethyl]amino}ethyl)propionamide. MS m/z: [M+H$^+$] calcd for C$_{23}$H$_{28}$N$_6$O$_2$S, 453.20. found 453.0.

(13-14) (S)-2-mercaptomethyl-4-methylpentanoic acid (2-{butyryl[2'-(1H-tetrazol-5-yl) biphenyl-4-ylmethyl]amino}ethyl)amide. MS m/z: [M+H$^+$] calcd for C$_{27}$H$_{36}$N$_6$O$_2$S, 509.26. found 509.2.

(13-15) (R)-2-mercaptomethyl-4-methylpentanoic acid (2-{butyryl[2'-(1H-tetrazol-5-yl) biphenyl-4-ylmethyl] amino}ethyl)amide. MS m/z: [M+H$^+$] calcd for C$_{27}$H$_{36}$N$_6$O$_2$S, 509.26. found 509.2.

(13-16) 2-mercaptomethyl-4-methylpentanoic acid (2-{(2-ethylbutyryl)[2'-(1H-tetrazol-5-yl)biphenyl-4-ylmethyl] amino}ethyl)amide. MS m/z: [M+H$^+$] calcd for C$_{29}$H$_{40}$N$_6$O$_2$S, 537.29. found 537.4.

(13-17) (S)-2-mercaptomethyl-4-methylpentanoic acid {2-[(2'-acetylsulfamoylbiphenyl-4-ylmethyl)butyrylamino] ethyl}amide. MS m/z: [M+H$^+$] calcd for C$_{28}$H$_{39}$N$_3$O$_5$S$_2$, 562.23. found 562.5.

Example 14

Following the procedures described in Examples above, and substituting the appropriate starting materials and reagents, compounds 14-1 to 14-7, having the following formula, were also prepared:

| Ex. | X | R$^5$ | R$^6$ |
|---|---|---|---|
| 14-1 | (valine-glycine dipeptide linker structure) | —CH$_2$—SH | benzyl |
| 14-2 | —CH$_2$—C(O)NH— | —CH$_2$NHC(O)—CH$_2$SH | —CH(CH$_3$)$_2$ |
| 14-3 | —CH$_2$—C(O)NH— | —CH$_2$—SH | benzyl |
| 14-4 | —CH$_2$—C(O)NH— | —C(O)NH(OH) | —CH$_2$CH(CH$_3$)$_2$ |
| 14-5 | —CH$_2$—C(O)NH— | —C(O)NH(OH) | —CH$_2$CH(CH$_3$)$_2$ |
| 14-6 | —CH$_2$—C(O)NH— | —CH$_2$C(O)NH(OH) | benzyl |
| 14-7 | —CH$_2$—C(O)NH— | —CH$_2$C(O)NH(OH) | benzyl |

(14-1) 4'-{[((S)-1-{2-[2-(2-benzyl-3-mercaptopropionylamino)acetylamino]ethylcarbamoyl}-2-methylpropyl)pentanoylamino]methyl}biphenyl-2-carboxylic acid. MS m/z: [M+H$^+$] calcd for C$_{38}$H$_{48}$N$_4$O$_6$S, 689.33.

(14-2) 4'-{[({(R)-1-[(2-mercaptoacetylamino)methyl]-2-methylpropylcarbamoyl}methyl)pentanoylamino] methyl}biphenyl-2-carboxylic acid. MS m/z: [M+H$^+$] calcd for C$_{28}$H$_{37}$N$_3$O$_5$S, 528.25. found 528.4.

(14-3) 4'-({[(((R)-1-benzyl-2-mercaptoethylcarbamoyl)methyl]pentanoylamino}methyl)biphenyl-2-carboxylic acid. MS m/z: [M+H$^+$] calcd for C$_{30}$H$_{34}$N$_2$O$_4$S, 519.22. found 519.4.

(14-4) 4'-({[(((S)-1-hydroxycarbamoyl-3-methylbutylcarbamoyl)methyl]pentanoylamino}methyl)biphenyl-2-carboxylic acid. MS m/z: [M+H$^+$] calcd for C$_{27}$H$_{35}$N$_3$O$_6$, 498.25. found 498.4.

(14-5) 4'-({[(((S)-1-hydroxycarbamoyl-2-phenylethylcarbamoyl)methyl]pentanoylamino}methyl)biphenyl-2-carboxylic acid. MS m/z: [M+H$^+$] calcd for C$_{30}$H$_{33}$N$_3$O$_6$, 532.24. found 532.4.

(14-6) 4'-({[(1-hydroxycarbamoylmethyl-3-methylbutyl-carbamoyl)methyl]pentanoylamino}methyl)biphenyl-2-carboxylic acid. MS m/z: [M+H$^+$] calcd for $C_{28}H_{37}N_3O_6$, 512.27. found 512.4.

(14-7) 4'-({[(1-benzyl-2-hydroxycarbamoylethylcarbamoyl)methyl]pentanoylamino}methyl)biphenyl-2-carboxylic acid. MS m/z: [M+H$^+$] calcd for $C_{31}H_{35}N_3O_6$, 546.25. found 546.4.

Example 15

Following the procedures described in Examples above, and substituting the appropriate starting materials and reagents, compounds 15-1 to 15-8, having the following formula, were also prepared:

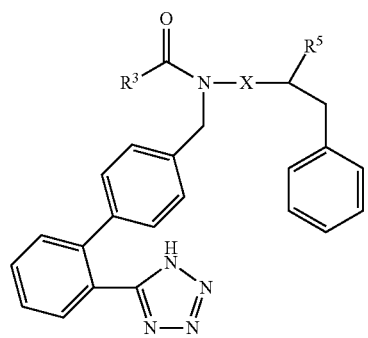

| Ex. | R$^3$ | X | R$^5$ |
|---|---|---|---|
| 15-1 | —(CH$_2$)$_3$CH$_3$ | | —C(O)NH(OH) |
| 15-2 | —(CH$_2$)$_3$CH$_3$ | | —C(O)NH(OH) |
| 15-3 | —(CH$_2$)$_3$CH$_3$ | | —CH$_2$—SH |
| 15-4 | —(CH$_2$)$_3$CH$_3$ | | —C(O)NH(OH) |
| 15-5 | —(CH$_2$)$_3$CH$_3$ | | —C(O)NH(OH) |
| 15-6 | —(CH$_2$)$_3$CH$_3$ | | —C(O)NH(OH) |

-continued

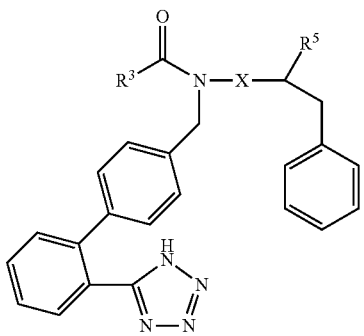

| Ex. | R³ | X | R⁵ |
|---|---|---|---|
| 15-7 | —(CH₂)₃CH₃ | (structure: valine-like amide linker) | —CH₂C(O)NH(OH) |
| 15-8 | —(CH₂)₂CH₃ | (structure: gem-dimethyl amide linker) | —CH₂—SH |

(15-1) 2-benzyl-N-hydroxy-N'-{[6-((S)-3-methyl-2-{pentanoyl[2'-(1H-tetrazol-5-yl)biphenyl-4-ylmethyl]amino}butyrylamino)hexylcarbamoyl]methyl}malonamide. MS m/z: [M+H⁺] calcd for $C_{42}H_{55}N_9O_6$, 782.43. found 782.3.

(15-2) 3-(2-hydroxycarbamoyl-3-phenylpropionylamino)-2-{pentanoyl[2'-(1H-tetrazol-5-yl)biphenyl-4-ylmethyl]amino}propionic acid. MS m/z: [M+H⁺] calcd for $C_{32}H_{35}N_7O_6$, 614.27. found 614.4.

(15-3) 3-[2-(2-benzyl-3-mercaptopropionylamino)acetylamino]-2-{pentanoyl[2'-(1H-tetrazol-5-yl)biphenyl-4-ylmethyl]amino}propionic acid. MS m/z: [M+H⁺] calcd for $C_{34}H_{39}N_7O_5S$, 658.27. found 658.3.

(15-4) 2-[2-(2-hydroxycarbamoyl-3-phenylpropionylamino)acetylamino]-3-{pentanoyl[2'-(1H-tetrazol-5-yl)biphenyl-4-ylmethyl]amino}propionic acid. MS m/z: [M+H⁺] calcd for $C_{34}H_{38}N_8O_7$, 671.29. found 671.2.

(15-5) 3-[2-(2-hydroxycarbamoyl-3-phenylpropionylamino)acetylamino]-2-{pentanoyl[2'-(1H-tetrazol-5-yl)biphenyl-4-ylmethyl]amino}propionic acid. MS m/z: [M+H⁺] calcd for $C_{34}H_{38}N_8O_7$, 671.29. found 671.2.

(15-6) 2-(2-hydroxycarbamoyl-3-phenylpropionylamino)-3-{pentanoyl[2'-(1H-tetrazol-5-yl)biphenyl-4-ylmethyl]amino}propionic acid. MS m/z: [M+H⁺] calcd for $C_{32}H_{35}N_7O_6$, 614.27. found 614.2.

(15-7) pentanoic acid [(S)-1-(1-benzyl-2-hydroxycarbamoylethylcarbamoyl)-2-methylpropyl][2'-(1H-tetrazol-5-yl)biphenyl-4-ylmethyl]amide. MS m/z: [M+H⁺] calcd for $C_{34}H_{41}N_7O_4$, 612.32. found 612.2.

(15-8) N-[2-((S)-2-benzyl-3-mercaptopropionylamino)-2-methylpropyl]-N-[2'-(1H-tetrazol-5-yl)biphenyl-4-ylmethyl]butyramide. MS m/z: [M+H⁺] calcd for $C_{32}H_{38}N_6O_2S$, 571.28. found 571.2.

Example 16

Following the procedures described in Examples above, and substituting the appropriate starting materials and reagents, compounds 16-1 to 16-32, having the following formula, were also prepared:

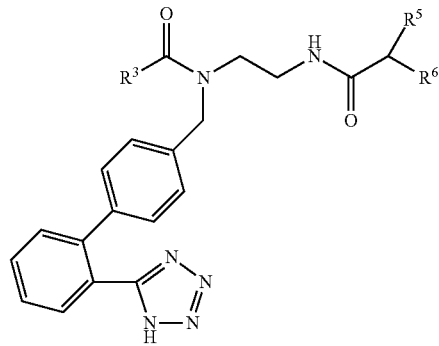

| Ex. | R³ | R⁵ | R⁶ |
|---|---|---|---|
| 16-1 | -cyclopropyl | —CH₂—SH | benzyl |
| 16-2 | -cyclopropyl | —CH₂—SH | —CH₂CH(CH₃)₂ |
| 16-3 | -cyclopropyl | —CH₂—SH | —CH₃ |
| 16-4 | -cyclopropyl | —CH₂—SH | —CH(CH₃)₂ |
| 16-5 | -cyclopropyl | —SH | benzyl |
| 16-6 | -cyclopropyl | —C(O)NH(OH) | —CH₂CH(CH₃)₂ |
| 16-7 | -cyclopropyl | —C(O)NH(OH) | benzyl |
| 16-8 | -cyclopropyl | —CH₂—SH | —CH₃ |
| 16-9 | —CH₂-cyclopentyl | —CH₂—SH | —CH₂CH(CH₃)₂ |
| 16-10 | —(CH₂)₂-cyclopentyl | —CH₂—SH | —CH₂CH(CH₃)₂ |
| 16-11 | phenyl | —CH₂—SH | —CH₂CH(CH₃)₂ |
| 16-12 | benzyl | —CH₂—SH | —CH₂CH(CH₃)₂ |
| 16-13 | —(CH₂)₂-phenyl | —CH₂—SH | —CH₂CH(CH₃)₂ |
| 16-14 | —NH(CH₂)₂CH₃ | —CH₂—SH | —CH₂CH(CH₃)₂ |
| 16-15 | —NHCH₂CH₃ | —CH₂—SH | —CH₂CH(CH₃)₂ |

-continued

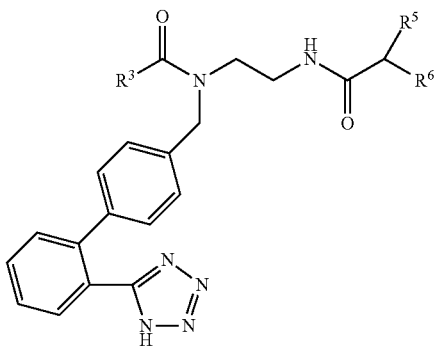

| Ex. | R³ | R⁵ | R⁶ |
|---|---|---|---|
| 16-16 | —NH(CH$_2$)$_3$CH$_3$ | —CH$_2$—SH | —CH$_2$CH(CH$_3$)$_2$ |
| 16-17 | —NH(CH$_2$)$_4$CH$_3$ | —CH$_2$—SH | —CH$_2$CH(CH$_3$)$_2$ |
| 16-18 | —NH(CH$_2$)$_5$CH$_3$ | —CH$_2$—SH | —CH$_2$CH(CH$_3$)$_2$ |
| 16-19 | —NHCH(CH$_3$)$_2$ | —CH$_2$—SH | —CH$_2$CH(CH$_3$)$_2$ |
| 16-20 | —NHCH(CH$_3$)CH$_2$CH$_3$ | —CH$_2$—SH | —CH$_2$CH(CH$_3$)$_2$ |
| 16-21 | cyclopentyl | —CH$_2$—SH | —CH$_2$CH(CH$_3$)$_2$ |
| 16-22 | —CH$_2$-cyclohexyl | —CH$_2$—SH | —CH$_2$CH(CH$_3$)$_2$ |
| 16-23 | phenyl | —CH$_2$—SH | —CH$_2$CH(CH$_3$)$_2$ |
| 16-24 | benzyl | —CH$_2$—SH | —CH$_2$CH(CH$_3$)$_2$ |
| 16-25 | —O(CH$_2$)$_2$CH$_3$ | —CH$_2$—SH | —CH$_2$CH(CH$_3$)$_2$ |
| 16-26 | —OCH$_3$ | —CH$_2$—SH | —CH$_2$CH(CH$_3$)$_2$ |
| 16-27 | —OCH$_2$CH$_3$ | —CH$_2$—SH | —CH$_2$CH(CH$_3$)$_2$ |
| 16-28 | —O(CH$_2$)$_3$CH$_3$ | —CH$_2$—SH | —CH$_2$CH(CH$_3$)$_2$ |
| 16-29 | —OCH(CH$_3$)$_2$ | —CH$_2$—SH | —CH$_2$CH(CH$_3$)$_2$ |
| 16-30 | —OCH$_2$CH(CH$_3$)$_2$ | —CH$_2$—SH | —CH$_2$CH(CH$_3$)$_2$ |
| 16-31 | —O-phenyl | —CH$_2$—SH | —CH$_2$CH(CH$_3$)$_2$ |
| 16-32 | —O-benzyl | —CH$_2$—SH | —CH$_2$CH(CH$_3$)$_2$ |

(16-1) cyclopropanecarboxylic acid [2-(2-benzyl-3-mercaptopropionylamino)ethyl][2'-(1H-tetrazol-5-yl)biphenyl-4-ylmethyl]amide. MS m/z: [M+H$^+$] calcd for C$_{30}$H$_{32}$N$_6$O$_2$S, 541.23. found 541.0.

(16-2) cyclopropanecarboxylic acid [2-(2-mercaptomethyl-4-methylpentanoylamino) ethyl][2'-(1H-tetrazol-5-yl)biphenyl-4-ylmethyl]amide. MS m/z: [M+H$^+$] calcd for C$_{27}$H$_{34}$N$_6$O$_2$S, 507.25. found 507.0.

(16-3) cyclopropanecarboxylic acid [2-(3-mercapto-2-methylpropionylamino)ethyl][2'-(1H-tetrazol-5-yl) biphenyl-4-ylmethyl]amide. MS m/z: [M+H$^+$] calcd for C$_{24}$H$_{28}$N$_6$O$_2$S, 465.20. found 465.0.

(16-4) cyclopropanecarboxylic acid [2-(2-mercaptomethyl-3-methylbutyrylamino) ethyl]-2'-(1H-tetrazol-5-yl)biphenyl-4-ylmethyl]amide. MS m/z: [M+H$^+$] calcd for C$_{26}$H$_{32}$N$_6$O$_2$S, 493.23. found 493.0.

(16-5) cyclopropanecarboxylic acid [2-((S)-2-mercapto-3-phenylpropionylamino)ethyl][2'-(1H-tetrazol-5-yl)biphenyl-4-ylmethyl]amide. MS m/z: [M+H$^+$] calcd for C$_{29}$H$_{30}$N$_6$O$_2$S, 527.22. found 527.0.

(16-6) N-(2-{cyclopropanecarbonyl[2'-(1H-tetrazol-5-yl)biphenyl-4-ylmethyl]amino}ethyl)-N'-hydroxy-2-isobutylmalonamide. MS m/z: [M+H$^+$] calcd for C$_{27}$H$_{33}$N$_7$O$_4$, 520.26. found 520.0.

(16-7) 2-benzyl-N-(2-{cyclopropanecarbonyl[2'-(1H-tetrazol-5-yl)biphenyl-4-ylmethyl]amino}ethyl)-N'-hydroxymalonamide. MS m/z: [M+H$^+$] calcd for C$_{30}$H$_{31}$N$_7$O$_4$, 554.24. found 554.0.

(16-8) cyclopropanecarboxylic acid [2-((S)-3-mercapto-2-methylpropionylamino)ethyl][2'-(1H-tetrazol-5-yl)biphenyl-4-ylmethyl]amide. MS m/z: [M+H$^+$] calcd for C$_{24}$H$_{28}$N$_6$O$_2$S, 465.20. found 465.0.

(16-9) 2-mercaptomethyl-4-methylpentanoic acid (2-{(2-cyclopentylacetyl)[2'-(1H-tetrazol-5-yl)biphenyl-4-ylmethyl]amino}ethyl)amide. MS m/z: [M+H$^+$] calcd for C$_{30}$H$_{40}$N$_6$O$_2$S, 549.29. found 549.4.

(16-10) 2-mercaptomethyl-4-methylpentanoic acid (2-{(3-cyclopentylpropionyl)[2'-(1H-tetrazol-5-yl)biphenyl-4-ylmethyl]amino}ethyl)amide. MS m/z: [M+H$^+$] calcd for C$_{31}$H$_{42}$N$_6$O$_2$S, 563.31. found 563.4.

(16-11) N-[2-(2-mercaptomethyl-4-methylpentanoylamino)ethyl]-N-[2'-(1H-tetrazol-5-yl)biphenyl-4-ylmethyl]benzamide. MS m/z: [M+H$^+$] calcd for C$_{30}$H$_{34}$N$_6$O$_2$S, 543.25. found 543.2.

(16-12) 2-mercaptomethyl-4-methylpentanoic acid (2-{phenylacetyl[2'-(1H-tetrazol-5-yl)biphenyl-4-ylmethyl]amino}ethyl)amide. MS m/z: [M+H$^+$] calcd for C$_{31}$H$_{36}$N$_6$O$_2$S, 557.26. found 557.2.

(16-13) 2-mercaptomethyl-4-methylpentanoic acid (2-{(3-phenylpropionyl) [2'-(1H-tetrazol-5-yl)biphenyl-4-ylmethyl]amino}ethyl)amide. MS m/z: [M+H$^+$] calcd for C$_{32}$H$_{38}$N$_6$O$_2$S, 571.28. found 571.2.

(16-14) 2-mercaptomethyl-4-methylpentanoic acid (2-{3-propyl-1-[2'-(1H-tetrazol-5-yl) biphenyl-4-ylmethyl]ureido}ethyl)amide. MS m/z: [M+H$^+$] calcd for C$_{27}$H$_{37}$N$_7$O$_2$S, 524.27. found 524.2.

(16-15) 2-mercaptomethyl-4-methylpentanoic acid (2-{3-ethyl-1-[2'-(1H-tetrazol-5-yl) biphenyl-4-ylmethyl]ureido}ethyl)amide. MS m/z: [M+H$^+$] calcd for C$_{26}$H$_{35}$N$_7$O$_2$S, 510.26. found 510.2.

(16-16) 2-mercaptomethyl-4-methylpentanoic acid (2-{3-butyl-1-[2'-(1H-tetrazol-5-yl) biphenyl-4-ylmethyl]ureido}ethyl)amide. MS m/z: [M+H$^+$] calcd for C$_{28}$H$_{39}$N$_7$O$_2$S, 538.29. found 538.4.

(16-17) 2-mercaptomethyl-4-methylpentanoic acid (2-{3-pentyl-1-[2'-(1H-tetrazol-5-yl) biphenyl-4-ylmethyl]ureido}ethyl)amide. MS m/z: [M+H$^+$] calcd for C$_{29}$H$_{41}$N$_7$O$_2$S, 552.30. found 552.4.

(16-18) 2-mercaptomethyl-4-methylpentanoic acid (2-{3-hexyl-1-[2'-(1H-tetrazol-5-yl)biphenyl-4-ylmethyl]ureido}ethyl)amide. MS m/z: [M+H$^+$] calcd for C$_{30}$H$_{43}$N$_7$O$_2$S, 566.32. found 566.4.

(16-19) 2-mercaptomethyl-4-methylpentanoic acid (2-{3-isopropyl-1-[2'-(1H-tetrazol-5-yl)biphenyl-4-ylmethyl]ureido}ethyl)amide. MS m/z: [M+H$^+$] calcd for C$_{27}$H$_{37}$N$_7$O$_2$S, 524.27. found 524.2.

(16-20) 2-mercaptomethyl-4-methylpentanoic acid (2-{3-sec-butyl-1-[2'-(1H-tetrazol-5-yl)biphenyl-4-ylmethyl]ureido}ethyl)amide. MS m/z: [M+H$^+$] calcd for C$_{28}$H$_{39}$N$_7$O$_2$S, 538.29. found 538.2.

(16-21) 2-mercaptomethyl-4-methylpentanoic acid (2-{3-cyclopentyl-1-[2'-(1H-tetrazol-5-yl)biphenyl-4-ylmethyl]ureido}ethyl)amide. MS m/z: [M+H$^+$] calcd for C$_{29}$H$_{39}$N$_7$O$_2$S, 550.29. found 550.4.

(16-22) 2-mercaptomethyl-4-methylpentanoic acid (2-{3-cyclohexylmethyl-1-[2'-(1H-tetrazol-5-yl)biphenyl-4-ylmethyl]ureido}ethyl)amide. MS m/z: [M+H$^+$] calcd for C$_{31}$H$_{43}$N$_7$O$_2$S, 578.32. found 578.4.

(16-23) 2-mercaptomethyl-4-methylpentanoic acid (2-{3-phenyl-1-[T-(1H-tetrazol-5-yl)biphenyl-4-ylmethyl]ureido}ethyl)amide. MS m/z: [M+H$^+$] calcd for C$_{30}$H$_{35}$N$_7$O$_2$S, 558.26. found 558.2.

(16-24) 2-mercaptomethyl-4-methylpentanoic acid (2-{3-benzyl-1-[2'-(1H-tetrazol-5-yl) biphenyl-4-ylmethyl]ureido}ethyl)amide. MS m/z: [M+H$^+$] calcd for C$_{31}$H$_{37}$N$_7$O$_2$S, 572.27. found 572.2.

(16-25) [2-(2-mercaptomethyl-4-methylpentanoylamino) ethyl][2'-(1H-tetrazol-5-yl) biphenyl-4-ylmethyl]carbamic acid propyl ester. MS m/z: [M+H$^+$] calcd for C$_{27}$H$_{36}$N$_6$O$_3$S, 525.26. found 525.2.

(16-26) [2-(2-mercaptomethyl-4-methylpentanoylamino) ethyl][2'-(1H-tetrazol-5-yl)biphenyl-4-ylmethyl]carbamic acid methyl ester. MS m/z: [M+H$^+$] calcd for $C_{25}H_{32}N_6O_3S$, 497.23. found 497.2.

(16-27) [2-(2-mercaptomethyl-4-methylpentanoylamino) ethyl][2'-(1H-tetrazol-5-yl) biphenyl-4-ylmethyl]carbamic acid ethyl ester. MS m/z: [M+H$^+$] calcd for $C_{26}H_{34}N_6O_3S$, 511.24. found 511.2.

(16-28) [2-(2-mercaptomethyl-4-methylpentanoylamino) ethyl][2'-(1H-tetrazol-5-yl) biphenyl-4-ylmethyl]carbamic acid butyl ester. MS m/z: [M+H$^+$] calcd for $C_{28}H_{38}N_6O_3S$, 539.27. found 539.2.

(16-29) [2-(2-mercaptomethyl-4-methylpentanoylamino) ethyl][2'-(1H-tetrazol-5-yl) biphenyl-4-ylmethyl]carbamic acid isopropyl ester. MS m/z: [M+H$^+$] calcd for $C_{27}H_{36}N_6O_3S$, 525.26. found 525.2.

(16-30) [2-(2-mercaptomethyl-4-methylpentanoylamino) ethyl][2'-(1H-tetrazol-5-yl) biphenyl-4-ylmethyl]carbamic acid isobutyl ester. MS m/z: [M+H$^+$] calcd for $C_{28}H_{38}N_6O_3S$, 539.27. found 539.2.

(16-31) [2-(2-mercaptomethyl-4-methylpentanoylamino) ethyl][2'-(1H-tetrazol-5-yl) biphenyl-4-ylmethyl]carbamic acid phenyl ester. MS m/z: [M+H$^+$] calcd for $C_{30}H_{34}N_6O_3S$, 559.24. found 559.2.

(16-32) [2-(2-mercaptomethyl-4-methylpentanoylamino) ethyl][2'-(1H-tetrazol-5-yl) biphenyl-4-ylmethyl]carbamic acid benzyl ester. MS m/z: [M+H$^+$] calcd for $C_{31}H_{36}N_6O_3S$, 573.26. found 573.2.

Example 17

Following the procedures described in Examples above, and substituting the appropriate starting materials and reagents, compounds 17-1 to 17-8, having the following formula, were also prepared:

| Ex. | R$^5$ | R$^6$ |
|---|---|---|
| 17-1 | —C(O)NH(OH) | —CH$_2$CH(CH$_3$)$_2$ |
| 17-2 | —C(O)NH(OH) | benzyl |
| 17-3 | —CH$_2$—SH | benzyl |
| 17-4 | —SH | benzyl |
| 17-5 | —CH$_2$—SH | —CH$_2$CH(CH$_3$)$_2$ |
| 17-6 | —CH$_2$—SH | —CH(CH$_3$)$_2$ |
| 17-7 | —CH$_2$—SH | —CH$_3$ |
| 17-8 | —CH$_2$—SH | —CH$_3$ |

(17-1) N-hydroxy-2-isobutyl-N'-(3-{pentanoyl[2'-(1H-tetrazol-5-yl)biphenyl-4-ylmethyl]amino}propyl)malonamide. MS m/z: [M+H$^+$] calcd for $C_{29}H_{39}N_7O_4$, 550.31. found 550.4.

(17-2) 2-benzyl-N-hydroxy-N'-(3-{pentanoyl[2'-(1H-tetrazol-5-yl)biphenyl-4-ylmethyl]amino}propyl)malonamide. MS m/z: [M+H$^+$] calcd for $C_{32}H_{37}N_7O_4$, 584.29. found 584.4.

(17-3) pentanoic acid [3-(2-mercaptomethyl-3-phenylpropionylamino)propyl][2'-(1H-tetrazol-5-yl)biphenyl-4-ylmethyl]amide. MS m/z: [M+H$^+$] calcd for $C_{32}H_{38}N_6O_2S$, 571.28. found 571.4.

(17-4) pentanoic acid [3-((S)-2-mercapto-3-phenylpropionylamino)propyl][2'-(1H-tetrazol-5-yl)biphenyl-4-ylmethyl]amide. MS m/z: [M+H$^+$] calcd for $C_{31}H_{36}N_6O_2S$, 557.26. found 557.2.

(17-5) 2-mercaptomethyl-4-methyl-pentanoic acid (3-{pentanoyl[2'-(1H-tetrazol-5-yl)biphenyl-4-ylmethyl]amino}propyl)amide. MS m/z: [M+H$^+$] calcd for $C_{29}H_{40}N_6O_2S$, 537.29. found 537.4.

(17-6) pentanoic acid [3-(2-mercaptomethyl-3-methylbutyrylamino)propyl][2'-(1H-tetrazol-5-yl)biphenyl-4-ylmethyl]amide. MS m/z: [M+H$^+$] calcd for $C_{28}H_{38}N_6O_2S$, 523.28. found 523.2.

(17-7) pentanoic acid [3-((S)-3-mercapto-2-methylpropionylamino)propyl][2'-(1H-tetrazol-5-yl)biphenyl-4-ylmethyl]amide. MS m/z: [M+H$^+$] calcd for $C_{26}H_{34}N_6O_2S$, 495.25. found 495.2.

(17-8) pentanoic acid [3-(3-mercapto-2-methylpropionylamino)propyl]-[2'-(1H-tetrazol-5-yl)biphenyl-4-ylmethyl]amide. MS m/z: [M+H$^+$] calcd for $C_{26}H_{34}N_6O_2S$, 495.25. found 495.2.

Example 18

Following the procedures described in Examples above, and substituting the appropriate starting materials and reagents, compounds 18-1 and 18-2, having the following formula, were also prepared:

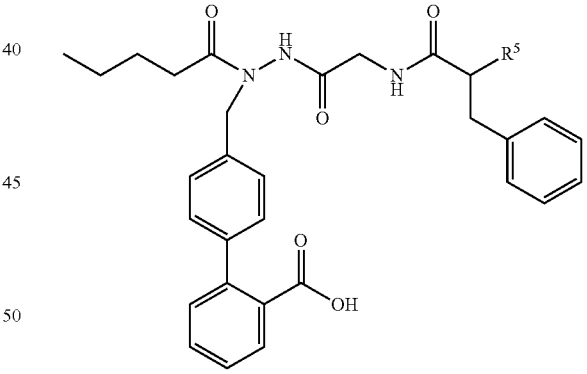

(18-1) 4'-{N'-[2-(2-mercaptomethyl-3-phenylpropionylamino)acetyl]-N-pentanoylhydrazinomethyl}biphenyl-2-carboxylic acid (R$^5$=—CH$_2$—SH). MS m/z: [M+H$^+$] calcd for $C_{31}H_{35}N_3O_5S$, 562.23. found 562.3.

(18-2) 4'-{N'-[2-(2-hydroxycarbamoyl-3-phenylpropionylamino)acetyl]-N-pentanoylhydrazinomethyl}biphenyl-2-carboxylic acid (R$^5$=—C(O)NH(OH)). MS m/z: [M+H$^+$] calcd for $C_{31}H_{34}N_4O_7$, 575.24. found 575.3.

Example 19

Following the procedures described in Examples above, and substituting the appropriate starting materials and reagents, compounds 19-1 to 19-27 and 19-29 to 19-60, having the following formulas (19a), (19b), (19c), (19d), (19e), or (19f), can also be prepared. Compound 19-28 was synthesized in a manner similar to that described in Example 8.

(19a)

(19b)

(19c)

(19d)

(19e)

(19f)

| Ex. | Formula | $R^{1d}$ | $R^6$ |
|---|---|---|---|
| 19-1 | 19a | —C(O)—CH(CH$_3$)OH | -2-fluorobenzyl |
| 19-2 | 19a | —C(O)—CH(CH$_3$)OH | -3-chlorobenzyl |
| 19-3 | 19a | —C(O)—CH(CH$_3$)OH | benzyl |
| 19-4 | 19a | —C(O)—CH(CH$_3$)OH | i-butyl |
| 19-5 | 19a | —C(O)—CH(CH$_3$)OH | cyclohexyl |
| 19-6 | 19a | —C(O)CH$_3$ | -2-fluorobenzyl |
| 19-7 | 19a | —C(O)CH$_3$ | -3-chlorobenzyl |
| 19-8 | 19a | —C(O)CH$_3$ | benzyl |
| 19-9 | 19a | —C(O)CH$_3$ | i-butyl |
| 19-10 | 19a | —C(O)CH$_3$ | cyclohexyl |
| 19-11 | 19b | —C(O)—CH(CH$_3$)OH | -2-fluorobenzyl |
| 19-12 | 19b | —C(O)—CH(CH$_3$)OH | -3-chlorobenzyl |
| 19-13 | 19b | —C(O)—CH(CH$_3$)OH | benzyl |
| 19-14 | 19b | —C(O)—CH(CH$_3$)OH | i-butyl |
| 19-15 | 19b | —C(O)—CH(CH$_3$)OH | cyclohexyl |
| 19-16 | 19b | —C(O)CH$_3$ | -2-fluorobenzyl |
| 19-17 | 19b | —C(O)CH$_3$ | -3-chlorobenzyl |
| 19-18 | 19b | —C(O)CH$_3$ | benzyl |
| 19-19 | 19b | —C(O)CH$_3$ | i-butyl |
| 19-20 | 19b | —C(O)CH$_3$ | cyclohexyl |
| 19-21 | 19c | —C(O)—CH(CH$_3$)OH | -2-fluorobenzyl |
| 19-22 | 19c | —C(O)—CH(CH$_3$)OH | -3-chlorobenzyl |
| 19-23 | 19c | —C(O)—CH(CH$_3$)OH | benzyl |
| 19-24 | 19c | —C(O)—CH(CH$_3$)OH | i-butyl |
| 19-25 | 19c | —C(O)—CH(CH$_3$)OH | cyclohexyl |
| 19-26 | 19c | —C(O)CH$_3$ | -2-fluorobenzyl |
| 19-27 | 19c | —C(O)CH$_3$ | -3-chlorobenzyl |
| 19-28 | 19c | —C(O)CH$_3$ | benzyl |
| 19-29 | 19c | —C(O)CH$_3$ | i-butyl |
| 19-30 | 19c | —C(O)CH$_3$ | cyclohexyl |
| 19-31 | 19d | —C(O)—CH(CH$_3$)OH | -2-fluorobenzyl |
| 19-32 | 19d | —C(O)—CH(CH$_3$)OH | -3-chlorobenzyl |
| 19-33 | 19d | —C(O)—CH(CH$_3$)OH | benzyl |
| 19-34 | 19d | —C(O)—CH(CH$_3$)OH | i-butyl |
| 19-35 | 19d | —C(O)—CH(CH$_3$)OH | cyclohexyl |
| 19-36 | 19d | —C(O)CH$_3$ | -2-fluorobenzyl |
| 19-37 | 19d | —C(O)CH$_3$ | -3-chlorobenzyl |
| 19-38 | 19d | —C(O)CH$_3$ | benzyl |
| 19-39 | 19d | —C(O)CH$_3$ | i-butyl |
| 19-40 | 19d | —C(O)CH$_3$ | cyclohexyl |
| 19-41 | 19e | —C(O)—CH(CH$_3$)OH | -2-fluorobenzyl |
| 19-42 | 19e | —C(O)—CH(CH$_3$)OH | -3-chlorobenzyl |
| 19-43 | 19e | —C(O)—CH(CH$_3$)OH | benzyl |

-continued

| | | | |
|---|---|---|---|
| 19-44 | 19e | —C(O)—CH(CH₃)OH | i-butyl |
| 19-45 | 19e | —C(O)—CH(CH₃)OH | cyclohexyl |
| 19-46 | 19e | —C(O)CH₃ | -2-fluorobenzyl |
| 19-47 | 19e | —C(O)CH₃ | -3-chlorobenzyl |
| 19-48 | 19e | —C(O)CH₃ | benzyl |
| 19-49 | 19e | —C(O)CH₃ | i-butyl |
| 19-50 | 19e | —C(O)CH₃ | cyclohexyl |
| 19-51 | 19f | —C(O)—CH(CH₃)OH | -2-fluorobenzyl |
| 19-52 | 19f | —C(O)—CH(CH₃)OH | -3-chlorobenzyl |
| 19-53 | 19f | —C(O)—CH(CH₃)OH | benzyl |
| 19-54 | 19f | —C(O)—CH(CH₃)OH | i-butyl |
| 19-55 | 19f | —C(O)—CH(CH₃)OH | cyclohexyl |
| 19-56 | 19f | —C(O)CH₃ | -2-fluorobenzyl |
| 19-57 | 19f | —C(O)CH₃ | -3-chlorobenzyl |
| 19-58 | 19f | —C(O)CH₃ | benzyl |
| 19-59 | 19f | —C(O)CH₃ | i-butyl |
| 19-60 | 19f | —C(O)CH₃ | cyclohexyl |

These compounds are named below. Although the nomenclature depicts one stereoisomer embodiment, it is understood that all stereoisomeric forms of these compounds are included in the invention.

(19-1) pentanoic acid {2-[(S)-2-(2-fluorobenzyl)-3-mercaptopropionylamino]ethyl}[2'((S)-2-hydroxypropionylsulfamoyl)biphenyl-4-ylmethyl]amide;

(19-2) pentanoic acid {2-[(S)-2-(3-chlorobenzyl)-3-mercaptopropionylamino]ethyl}[2'-((S)-2-hydroxypropionylsulfamoyl)biphenyl-4-ylmethyl]amide;

(19-3) pentanoic acid [2-((S)-2-benzyl-3-mercaptopropionylamino)ethyl][2'-((S)-2-hydroxypropionylsulfamoyl)biphenyl-4-ylmethyl]amide;

(19-4) (S)-2-mercaptomethyl-4-methylpentanoic acid (2-{[2'-((S)-2-hydroxypropionylsulfamoyl)biphenyl-4-ylmethyl]pentanoylamino}ethyl)amide;

(19-5) pentanoic acid [2-((S)-2-cyclohexyl-3-mercaptopropionylamino)ethyl][2'-((S)-2-hydroxypropionylsulfamoyl)biphenyl-4-ylmethyl]amide;

(19-6) pentanoic acid (2'-acetylsulfamoylbiphenyl-4-ylmethyl){2-[(S)-2-(2-fluorobenzyl)-3-mercaptopropionylamino]ethyl}amide;

(19-7) pentanoic acid (2'-acetylsulfamoylbiphenyl-4-ylmethyl){2-[(S)-2-(3-chlorobenzyl)-3-mercaptopropionylamino]ethyl}amide;

(19-8) pentanoic acid (2'-acetylsulfamoylbiphenyl-4-ylmethyl){2-[(S)-2-benzyl-3-mercaptopropionylamino]ethyl}amide (the synthesis of this compound is described in Example 8);

(19-9) (S)-2-mercaptomethyl-4-methylpentanoic acid {2-[(2'-acetylsulfamoylbiphenyl-4-ylmethyl)pentanoylamino]ethyl}amide;

(19-10) pentanoic acid (2'-acetylsulfamoylbiphenyl-4-ylmethyl){2-[(S)-2-cyclohexyl-3-mercaptopropionylamino]ethyl}amide;

(19-11) pentanoic acid {2-[(R)-2-(2-fluorobenzyl)-2-mercaptoethylcarbamoyl]ethyl}[2'-((S)-2-hydroxypropionylsulfamoyl)biphenyl-4-ylmethyl]amide;

(19-12) pentanoic acid {2-[(R)-2-(3-chlorobenzyl)-2-mercaptoethylcarbamoyl]ethyl}[2'-((S)-2-hydroxypropionylsulfamoyl)biphenyl-4-ylmethyl]amide;

(19-13) pentanoic acid [2-((R)-2-benzyl-2-mercaptoethylcarbamoyl)ethyl][2'-((S)-2-hydroxypropionylsulfamoyl)biphenyl-4-ylmethyl]amide;

(19-14) pentanoic acid [2'-((S)-2-hydroxypropionylsulfamoyl)biphenyl-4-ylmethyl]-[2-((R)-1-mercaptomethyl-3-methylbutylcarbamoyl)ethyl]amide;

(19-15) pentanoic acid [2-((R)-2-cyclohexyl-2-mercaptoethylcarbamoyl)ethyl][2'-((S)-2-hydroxypropionylsulfamoyl)biphenyl-4-ylmethyl]amide;

(19-16) pentanoic acid (2'-acetylsulfamoylbiphenyl-4-ylmethyl){2-[(R)-2-(2-fluorobenzyl)-2-mercaptoethylcarbamoyl]ethyl}amide;

(19-17) pentanoic acid (2'-acetylsulfamoylbiphenyl-4-ylmethyl){2-[(R)-2-(3-chlorobenzyl)-2-mercaptoethylcarbamoyl]ethyl}amide;

(19-18) pentanoic acid (2'-acetylsulfamoylbiphenyl-4-ylmethyl){2-[(R)-2-benzyl-2-mercaptoethylcarbamoyl]ethyl}amide;

(19-19) pentanoic acid (2'-acetylsulfamoylbiphenyl-4-ylmethyl)-[2-((R)-1-mercaptomethyl-3-methyl-butylcarbamoyl)ethyl]amide;

(19-20) pentanoic acid (2'-acetylsulfamoylbiphenyl-4-ylmethyl){2-[(R)-2-cyclohexyl-2-mercaptoethylcarbamoyl]ethyl}amide;

(19-21) pentanoic acid {2-[(S)-2-(2-fluorobenzyl)-3-mercaptopropionylamino]ethyl}[3-fluoro-2'-((S)-2-hydroxypropionylsulfamoyl)biphenyl-4-ylmethyl]amide;

(19-22) pentanoic acid {2-[(S)-2-(3-chlorobenzyl)-3-mercaptopropionylamino]ethyl}[3-fluoro-2'-((S)-2-hydroxypropionylsulfamoyl)biphenyl-4-ylmethyl]amide;

(19-23) pentanoic acid {2-[(S)-2-benzyl-3-mercaptopropionylamino]ethyl}-[3-fluoro-2'-((S)-2-hydroxypropionylsulfamoyl)biphenyl-4-ylmethyl]amide;

(19-24) (S)-2-mercaptomethyl-4-methylpentanoic acid (2-{[3-fluoro-2'-((S)-2-hydroxy-propionylsulfamoyl)biphenyl-4-ylmethyl]pentanoylamino}ethyl)amide (19-25) pentanoic acid {2-[(S)-2-cyclohexyl-3-mercaptopropionylamino]ethyl}[3-fluoro-2'-((S)-2-hydroxypropionylsulfamoyl)biphenyl-4-ylmethyl]amide;

(19-26) pentanoic acid (2'-acetylsulfamoyl-3-fluorobiphenyl-4-ylmethyl)-{2-[(S)-2-(2-fluorobenzyl)-3-mercaptopropionylamino]ethyl}amide;

(19-27) pentanoic acid (2'-acetylsulfamoyl-3-fluorobiphenyl-4-ylmethyl)-{2-[(S)-2-(3-chlorobenzyl)-3-mercaptopropionylamino]ethyl}amide;

(19-28) pentanoic acid (2'-acetylsulfamoyl-3-fluorobiphenyl-4-ylmethyl)-[2-((S)-2-benzyl-3-mercaptopropionylamino)ethyl]amide, MS m/z: [M+H⁺] calcd for $C_{32}H_{38}FN_3O_5S_2$, 628.22. found 628.6 (this compound was synthesized in a manner similar to that described in Example 8);

(19-29) (S)-2-mercaptomethyl-4-methylpentanoic acid {2-[(2'-acetylsulfamoyl-3-fluorobiphenyl-4-ylmethyl)pentanoylamino]ethyl}amide;

(19-30) pentanoic acid (2'-acetylsulfamoyl-3-fluorobiphenyl-4-ylmethyl)[2-((S)-2-cyclohexyl-3-mercaptopropionylamino)ethyl]amide;

(19-31) pentanoic acid {2-[(R)-2-(2-fluorobenzyl)-2-mercaptoethylcarbamoyl]ethyl}[3-fluoro-2'-((S)-2-hydroxypropionylsulfamoyl)biphenyl-4-ylmethyl]amide;

(19-32) pentanoic acid {2-[(R)-2-(3-chlorobenzyl)-2-mercaptoethylcarbamoyl]ethyl}[3-fluoro-2'-((S)-2-hydroxypropionylsulfamoyl)biphenyl-4-ylmethyl]amide;

(19-33) pentanoic acid {2-[(R)-2-benzyl-2-mercaptoethylcarbamoyl]ethyl}[3-fluoro-2'-((S)-2-hydroxypropionylsulfamoyl)biphenyl-4-ylmethyl]amide;

(19-34) pentanoic acid [3-fluoro-2'-((S)-2-hydroxypropionylsulfamoyl)biphenyl-4-ylmethyl][2-((R)-1-mercaptomethyl-3-methylbutylcarbamoyl)ethyl]amide;

(19-35) pentanoic acid {2-[(R)-2-cyclohexyl-2-mercaptoethylcarbamoyl]ethyl}-[3-fluoro-2'-((S)-2-hydroxypropionylsulfamoyl)biphenyl-4-ylmethyl]amide;

(19-36) pentanoic acid (2'-acetylsulfamoyl-3-fluorobiphenyl-4-ylmethyl)-{2-[(R)-2-(2-fluorobenzyl)-2-mercaptoethylcarbamoyl]ethyl}amide;

(19-37) pentanoic acid (2'-acetylsulfamoyl-3-fluorobiphenyl-4-ylmethyl)-{2-[(R)-2-(3-chlorobenzyl)-2-mercaptoethylcarbamoyl]ethyl}amide;

(19-38) pentanoic acid (2'-acetylsulfamoyl-3-fluorobiphenyl-4-ylmethyl)-[2-((R))-2-benzyl-2-mercaptoethylcarbamoyl)ethyl]amide;

(19-39) pentanoic acid (2'-acetylsulfamoyl-3-fluorobiphenyl-4-ylmethyl)-[2-((R)-1-mercaptomethyl-3-methylbutylcarbamoyl)ethyl]amide;

(19-40) pentanoic acid (2'-acetylsulfamoyl-3-fluorobiphenyl-4-ylmethyl)-[2-((R)-2-cyclohexyl-2-mercaptoethylcarbamoyl)ethyl]amide;

(19-41) pentanoic acid [2-chloro-2'-((S)-2-hydroxypropionylsulfamoyl)biphenyl-4-ylmethyl]{2-[(S)-2-(2-fluorobenzyl)-3-mercaptopropionylamino]ethyl}amide;

(19-42) pentanoic acid [2-chloro-2'-((S)-2-hydroxypropionylsulfamoyl)biphenyl-4-ylmethyl]{2-[(S)-2-(3-chlorobenzyl)-3-mercaptopropionylamino]ethyl}amide;

(19-43) pentanoic acid [2-chloro-2'-((S)-2-hydroxypropionylsulfamoyl)biphenyl-4-ylmethyl]{2-[(S)-2-benzyl-3-mercaptopropionylamino]ethyl}amide;

(19-44) (S)-2-mercaptomethyl-4-methylpentanoic acid (2-{[2-chloro-2'-((S)-2-hydroxypropionylsulfamoyl)biphenyl-4-ylmethyl]pentanoylamino}ethyl)amide;

(19-45) pentanoic acid [2-chloro-2'-((S)-2-hydroxy-propionylsulfamoyl)biphenyl-4-ylmethyl]-{2-[(S)-2-cyclohexyl-3-mercapto-propionylamino]ethyl}amide;

(19-46) pentanoic acid (2'-acetylsulfamoyl-2-chlorobiphenyl-4-ylmethyl){2-[(S)-2-(2-fluorobenzyl)-3-mercaptopropionylamino]ethyl}amide;

(19-47) pentanoic acid (2'-acetylsulfamoyl-2-chlorobiphenyl-4-ylmethyl){2-[(S)-2-(3-chlorobenzyl)-3-mercaptopropionylamino]ethyl}amide;

(19-48) pentanoic acid (2'-acetylsulfamoyl-2-chlorobiphenyl-4-ylmethyl){2-[(S)-2-benzyl-3-mercaptopropionylamino]ethyl}amide;

(19-49) (S)-2-mercaptomethyl-4-methylpentanoic acid {2-[(2'-acetyl sulfamoyl-2-chlorobiphenyl-4-ylmethyl)pentanoylamino]ethyl}amide;

(19-50) pentanoic acid (2'-acetylsulfamoyl-2-chlorobiphenyl-4-ylmethyl){2-[(S)-2-cyclohexyl-3-mercaptopropionylamino]ethyl}amide;

(19-51) pentanoic acid [2-chloro-2'-((S)-2-hydroxy-propionylsulfamoyl)biphenyl-4-ylmethyl]-{2-[(R)-2-(2-fluorobenzyl)-2-mercaptoethylcarbamoyl]ethyl}amide;

(19-52) pentanoic acid [2-chloro-2'-((S)-2-hydroxy-propionylsulfamoyl)biphenyl-4-ylmethyl]-{2-[(R)-2-(3-chlorobenzyl)-2-mercaptoethylcarbamoyl]ethyl}amide;

(19-53) pentanoic acid [2-chloro-2'-((S)-2-hydroxypropionylsulfamoyl)biphenyl-4-ylmethyl]-{2-[(R)-2-benzyl-2-mercaptoethylcarbamoyl]ethyl}amide;

(19-54) pentanoic acid [2-chloro-2'-((S)-2-hydroxypropionylsulfamoyl)biphenyl-4-ylmethyl][2-((R)-1-mercaptomethyl-3-methylbutylcarbamoyl)ethyl]amide;

(19-55) pentanoic acid [2-chloro-2'-((S)-2-hydroxy-propionylsulfamoyl)biphenyl-4-ylmethyl]-{2-[(S)-2-cyclohexyl-2-mercaptoethylcarbamoyl]ethyl}amide;

(19-56) pentanoic acid (2'-acetylsulfamoyl-2-chlorobiphenyl-4-ylmethyl){2-[(R)-2-(2-fluorobenzyl)-2-mercaptoethylcarbamoyl]ethyl}amide;

(19-57) pentanoic acid (2'-acetylsulfamoyl-2-chlorobiphenyl-4-ylmethyl){2-[(R)-2-(3-chlorobenzyl)-2-mercaptoethylcarbamoyl]ethyl}amide;

(19-58) pentanoic acid (2'-acetylsulfamoyl-2-chlorobiphenyl-4-ylmethyl){2-[(R)-2-benzyl-2-mercaptoethylcarbamoyl]ethyl}amide;

(19-59) pentanoic acid (2'-acetylsulfamoyl-2-chlorobiphenyl-4-ylmethyl)[2-((R)-1-mercaptomethyl-3-methylbutylcarbamoyl)ethyl]amide; and (19-60) pentanoic acid (2'-acetylsulfamoyl-2-chlorobiphenyl-4-ylmethyl){2-[(R)-2-cyclohexyl-2-mercaptoethylcarbamoyl]ethyl}amide; and pharmaceutically acceptable salts thereof.

Example 20

Following the procedures described in Examples above, and substituting the appropriate starting materials and reagents, compounds 20-1 to 20-27 and 20-29 to 20-60, having the following formulas (20a), (20b), (20c), (20d), (20e), or (20f), can also be prepared. Compound 20-28 was synthesized in a manner similar to that described in Example 8.

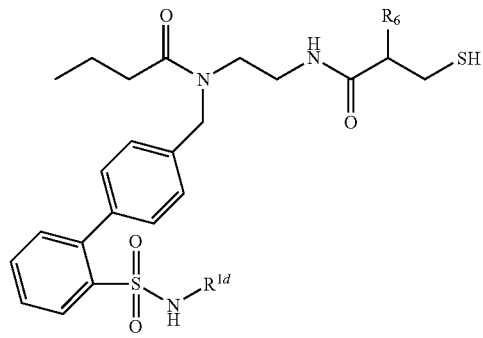

(20a)

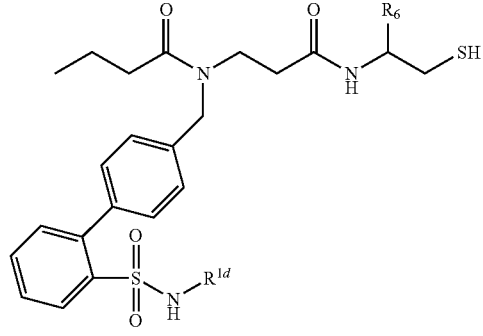

(20b)

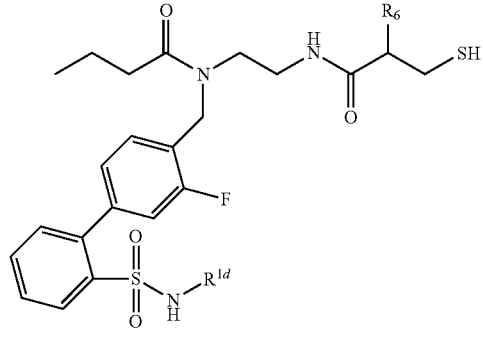

(20c)

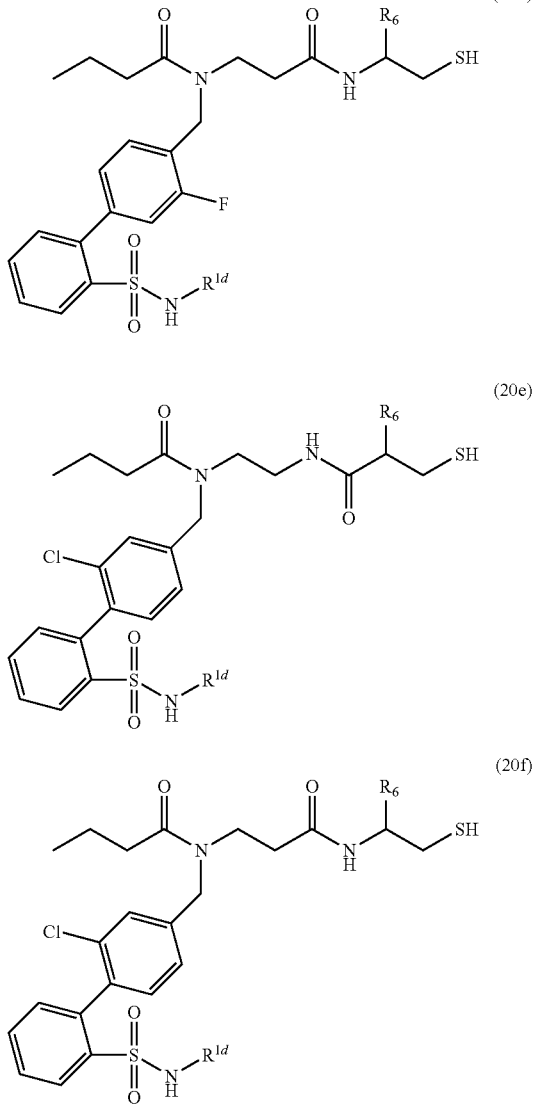

| Ex. | Formula | $R^{1d}$ | $R^6$ |
|---|---|---|---|
| 20-1 | 20a | —C(O)—CH(CH₃)OH | -2-fluorobenzyl |
| 20-2 | 20a | —C(O)—CH(CH₃)OH | -3-chlorobenzyl |
| 20-3 | 20a | —C(O)—CH(CH₃)OH | benzyl |
| 20-4 | 20a | —C(O)—CH(CH₃)OH | i-butyl |
| 20-5 | 20a | —C(O)—CH(CH₃)OH | cyclohexyl |
| 20-6 | 20a | —C(O)CH₃ | -2-fluorobenzyl |
| 20-7 | 20a | —C(O)CH₃ | -3-chlorobenzyl |
| 20-8 | 20a | —C(O)CH₃ | benzyl |
| 20-9 | 20a | —C(O)CH₃ | i-butyl |
| 20-10 | 20a | —C(O)CH₃ | cyclohexyl |
| 20-11 | 20b | —C(O)—CH(CH₃)OH | -2-fluorobenzyl |
| 20-12 | 20b | —C(O)—CH(CH₃)OH | -3-chlorobenzyl |
| 20-13 | 20b | —C(O)—CH(CH₃)OH | benzyl |
| 20-14 | 20b | —C(O)—CH(CH₃)OH | i-butyl |
| 20-15 | 20b | —C(O)—CH(CH₃)OH | cyclohexyl |
| 20-16 | 20b | —C(O)CH₃ | -2-fluorobenzyl |
| 20-17 | 20b | —C(O)CH₃ | -3-chlorobenzyl |
| 20-18 | 20b | —C(O)CH₃ | benzyl |
| 20-19 | 20b | —C(O)CH₃ | i-butyl |
| 20-20 | 20b | —C(O)CH₃ | cyclohexyl |
| 20-21 | 20c | —C(O)—CH(CH₃)OH | -2-fluorobenzyl |
| 20-22 | 20c | —C(O)—CH(CH₃)OH | -3-chlorobenzyl |
| 20-23 | 20c | —C(O)—CH(CH₃)OH | benzyl |
| 20-24 | 20c | —C(O)—CH(CH₃)OH | i-butyl |
| 20-25 | 20c | —C(O)—CH(CH₃)OH | cyclohexyl |
| 20-26 | 20c | —C(O)CH₃ | -2-fluorobenzyl |
| 20-27 | 20c | —C(O)CH₃ | -3-chlorobenzyl |
| 20-28 | 20c | —C(O)CH₃ | benzyl |
| 20-29 | 20c | —C(O)CH₃ | i-butyl |
| 20-30 | 20c | —C(O)CH₃ | cyclohexyl |
| 20-31 | 20d | —C(O)—CH(CH₃)OH | -2-fluorobenzyl |
| 20-32 | 20d | —C(O)—CH(CH₃)OH | -3-chlorobenzyl |
| 20-33 | 20d | —C(O)—CH(CH₃)OH | benzyl |
| 20-34 | 20d | —C(O)—CH(CH₃)OH | i-butyl |
| 20-35 | 20d | —C(O)—CH(CH₃)OH | cyclohexyl |
| 20-36 | 20d | —C(O)CH₃ | -2-fluorobenzyl |
| 20-37 | 20d | —C(O)CH₃ | -3-chlorobenzyl |
| 20-38 | 20d | —C(O)CH₃ | benzyl |
| 20-39 | 20d | —C(O)CH₃ | i-butyl |
| 20-40 | 20d | —C(O)CH₃ | cyclohexyl |
| 20-41 | 20e | —C(O)—CH(CH₃)OH | -2-fluorobenzyl |
| 20-42 | 20e | —C(O)—CH(CH₃)OH | -3-chlorobenzyl |
| 20-43 | 20e | —C(O)—CH(CH₃)OH | benzyl |
| 20-44 | 20e | —C(O)—CH(CH₃)OH | i-butyl |
| 20-45 | 20e | —C(O)—CH(CH₃)OH | cyclohexyl |
| 20-46 | 20e | —C(O)CH₃ | -2-fluorobenzyl |
| 20-47 | 20e | —C(O)CH₃ | -3-chlorobenzyl |
| 20-48 | 20e | —C(O)CH₃ | benzyl |
| 20-49 | 20e | —C(O)CH₃ | i-butyl |
| 20-50 | 20e | —C(O)CH₃ | cyclohexyl |
| 20-51 | 20f | —C(O)—CH(CH₃)OH | -2-fluorobenzyl |
| 20-52 | 20f | —C(O)—CH(CH₃)OH | -3-chlorobenzyl |
| 20-53 | 20f | —C(O)—CH(CH₃)OH | benzyl |
| 20-54 | 20f | —C(O)—CH(CH₃)OH | i-butyl |
| 20-55 | 20f | —C(O)—CH(CH₃)OH | cyclohexyl |
| 20-56 | 20f | —C(O)CH₃ | -2-fluorobenzyl |
| 20-57 | 20f | —C(O)CH₃ | -3-chlorobenzyl |
| 20-58 | 20f | —C(O)CH₃ | benzyl |
| 20-59 | 20f | —C(O)CH₃ | i-butyl |
| 20-60 | 20f | —C(O)CH₃ | cyclohexyl |

These compounds are named below. Although the nomenclature depicts one stereoisomer embodiment, it is understood that all stereoisomeric forms of these compounds are included in the invention.

(20-1) N-{2-[(S)-2-(2-fluorobenzyl)-3-mercaptopropionylamino]ethyl}-N-[2'-((S)-2-hydroxypropionylsulfamoyl)biphenyl-4-ylmethyl]butyramide;

(20-2) N-{2-[(S)-2-(3-chlorobenzyl)-3-mercaptopropionylamino]ethyl}-N-[2'-((S)-2-hydroxypropionylsulfamoyl)biphenyl-4-ylmethyl]butyramide;

(20-3) N-{2-((S)-2-benzyl-3-mercaptopropionylamino)ethyl}-N-[2'-((S)-2-hydroxypropionylsulfamoyl)biphenyl-4-ylmethyl]butyramide;

(20-4) (S)-2-mercaptomethyl-4-methylpentanoic acid (2-{butyryl-[2'-((S)-2-hydroxypropionylsulfamoyl)biphenyl-4-ylmethyl]amino}ethyl)amide;

(20-5) N-[2-((S)-2-cyclohexyl-3-mercaptopropionylamino)ethyl]-N-[2'-((S)-2-hydroxypropionylsulfamoyl)biphenyl-4-ylmethyl]butyramide;

(20-6) N-(2'-acetylsulfamoyl-biphenyl-4-ylmethyl)-N-{2-[(S)-2-(2-fluorobenzyl)-3-mercaptopropionylamino]ethyl}butyramide;

(20-7) N-(2'-acetylsulfamoyl-biphenyl-4-ylmethyl)-N-{2-[(S)-2-(3-chlorobenzyl)-3-mercaptopropionylamino]ethyl}butyramide;

(20-8) N-(2'-acetylsulfamoyl-biphenyl-4-ylmethyl)-N-{2-[(S)-2-benzyl-3-mercaptopropionylamino]ethyl}butyramide;

(20-9) (S)-2-mercaptomethyl-4-methylpentanoic acid {2-[(2'-acetylsulfamoylbiphenyl-4-ylmethyl)butyrylamino]ethyl}amide;

(20-10) N-(2'-acetylsulfamoyl-biphenyl-4-ylmethyl)-N-{2-[(S)-2-cyclohexyl-3-mercaptopropionylamino]ethyl}butyramide;

(20-11) N-{2-[(R)-2-(2-fluorobenzyl)-2-mercaptoethylcarbamoyl]ethyl}-N-[2'-((S)-2-hydroxypropionylsulfamoyl)biphenyl-4-ylmethyl]butyramide;

(20-12) N-{2-[(R)-2-(3-chlorobenzyl)-2-mercaptoethylcarbamoyl]ethyl}-N-[2'-((S)-2-hydroxypropionylsulfamoyl)biphenyl-4-ylmethyl]butyramide;

(20-13) N-[2-((R)-2-benzyl-2-mercaptoethylcarbamoyl)ethyl]-N-[2'-((S)-2-hydroxypropionylsulfamoyl)biphenyl-4-ylmethyl]butyramide;

(20-14) N-[2'-((S)-2-hydroxypropionylsulfamoyl)biphenyl-4-ylmethyl]-N-[2-((R)-1-mercaptomethyl-3-methyl-butylcarbamoyl)ethyl]butyramide;

(20-15) N-[2-((R)-2-cyclohexyl-2-mercaptoethylcarbamoyl)ethyl]-N-[2'-((S)-2-hydroxypropionylsulfamoyl)biphenyl-4-ylmethyl]butyramide;

(20-16) N-(2'-acetylsulfamoyl-biphenyl-4-ylmethyl)-N-{2-[(R)-2-(2-fluorobenzyl)-2-mercaptoethylcarbamoyl]ethyl}butyramide;

(20-17) N-(2'-acetylsulfamoyl-biphenyl-4-ylmethyl)-N-{2-[(R)-2-(3-chlorobenzyl)-2-mercaptoethylcarbamoyl]ethyl}butyramide;

(20-18) N-(2'-acetylsulfamoyl-biphenyl-4-ylmethyl)-N-{2-[(R))-2-benzyl-2-mercaptoethylcarbamoyl]ethyl}butyramide;

(20-19) N-(2'-acetylsulfamoylbiphenyl-4-ylmethyl)-N-[2-((R)-1-mercaptomethyl-3-methylbutylcarbamoyl)ethyl]butyramide;

(20-20) N-(2'-acetylsulfamoyl-biphenyl-4-ylmethyl)-N-{2-[(R)-2-cyclohexyl-2-mercaptoethylcarbamoyl]ethyl}butyramide;

(20-21) N-{2-[(S)-2-(2-fluorobenzyl)-3-mercaptopropionylamino]ethyl}-N-[3-fluoro-2'-((S)-2-hydroxy-propionylsulfamoyl)biphenyl-4-ylmethyl]butyramide;

(20-22) N-{2-[(S)-2-(3-chlorobenzyl)-3-mercaptopropionylamino]ethyl}-N-[3-fluoro-2'-((S)-2-hydroxypropionylsulfamoyl)biphenyl-4-ylmethyl]butyramide;

(20-23) N-{2-[(S)-2-benzyl-3-mercaptopropionylamino]ethyl}-N-[3-fluoro-2'-((S)-2-hydroxypropionylsulfamoyl)biphenyl-4-ylmethyl]butyramide;

(20-24) (S)-2-mercaptomethyl-4-methylpentanoic acid (2-{butyryl-[3-fluoro-2'-((S)-2-hydroxypropionylsulfamoyl)biphenyl-4-ylmethyl]amino}ethyl)amide;

(20-25) N-{2-[(S)-2-cyclohexyl-3-mercaptopropionylamino]ethyl}-N-[3-fluoro-2'-((S)-2-hydroxypropionylsulfamoyl)biphenyl-4-ylmethyl]butyramide;

(20-26) N-(2'-acetylsulfamoyl-3-fluorobiphenyl-4-ylmethyl)-N-{2-[(S)-2-(2-fluorobenzyl)-3-mercaptopropionylamino]ethyl}butyramide;

(20-27) N-(2'-acetylsulfamoyl-3-fluorobiphenyl-4-ylmethyl)-N-{2-[(S)-2-(3-chlorobenzyl)-3-mercaptopropionylamino]ethyl}butyramide;

(20-28) N-(2'-acetylsulfamoyl-3-fluorobiphenyl-4-ylmethyl)-N-[2-((S)-2-benzyl-3-mercaptopropionylamino)ethyl]butyramide, MS m/z: [M+H⁺] calcd for $C_{31}H_{36}FN_3O_5S_2$, 614.21. found 614.0 (this compound was synthesized in a manner similar to that described in Example 8);

(20-29) (S)-2-mercaptomethyl-4-methylpentanoic acid {2-[(2'-acetylsulfamoyl-3-fluorobiphenyl-4-ylmethyl)butyrylamino]ethyl}amide;

(20-30) N-(2'-acetylsulfamoyl-3-fluorobiphenyl-4-ylmethyl)-N-[2-((S)-2-cyclohexyl-3-mercaptopropionylamino)ethyl]butyramide;

(20-31) N-{2-[(R)-2-(2-fluorobenzyl)-2-mercaptoethylcarbamoyl]ethyl}-N-[3-fluoro-2'-((S)-2-hydroxy-propionylsulfamoyl)biphenyl-4-ylmethyl]butyramide;

(20-32) N-{2-[(R)-2-(3-chlorobenzyl)-2-mercaptoethylcarbamoyl]ethyl}-N-[3-fluoro-2'-((S)-2-hydroxy-propionylsulfamoyl)biphenyl-4-ylmethyl]butyramide;

(20-33) N-{2-[(R)-2-benzyl-2-mercaptoethylcarbamoyl]ethyl}-N-[3-fluoro-2'-((S)-2-hydroxy-propionylsulfamoyl)biphenyl-4-ylmethyl]butyramide;

(20-34) N-[3-fluoro-2'-((S)-2-hydroxypropionylsulfamoyl)biphenyl-4-ylmethyl]-N-[2-((R)-1-mercaptomethyl-3-methylbutylcarbamoyl)ethyl]butyramide;

(20-35) N-{2-[(R)-2-cyclohexyl-2-mercaptoethylcarbamoyl]ethyl}-N-[3-fluoro-2'-((S)-2-hydroxy-propionylsulfamoyl)biphenyl-4-ylmethyl]butyramide;

(20-36) N-(2'-acetylsulfamoyl-3-fluorobiphenyl-4-ylmethyl)-N-{2-[(R))-2-(2-fluorobenzyl)-2-mercaptoethylcarbamoyl]ethyl}butyramide;

(20-37) N-(2'-acetylsulfamoyl-3-fluorobiphenyl-4-ylmethyl)-N-{2-[(R)-2-(3-chlorobenzyl)-2-mercaptoethylcarbamoyl]ethyl}butyramide;

(20-38) N-(2'-acetylsulfamoyl-3-fluorobiphenyl-4-ylmethyl)-N-[2-((R)-2-benzyl-2-mercaptoethylcarbamoyl)ethyl]butyramide;

(20-39) N-(2'-acetylsulfamoyl-3-fluorobiphenyl-4-ylmethyl)-N-[2-((R)-1-mercaptomethyl-3-methylbutylcarbamoyl)ethyl]butyramide;

(20-40) N-(2'-acetylsulfamoyl-3-fluorobiphenyl-4-ylmethyl)-N-[2-((R)-2-cyclohexyl-2-mercaptoethylcarbamoyl)ethyl]butyramide;

(20-41) N-[2-chloro-2'-((S)-2-hydroxypropionylsulfamoyl)biphenyl-4-ylmethyl]-N-{2-[(S)-2-(2-fluorobenzyl)-3-mercaptopropionylamino]ethyl}butyramide;

(20-42) N-[2-chloro-2'-((S)-2-hydroxypropionylsulfamoyl)biphenyl-4-ylmethyl]-N-{2-[(S)-2-(3-chlorobenzyl)-3-mercaptopropionylamino]ethyl}butyramide;

(20-43) N-[2-chloro-2'-((S)-2-hydroxypropionylsulfamoyl)biphenyl-4-ylmethyl]-N-{2-[(S)-2-benzyl-3-mercaptopropionylamino]ethyl}butyramide;

(20-44) (S)-2-mercaptomethyl-4-methylpentanoic acid (2-{butyryl-[2-chloro-2'-((S)-2-hydroxypropionylsulfamoyl)biphenyl-4-ylmethyl]amino}ethyl)amide;

(20-45) N-[2-chloro-2'-((S)-2-hydroxypropionylsulfamoyl)biphenyl-4-ylmethyl]-N-{2-[(S)-2-cyclohexyl)-3-mercaptopropionylamino]ethyl}butyramide;

(20-46) N-(2'-acetylsulfamoyl-2-chlorobiphenyl-4-ylmethyl)-N-{2-[(S)-2-(2-fluorobenzyl)-3-mercaptopropionylamino]ethyl}butyramide;

(20-47) N-(2'-acetylsulfamoyl-2-chlorobiphenyl-4-ylmethyl)-N-{2-[(S)-2-(3-chlorobenzyl)-3-mercaptopropionylamino]ethyl}butyramide;

(20-48) N-(2'-acetylsulfamoyl-2-chlorobiphenyl-4-ylmethyl)-N-{2-[(S)-2-benzyl-3-mercaptopropionylamino]ethyl}butyramide;

(20-49) (S)-2-mercaptomethyl-4-methylpentanoic acid {2-[(T-acetylsulfamoyl-2-chlorobiphenyl-4-ylmethyl)butyrylamino]ethyl}amide;

(20-50) N-(2'-acetylsulfamoyl-2-chlorobiphenyl-4-ylmethyl)-N-{2-[(S)-2-cyclohexyl-3-mercaptopropionylamino]ethyl}butyramide;

(20-51) N-[2-chloro-2'-((S)-2-hydroxypropionylsulfamoyl)biphenyl-4-ylmethyl]-N-{2-[(R)-2-(2-fluorobenzyl)-2-mercaptoethylcarbamoyl]ethyl}butyramide;

(20-52) N-[2-chloro-2'-((S)-2-hydroxypropionylsulfamoyl)biphenyl-4-ylmethyl]-N-{2-[(R)-2-(3-chlorobenzyl)-2-mercaptoethylcarbamoyl]ethyl}butyramide;

(20-53) N-[2-chloro-2'-((S)-2-hydroxypropionylsulfamoyl)biphenyl-4-ylmethyl]-N-{2-[(R)-2-benzyl-2-mercaptoethylcarbamoyl]ethyl}butyramide;

(20-54) N-[2-chloro-2'-((S)-2-hydroxypropionylsulfamoyl)biphenyl-4-ylmethyl]-N-[2-((R)-1-mercaptomethyl-3-methylbutylcarbamoyl)ethyl]butyramide;

(20-55) N-[2-chloro-2'-((S)-2-hydroxypropionylsulfamoyl)biphenyl-4-ylmethyl]-N-{2-[(R)-2-cyclohexyl)-2-mercaptoethylcarbamoyl]ethyl}butyramide;

(20-56) N-(2'-acetylsulfamoyl-2-chlorobiphenyl-4-ylmethyl)-N-{2-[(R)-2-(2-fluorobenzyl)-2-mercaptoethylcarbamoyl]ethyl}butyramide;

(20-57) N-(2'-acetylsulfamoyl-2-chlorobiphenyl-4-ylmethyl)-N-{2-[(R)-2-(3-chlorobenzyl)-2-mercaptoethylcarbamoyl]ethyl}butyramide;

(20-58) N-(2'-acetylsulfamoyl-2-chlorobiphenyl-4-ylmethyl)-N-{2-[(R)-2-benzyl-2-mercaptoethylcarbamoyl]ethyl}butyramide;

(20-59) N-(2'-acetylsulfamoyl-2-chlorobiphenyl-4-ylmethyl)-N-[2-((R)-1-mercaptomethyl-3-methyl-butylcarbamoyl)ethyl]butyramide; and (20-60) N-(2'-acetylsulfamoyl-2-chlorobiphenyl-4-ylmethyl)-N-{2-[(R)-2-cyclohexyl-2-mercaptoethylcarbamoyl]ethyl}butyramide; and pharmaceutically acceptable salts thereof.

Assay 1

$AT_1$ and $AT_2$ Radioligand Binding Assays

These in vitro assays were used to assess the ability of test compounds to bind to the $AT_1$ and the $AT_2$ receptors.

Membrane Preparation from Cells Expressing Human $AT_1$ or $AT_2$ Receptors

Chinese hamster ovary (CHO-K1) derived cell lines stably expressing the cloned human $AT_1$ or $AT_2$ receptors, respectively, were grown in HAM's-F12 medium supplemented with 10% fetal bovine serum, 10 μg/ml penicillin/streptomycin, and 500 μg/ml geneticin in a 5% $CO_2$ humidified incubator at 37° C. $AT_2$ receptor expressing cells were grown in the additional presence of 100 nM PD123,319 ($AT_2$ antagonist). When cultures reached 80-95% confluence, the cells were washed thoroughly in PBS and lifted with 5 mM EDTA. Cells were pelleted by centrifugation and snap frozen in MeOH-dry ice and stored at −80° C. until further use.

For membrane preparation, cell pellets were resuspended in lysis buffer (25 mM Tris/HCl pH 7.5 at 4° C., 1 mM EDTA, and one tablet of Complete Protease Inhibitor Cocktail Tablets with 2 mM EDTA per 50 mL buffer (Roche cat. #1697498, Roche Molecular Biochemicals, Indianapolis, Ind.)) and homogenized using a tight-fitting Dounce glass homogenizer (10 strokes) on ice. The homogenate was centrifuged at 1000×g, the supernatant was collected and centrifuged at 20,000×g. The final pellet was resuspended in membrane buffer (75 mM Tris/HCl pH 7.5, 12.5 mM $MgCl_2$, 0.3 mM EDTA, 1 mM EGTA, 250 mM sucrose at 4° C.) and homogenized by extrusion through a 20 G gauge needle. Protein concentration of the membrane suspension was determined by the method described in Bradford (1976) *Anal Biochem.* 72:248-54. Membranes were snap frozen in MeOH-dry ice and stored at −80° C. until further use.

Ligand Binding Assay to Determine Compound Affinities for the Human $AT_1$ and $AT_2$ Angiotensin Receptors Binding assays were performed in 96-well Acrowell filter plates (Pall Inc., cat. #5020) in a total assay volume of 100 μL with 0.2 μg membrane protein for membranes containing the human $AT_1$ receptor, or 2 μg membrane protein for membranes containing the human $AT_2$ receptor in assay buffer (50 mM Tris/HCl pH 7.5 at 20° C., 5 mM $MgCl_2$, 25 μM EDTA, 0.025% BSA). Saturation binding studies for determination of $K_d$ values of the ligand were done using N-terminally Europium-labeled angiotensin-II ([Eu]AngII, H—(Eu—N[1])-Ahx-Asp-Arg-Val-Tyr-Ile-His-Pro-Phe-OH; PerkinElmer, Boston, Mass.) at 8 different concentrations ranging from 0.1 nM to 30 nM. Displacement assays for determination of $pK_i$ values of test compounds were done with [Eu]AngII at 2 nM and 11 different concentrations of drug ranging from 1 μM to 10 pM. Drugs were dissolved to a concentration of 1 mM in DMSO and from there serially diluted into assay buffer. Non-specific binding was determined in the presence of 10 μM unlabeled angiotensin-II. Assays were incubated for 120 minutes in the dark, at room temperature or 37° C., and binding reactions were terminated by rapid filtration through the Acrowell filter plates followed by three washes with 200 μL ice cold wash buffer (50 mM Tris/HCl pH 7.5 at 4° C., 5 mM $MgCl_2$) using a Waters filtration manifold. Plates were tapped dry and incubated with 50 μl DELFIA Enhancement Solution (PerkinElmer cat. #4001-0010) at room temperature for 5 minutes on a shaker. Filter-bound [Eu]AngII was quantitated immediately on a Fusion plate reader (PerkinElmer) using Time Resolved Fluorescence (TRF). Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 10 μM angiotensin II. $K_i$ values for drugs were calculated from observed $IC_{50}$ values and the $K_d$ value of [Eu]AngII according to the Cheng-Prusoff equation described in Cheng et al. (1973) *Biochem Pharmacol.* 22(23):3099-108. Selectivities of test compounds for the $AT_1$ receptor over the $AT_2$ receptor were calculated as the ratio of $AT_2K_i/AT_1K_i$. Binding affinities of test compounds were expressed as negative decadic logarithms of the $K_i$ values ($pK_i$).

In this assay, a higher $pK_i$ value indicates that the test compound has a higher binding affinity for the receptor tested. Exemplary compounds of the invention that were tested in this assay, typically were found to have a $pK_i$ at the $AT_1$ receptor greater than or equal to about 5.0. For example, the compound of Example 1 was found to have a $pK_i$ value greater than about 7.0.

Assay 2

In Vitro Assays for the Quantitation of Inhibitor Potencies ($IC_{50}$) at Human and Rat NEP, and Human ACE The inhibitory activities of compounds at human and rat NEP and human ACE were determined using in vitro assays as described below.

Extraction of NEP Activity from Rat Kidneys

Rat NEP was prepared from the kidneys of adult Sprague Dawley rats. Whole kidneys were washed in cold PBS and brought up in ice-cold lysis buffer (1% Triton X-114, 150 mM NaCl, 50 mM Tris pH 7.5; Bordier (1981) *J. Biol. Chem.* 256:1604-1607) in a ratio of 5 mL of buffer for every gram of kidney. Samples were homogenized using a polytron hand held tissue grinder on ice. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with BSA as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-BK2 (Mca-Arg-Pro-Pro-Gly-Phe-Ser-Ala-Phe-Lys(Dnp)-OH; Johnson et al. (2000) *Anal. Biochem.* 286: 112-118) was used for the human NEP and ACE assays, and Mca-RRL (Mca-DArg-Arg-Leu-(Dnp)-OH; Medeiros et al. (1997) *Braz. J. Med. Biol. Res.* 30:1157-1162) was used for the rat NEP assay (both from Anaspec, San Jose, Calif.).

The assays were performed in 384-well white opaque plates at room temperature using the respective fluorogenic peptides at a concentration of 10 μM in assay buffer (50 mM Tris/HCl at 25° C., 100 mM NaCl, 0.01% Tween-20, 1 μM Zn, 0.025% BSA). Human NEP and human ACE were used at concentrations that resulted in quantitative proteolysis of 5 μM of Mca-BK2 within 20 minutes at room temperature. The rat NEP enzyme preparation was used at a concentration that yielded quantitative proteolysis of 3 μM of Mca-RRL within 20 minutes at room temperature.

Assays were started by adding 25 μL of enzyme to 12.5 μL of test compound at 12 concentrations (10 μM to 20 μM). Inhibitors were allowed to equilibrate with the enzyme for 10 minutes before 12.54 of the fluorogenic substrates were added to initiate the reaction. Reactions were terminated by the addition of 10 μL of 3.6% glacial AcOH after 20 minutes of incubation. Plates were read on a fluorometer with excitation and emission wavelengths set to 320 nm and 405 nm, respectively. Raw data (relative fluorescence units) were normalized to % activity from the average high readings (no inhibition, 100% enzyme activity) and average low readings (full inhibition, highest inhibitor concentration, 0% enzyme activity) using three standard NEP and ACE inhibitors, respectively. Nonlinear regression of the normalized data was performed using a one site competition model (GraphPad Software, Inc., San Diego, Calif.). Data were reported as $pIC_{50}$ values.

Exemplary compounds of the invention that were tested in this assay, typically were found to have a $pIC_{50}$ for the NEP enzyme greater than or equal to about 5.0, for example, the compound of Example 1 has a $pIC_{50}$ value greater than or equal to about 7.0.

Assay 3

Pharmacodynamic (PD) Assay for ACE, $AT_1$, and NEP Activity in Anesthetized Rats Male, Sprague Dawley, normotensive rats are anesthetized with 120 mg/kg (i.p.) of inactin. Once anesthetized, the jugular vein, carotid artery (PE 50 tubing) and bladder (URI-1 urinary silicone catheter) are cannulated and a tracheotomy is performed (Teflon Needle, size 14 gauge) to facilitate spontaneous respiration. The animals are then allowed a 60 minute stabilization period and kept continuously infused with 5 mL/kg/h of saline (0.9%) throughout, to keep them hydrated and ensure urine production. Body temperature is maintained throughout the experiment by use of a heating pad. At the end of the 60 minute stabilization period, the animals are dosed intravenously (i.v.) with two doses of angiotensin (AngI, 1.0 μg/kg, for ACE inhibitor activity; AngII, 0.1 μg/kg, for $AT_1$ receptor antagonist activity) at 15 minutes apart. At 15 minutes post-second dose of angiotensin (AngI or AngII), the animals are treated with vehicle or test compound. Five minutes later, the animals are additionally treated with a bolus i.v. injection of atrial natriuretic peptide (ANP; 30 μg/kg). Urine collection (into pre-weighted eppendorf tubes) is started immediately after the ANP treatment and continued for 60 minutes. At 30 and 60 minutes into urine collection, the animals are re-challenged with angiotensin (AngI or AngII). Blood pressure measurements are done using the Notocord system (Kalamazoo, Mich.). Urine samples are frozen at −20° C. until used for the cGMP assay. Urine cGMP concentrations are determined by Enzyme Immuno Assay using a commercial kit (Assay Designs, Ann Arbor, Mich., Cat. No. 901-013). Urine volume is determined gravimetrically. Urinary cGMP output is calculated as the product of urine output and urine cGMP concentration. ACE inhibition or $AT_1$ antagonism is assessed by quantifying the % inhibition of pressor response to AngI or AngII, respectively. NEP inhibition is assessed by quantifying the potentiation of ANP-induced elevation in urinary cGMP output.

Assay 4

In Vivo Evaluation of Antihypertensive Effects in the Conscious SHR Model of Hypertension Spontaneously hypertensive rats (SHR, 14-20 weeks of age) are allowed a minimum of 48 hours acclimation upon arrival at the testing site. Seven days prior to testing, the animals are either placed on a restricted low-salt diet with food containing 0.1% of sodium for sodium depleted SHRs (SD-SHR) or are placed on a normal diet for sodium repleted SHRs (SR-SHR). Two days prior to testing, the animals are surgically implemented with catheters into a carotid artery and the jugular vein (PESO polyethylene tubing) connected via a PE10 polyethylene tubing to a selected silicone tubing (size 0.020 ID×0.037 OD×0.008 wall) for blood pressure measurement and test compound delivery, respectively. The animals are allowed to recover with appropriate post operative care.

On the day of the experiment, the animals are placed in their cages and the catheters are connected via a swivel to a calibrated pressure transducer. After 1 hour of acclimation, a baseline measurement is taken over a period of at least five minutes. The animals are then dosed i.v. with vehicle or test compound in ascending cumulative doses every 60 minutes followed by a 0.3 mL saline to clear the catheter after each dose. Data is recorded continuously for the duration of the study using Notocord software (Kalamazoo, Mich.) and stored as electronic digital signals. In some studies, the effects of a single intravenous or oral (gavage) dose are monitored for at least 6 hours after dosing. Parameters measured are blood pressure (systolic, diastolic and mean arterial pressure) and heart rate.

Assay 5

In Vivo Evaluation of Antihypertensive Effects in the Conscious DOCA-Salt Rat Model of Hypertension CD rats (male, adult, 200-300 grams, Charles River Laboratory, USA) are allowed a minimum of 48 hours acclimation upon arrival at the testing site before they are placed on a high salt diet.

One week after the start of the high salt diet, a DOCA-salt pellet (100 mg, 21 days release time, Innovative Research of America, Sarasota, Fla.) is implanted subcutaneously and unilateral nephrectomy is performed. On 16 or 17 days post DOCA-salt pellet implantation, animals are implanted surgically with catheters into a carotid artery and the jugular vein with a PE50 polyethylene tubing, which in turn was connected via a PE10 polyethylene tubing to a selected silicone tubing (size 0.020 ID×0.037 OD×0.008 wall) for blood pressure measurement and test compound delivery, respectively. The animals are allowed to recover with appropriate post operative care.

On the day of the experiment, each animal is kept in its cage and connected via a swivel to a calibrated pressure transducer. After 1 hour of acclimation, a baseline measurement is taken over a period of at least five minutes. The animals are then dosed i.v. with a vehicle or test compound in escalating cumulative doses every 60 minutes followed by 0.3 mL of saline to flush the catheter after each dose. In some studies, the effects of a single intravenous or oral (gavage) dose is tested and monitored for at least 6 hours after dosing. Data is recorded continuously for the duration of the study using Notocord software (Kalamazoo, Mich.) and stored as electronic digital signals. Parameters measured are blood pressure (systolic, diastolic and mean arterial pressure) and heart rate. For cumulative and single dosing, the percentage change in mean arterial pressure (MAP, mmHg) or heart rate (HR, bpm) is determined as described for Assay 4.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A method for treating heart failure, comprising administering to a patient a therapeutically effective amount of a compound of formula I:

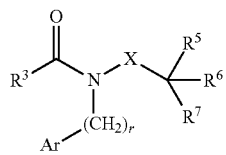
(I)

wherein:

r is 0, 1 or 2;

Ar is an aryl group selected from:

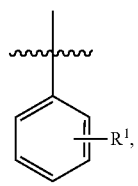, 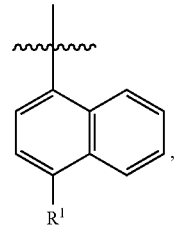, 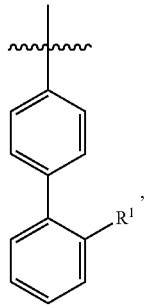

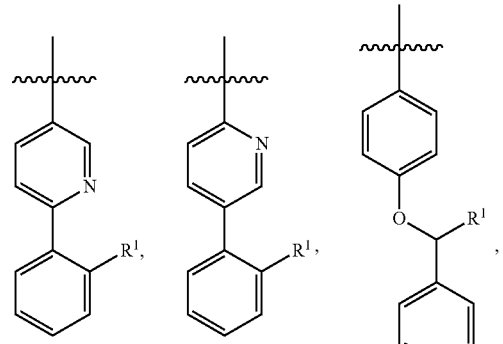

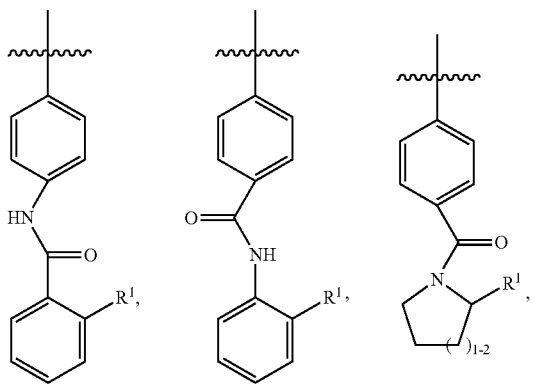

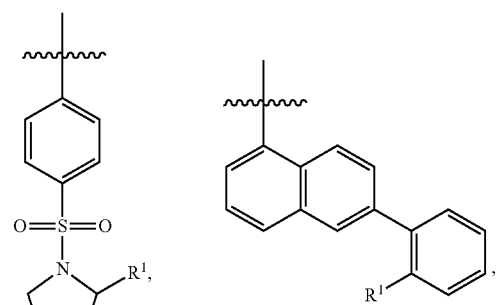

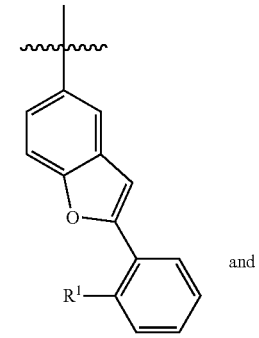
and

-continued

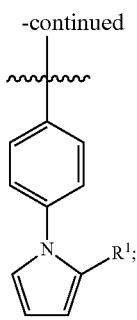

$R^1$ is selected from —COOR$^{1a}$, —NHSO$_2$R$^{1b}$, —SO$_2$NHR$^{1d}$, —SO$_2$OH, —C(O)NH—SO$_2$R$^{1c}$, —P(O)(OH)$_2$, —CN, —O—CH(R$^{1e}$)—COOH, tetrazol-5-yl,

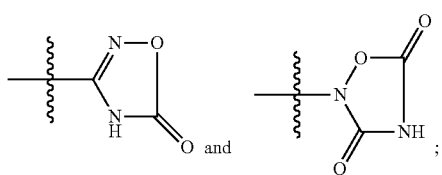 [SMILES: *c1noc(=O)[nH]1 ; *n1oc(=O)[nH]c1=O]

$R^{1a}$ is H, —C$_{1-6}$alkyl, —C$_{1-3}$alkylenearyl, —C$_{1-3}$alkyleneheteroaryl, —C$_{3-6}$cycloalkyl, —CH(C$_{1-4}$-alkyl)OC(O)R$^{1aa}$, —C$_{0-6}$alkylenemorpholine,

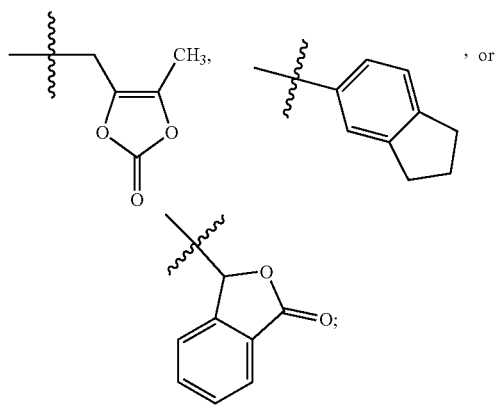

$R^{1aa}$ is —O—C$_{1-6}$alkyl, —O-cycloalkyl, —NR$^{1ab}$R$^{1ac}$, or —CH(NH$_2$)CH$_2$COOCH$_3$; R$^{1ab}$ and R$^{1ac}$ are independently selected from H, —C$_{1-6}$alkyl, and benzyl, or are taken together as —(CH$_2$)$_{3-6}$—; R$^{1b}$ is R$^{1c}$ or —NHC(O)R$^{1c}$; R$^{1c}$ is —C$_{1-6}$alkyl, —C$_{0-6}$alkylene-O—R$^{1ca}$, —C$_{1-5}$alkylene-NR$^{1cb}$R$^{1cc}$, or —C$_{0-4}$alkylenearyl; R$^{1ca}$ is H, —C$_{1-6}$alkyl, or —C$_{1-6}$alkylene-O—C$_{1-6}$alkyl; R$^{1cb}$ and R$^{1cc}$ are independently selected from H and —C$_{1-6}$alkyl, or are taken together as —(CH$_2$)$_2$—O—(CH$_2$)$_2$— or —(CH$_2$)$_2$—N[C(O)CH$_3$]—(CH$_2$)$_2$—; R$^{1d}$ is H, R$^{1c}$, —C(O)R$^{1c}$, or —C(O)NHR$^{1c}$; R$^{1e}$ is —C$_{1-4}$-alkyl or aryl;

$R^3$ is selected from —C$_{1-10}$alkyl, —C$_{2-10}$-alkenyl, —C$_{3-10}$alkynyl, —C$_{0-3}$alkylene-C$_{3-7}$cycloalkyl, —C$_{2-3}$alkenylene-C$_{3-7}$cycloalkyl, —C$_{2-3}$alkynylene-C$_{3-7}$cycloalkyl, —C$_{0-5}$alkylene-NR$^{3a}$—C$_{0-5}$alkylene-R$^{3b}$, —C$_{0-5}$alkylene-O—C$_{0-5}$alkylene-R$^{3b}$, —C$_{1-5}$alkylene-S—C$_{1-5}$alkylene-R$^{3b}$, and —C$_{0-3}$alkylenearyl;

$R^{3a}$ is H, —C$_{1-6}$alkyl, —C$_{3-6}$cycloalkyl, or —C$_{0-3}$alkylenearyl; and R$^{3b}$ is H, —C$_{1-6}$alkyl, —C$_{3-6}$cycloalkyl, —C$_{2-4}$alkenyl, —C$_{2-4}$alkynyl, or aryl;

X is —C$_{1-12}$alkylene-, where at least one —CH$_2$— moiety in the alkylene is replaced with a —NR$^{4a}$—C(O)— or —C(O)—NR$^{4a}$-moiety, where R$^{4a}$ is selected from H, —OH, and —C$_{1-4}$alkyl;

$R^5$ is selected from —C$_{0-3}$alkylene-SR$^{5a}$, —C$_{0-3}$alkylene-C(O)NR$^{5b}$R$^{5c}$, and —C$_{0-3}$alkylene-NR$^{5b}$—C(O)R$^{5d}$; where R$^{5a}$ is H or —C(O)—R$^{5aa}$; R$^{5aa}$ is —C$_{1-6}$alkyl, —C$_{0-6}$alkylene-C$_{3-7}$cycloalkyl, —C$_{0-6}$alkylenearyl, —C$_{0-6}$alkyleneheteroaryl, —C$_{0-6}$alkylenemorpholine, —C$_{0-6}$alkylenepiperazine-CH$_3$, —CH(NH$_2$)-aa where aa is an amino acid side chain, -2-pyrrolidine, —C$_{0-6}$alkylene-OR$^{5ab}$, —OC$_{0-6}$alkylenearyl, —C$_{1-2}$alkylene-OC(O)—C$_{1-6}$alkyl, —C$_{1-2}$alkylene-OC(O)—C$_{0-6}$alkylenearyl, or —O—C$_{1-2}$alkylene-OC(O)—O—C$_{1-6}$alkyl; R$^{5ab}$ is H or —C$_{1-6}$alkyl; R$^{5b}$ is H, —OH, —OC(O)R$^{5ba}$, —CH$_2$COOH, —O-benzyl, -pyridyl, or —OC(S)NR$^{5bb}$R$^{5bc}$; R$^{5ba}$ is —C$_{1-6}$alkyl, —OCH$_2$-aryl, —CH$_2$O-aryl, or —NR$^{5bb}$R$^{5bc}$; R$^{5bb}$ and R$^{5bc}$ are independently selected from H and —C$_{1-4}$-alkyl; R$^{5c}$ is H, —C$_{1-6}$alkyl, or —C(O)—R$^{5ca}$; R$^{5ca}$ is —C$_{1-6}$alkyl, —C$_{3-7}$cycloalkyl, aryl, or heteroaryl; R$^{5d}$ is H, —C$_{1-4}$-alkyl, —C$_{0-3}$alkylenearyl, —NR$^{5da}$R$^{5db}$, —CH$_2$SH, or —O—C$_{1-6}$alkyl; R$^{5da}$ and R$^{5db}$ are independently selected from H and —C$_{1-4}$-alkyl;

$R^6$ is selected from —C$_{1-6}$alkyl, —CH$_2$—O—(CH$_2$)$_2$OCH$_3$, —C$_{1-6}$alkylene-O—C$_{1-6}$alkyl, —C$_{0-3}$alkylenearyl, —C$_{0-3}$alkyleneheteroaryl, and —C$_{0-3}$alkylene-C$_{3-7}$ cycloalkyl; and $R^7$ is H or is taken together with R$^6$ to form —C$_{3-8}$cycloalkyl;

wherein: each —CH$_2$— group in —(CH$_2$)$_r$— is optionally substituted with 1 or 2 substituents independently selected from —C$_{1-4}$-alkyl and fluoro;

each carbon atom in X is optionally substituted with one or more R$^{4b}$ groups and one —CH$_2$— moiety in X may be replaced with a group selected from —C$_{4-8}$cycloalkylene-, —CR$^{4d}$=CH—, and —CH=CR$^{4d}$—; wherein R$^{4b}$ is selected from —C$_{0-5}$alkylene-COOR$^{4c}$, —C$_{1-6}$alkyl, —C$_{0-1}$alkylene-CONH$_2$, —C$_{1-2}$alkylene-OH, —C$_{0-3}$alkylene-C$_{3-7}$cycloalkyl, 1H-indol-3-yl, benzyl, and hydroxybenzyl, where R$^{4c}$ is H or —C$_{1-4}$-alkyl; and R$^{4d}$ is selected from —CH$_2$-thiophene and phenyl;

each alkyl and each aryl in R$^1$, R$^3$, R$^{4a-4d}$, and R$^{5-6}$ is optionally substituted with 1 to 7 fluoro atoms;

each ring in Ar and each aryl in R$^1$, R$^3$, and R$^{5-6}$ is optionally substituted with 1 to 3 substituents independently selected from —OH, —C$_{1-6}$alkyl, —C$_{2-4}$alkenyl, —C$_{2-4}$ alkynyl, —CN, halo, —O—C$_{1-6}$alkyl, —S—C$_{1-6}$ alkyl, —S(O)—C$_{1-6}$alkyl, —S(O)$_2$—C$_{1-4}$-alkyl, -phenyl, —NO$_2$, —NH$_2$, —NH—C$_{1-6}$alkyl and —N(C$_{1-6}$alkyl)$_2$, wherein each alkyl, alkenyl and alkynyl is optionally substituted with 1 to 5 fluoro atoms;

and pharmaceutically acceptable salts thereof.

* * * * *